United States Patent
Anryu et al.

(10) Patent No.: US 9,645,490 B2
(45) Date of Patent: May 9, 2017

(54) SALT, ACID GENERATOR, PHOTORESIST COMPOSITION, AND METHOD FOR PRODUCING PHOTORESIST PATTERN

(71) Applicant: SUMITOMO CHEMICAL COMPANY, LIMITED, Tokyo (JP)

(72) Inventors: Yukako Anryu, Osaka (JP); Koji Ichikawa, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 14/964,842

(22) Filed: Dec. 10, 2015

(65) Prior Publication Data

US 2016/0170298 A1    Jun. 16, 2016

(30) Foreign Application Priority Data

Dec. 15, 2014    (JP) .................................. 2014-252629

(51) Int. Cl.

| | | |
|---|---|---|
| *G03F 7/004* | (2006.01) |
| *G03F 7/039* | (2006.01) |
| *G03F 7/20* | (2006.01) |
| *G03F 7/30* | (2006.01) |
| *G03F 7/32* | (2006.01) |
| *C07D 317/72* | (2006.01) |
| *C07D 321/12* | (2006.01) |
| *C07C 381/12* | (2006.01) |
| *C07C 309/06* | (2006.01) |
| *C07C 309/17* | (2006.01) |
| *C07D 327/06* | (2006.01) |

(52) U.S. Cl.
CPC .......... *G03F 7/0045* (2013.01); *C07C 309/06* (2013.01); *C07C 309/17* (2013.01); *C07C 381/12* (2013.01); *C07D 317/72* (2013.01); *C07D 321/12* (2013.01); *C07D 327/06* (2013.01); *G03F 7/0046* (2013.01); *G03F 7/0397* (2013.01); *G03F 7/2041* (2013.01); *G03F 7/30* (2013.01); *G03F 7/32* (2013.01); *G03F 7/322* (2013.01); *G03F 7/325* (2013.01); *C07C 2101/14* (2013.01); *C07C 2101/16* (2013.01); *C07C 2103/74* (2013.01); *C07C 2103/97* (2013.01); *C07C 2103/98* (2013.01)

(58) Field of Classification Search
None
See application file for complete search history.

(56) References Cited

U.S. PATENT DOCUMENTS

| | | | |
|---|---|---|---|
| 2009/0162788 A1 | 6/2009 | Hada et al. | |
| 2009/0226842 A1* | 9/2009 | Shimizu | G03F 7/0045 430/281.1 |
| 2010/0316952 A1 | 12/2010 | Ichikawa et al. | |
| 2012/0122032 A1 | 5/2012 | Anryu et al. | |
| 2013/0040239 A1* | 2/2013 | Ichikawa | C07C 309/17 430/285.1 |

FOREIGN PATENT DOCUMENTS

JP    2009-167156 A    7/2009

* cited by examiner

*Primary Examiner* — Sin Lee
(74) *Attorney, Agent, or Firm* — Birch, Stewart, Kolasch & Birch, LLP

(57) ABSTRACT

A salt represented by the formula (I):

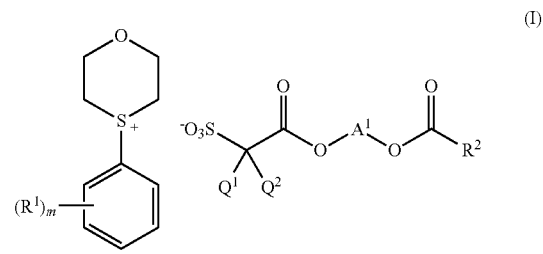

(I)

wherein $Q^1$ and $Q^2$ each independently represent a fluorine atom or a $C_1$ to $C_6$ perfluoroalkyl group;

$R^1$ represents a $C_1$ to $C_{12}$ alkyl group in which a methylene group may be replaced by an oxygen atom or a carbonyl group;

$A^1$ represents a $C_2$ to $C_8$ alkanediyl group; and $R^2$ represents a $C_5$ to $C_{18}$ alicyclic hydrocarbon group in which a hydrogen atom may be replaced by a hydroxy group, and in which a methylene group may be replaced by an oxygen atom or a carbonyl group, and which alicyclic hydrocarbon group may have a cyclic ketal structure optionally having a fluorine atom; and "m" represents an integer of 0, 1, 2 or 3.

7 Claims, No Drawings

SALT, ACID GENERATOR, PHOTORESIST COMPOSITION, AND METHOD FOR PRODUCING PHOTORESIST PATTERN

This nonprovisional application claims priority under 35 U.S.C. §119(a) on Patent Application No. 2014-252629 filed in JAPAN on Dec. 15, 2014, the entire contents of which are hereby incorporated by reference.

TECHNICAL FIELD

The present invention relates to a salt, and an acid generator, a photoresist composition, and a method for producing a photoresist pattern.

BACKGROUND ART

In production of semiconductor integrated circuits, ion implantation using photoresist patterns is sometimes conducted in order to dope impurities on substrates of semiconductors.

US2010/316952A discloses a salt represented by the following formula:

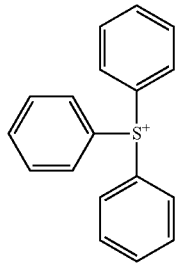

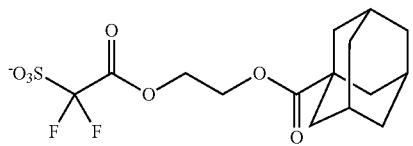

and a photoresist composition which contains the salt as an acid generator.

US2012/122032A1 discloses a salt represented by the following formula:

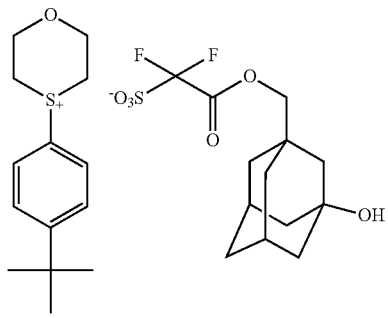

and a photoresist composition which contains the salt as an acid generator.

SUMMARY

The present invention relates to the followings.

[1] A salt represented by the formula (I):

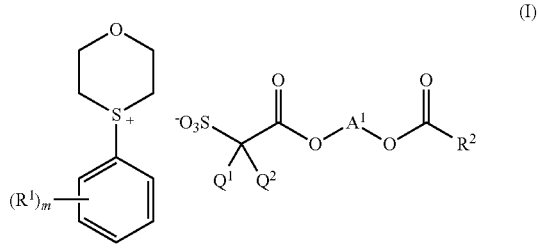

wherein $Q^1$ and $Q^2$ each independently represent a fluorine atom or a $C_1$ to $C_6$ perfluoroalkyl group;

$R^1$ represents a $C_1$ to $C_{12}$ alkyl group in which a methylene group may be replaced by an oxygen atom or a carbonyl group;

$A^1$ represents a $C_2$ to $C_8$ alkanediyl group; and $R^2$ represents a $C_5$ to $C_{18}$ alicyclic hydrocarbon group in which a hydrogen atom may be replaced by a hydroxy group, and in which a methylene group may be replaced by an oxygen atom or a carbonyl group, and which alicyclic hydrocarbon group may have a cyclic ketal structure optionally having a fluorine atom; and "m" represents an integer of 0, 1, 2 or 3.

[2] The salt according to [1] wherein the alicyclic hydrocarbon group for $R^2$ is an adamantyl group.

[3] The salt according to [1] or [2] wherein $R^1$ represents a $C_1$ to $C_6$ alkyl group.

[4] An acid generator which contains the salt according to any one of [1] to [3].

[5] A photoresist composition which contains the salt represented by the formula (I) and a resin having an acid-labile group.

[6] The photoresist composition according to [5], which further contains a salt which generates an acid weaker in acidity than an acid generated from the salt represented by the formula (I).

[7] A process for producing a photoresist pattern comprising the following steps (1) to (5):

(1) a step of applying the photoresist composition according [5] or [6] on a substrate, (2) a step of forming a composition film by conducting drying, (3) a step of exposing the composition film to radiation, (4) a step of baking the exposed composition film, and (5) a step of developing the baked composition film.

DESCRIPTION OF PREFERRED EMBODIMENTS

Herein, the term "(meth)acrylic monomer" means a monomer having a structure of "$CH_2$=CH—CO—" or "$CH_2$=C($CH_3$)—CO—", as well as "(meth)acrylate" and "(meth)acrylic acid" mean "an acrylate or methacrylate" and "an acrylic acid or methacrylic acid," respectively.

Herein, chain structure groups include those having a linear structure and those having a branched structure.

Unless otherwise specified, the term "aliphatic hydrocarbon group" means a chain aliphatic hydrocarbon group.

The indefinite articles "a" and "an" are taken as the same meaning as "one or more".

The term "solid components" means components other than solvents in a resist composition.

The salt represented by formula (I) is sometimes referred to as "Salt (I)", the cation contained in formula (I) is sometimes referred to as "Cation (I)", and the anion contained in formula (I) is sometimes referred to as "Anion (I)".

<Salt (I)>

Salt (I) is represented by formula (I).

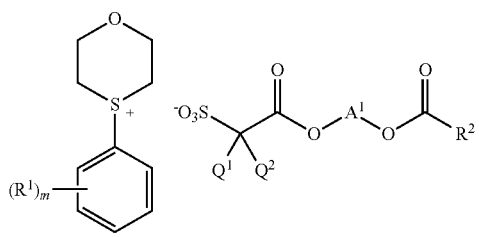

(I)

In formula (I), $Q^1$ and $Q^2$ each independently represent a fluorine atom or a $C_1$ to $C_6$ perfluoroalkyl group;

$R^1$ represents a $C_1$ to $C_{12}$ alkyl group in which a methylene group may be replaced by an oxygen atom or a carbonyl group;

$A^1$ represents a $C_2$ to $C_8$ alkanediyl group; and $R^2$ represents a $C_5$ to $C_{18}$ alicyclic hydrocarbon group in which a hydrogen atom may be replaced by a hydroxy group, and in which a methylene group may be replaced by an oxygen atom or a carbonyl group, and which alicyclic hydrocarbon group may have a cyclic ketal structure optionally having a fluorine atom; and "m" represents an integer of 0, 1, 2 or 3.

Examples of the alkyl group represented by $R^1$ include a methyl group, an ethyl group, n-propyl group, an isopropyl group, a n-butyl group, a sec-butyl group, a tert-butyl group, a pentyl group, a hexyl group, a heptyl group, a 2-ethylhexyl group, an octyl group, a nonyl group, an undecyl group and a decyl group.

$R^1$ is preferably a $C_1$ to $C_6$ alkyl group, more preferably a $C_1$ to $C_4$ alkyl group such as a methyl group, an ethyl group, n-propyl group, an isopropyl group, and tert-butyl group, and still more preferably a methyl group and tert-butyl group.

For $R^1$, examples of the alkyl group in which a methylene group has been replaced by an oxygen atom or a carbonyl group include a methoxy group, an ethoxy group, a butoxy group, a hexyloxy group, methoxyethyl group, an ethoxyethyl group, an ethoxyethoxy groups, ethoxyethoxyethoxy group, an ethoxyethoxyethoxyethoxy group, an ethoxyethoxyethoxyethoxyethoxy group, an acetyl group, a methoxycarbonyl group, an acetyloxy group, and a butoxycarbonyloxy group.

"m" represents an integer of 0, 1, 2 or 3, preferably an integer of 1 or 2, and still more preferably 1.

Examples of the perfluoroalkyl group for $Q^1$ and $Q^2$ include trifluoromethyl, perfluoroethyl, perfluoropropyl, perfluoroisopropyl, perfluorobutyl, perfluoro-sec-butyl, perfluoro-tert-butyl, perfluoropentyl and perfluorohexyl groups.

$Q^1$ and $Q^2$ each independently are preferably a trifluoromethyl group or a fluorine atom, and both of $Q^1$ and $Q^2$ are more preferably a fluorine atom.

For $A^1$, examples of the alkanediyl groups include linear alkanediyl groups such as an ethylene group, a propane-1,3-diyl group, a butane-1,4-diyl group, a pentane-1,5-diyl group, a hexane-1,6-diyl group, a heptane-1,7-diyl group, an octane-1,8-diyl group; and branched alkanediyl groups such as an ethane-1,1-diyl group, a propane-1,1-diyl group, a propane-1,2-diyl group, a propane-2,2-diyl group, a pentane-2,4-diyl group, a 2-methyl propane-1,3-diyl group, a 2-methyl propane-1,2-diyl group, a pentane-1,4-diyl group, and a 2-methyl butane-1,4-diyl group. $A^1$ is preferably a $C_2$ to $C_6$ alkanediyl group, more preferably a $C_2$ to $C_4$ alkanediyl group.

The alicyclic hydrocarbon group represented by $R^2$ may be monocyclic or polycyclic.

Examples of the alicyclic hydrocarbon group include a monocyclic alicyclic hydrocarbon group such as a $C_3$-$C_{18}$ cycloalkyl group (e.g. a cyclopentyl group, a cyclohexyl group, a cycloheptyl group and a cyclooctyl group) and a polycyclic alicyclic hydrocarbon group such as a decahydronaphthyl group, an adamantyl group, a norbornyl group, specifically a cyclopentyl group, a cyclohexyl group, a cycloheptyl group, a norbornyl group, and an adamantyl group, preferably a cyclopentyl group, a cyclohexyl group and an adamantyl group, more preferably a cyclohexyl group and an adamantyl group, and still more preferably an adamantyl group.

The alicyclic hydrocarbon group represented by $R^2$ may have a cyclic ketal structure optionally having a fluorine atom.

The cyclic ketal structure is formed by replacing two hydrogen atoms contained in the alicyclic hydrocarbon group respectively by oxygen atoms each bonded to one $C_1$ to $C_8$ alkanediyl group, which has the structure represented by —O—[$C_1$-$C_8$ alkanediyl group]-O—.

Examples of the cyclic ketal structure include the rings having a structure selected from among —O—(CH$_2$)$_2$—O—, —O—(CH$_2$)$_3$—O—, —O—(CH$_2$)$_4$—O—, —O—CH$_2$—(CF$_2$)$_2$—CH$_2$—O—, —O—CH$_2$—(CF$_2$)$_3$—CH$_2$—O— and —O—CH$_2$—(CF$_2$)$_4$—CH$_2$—O—, preferably —O—CH$_2$—(CF$_2$)$_2$—CH$_2$—O—, —O—CH$_2$—(CF$_2$)$_3$—CH$_2$—O— and —O—CH$_2$—(CF$_2$)$_4$—CH$_2$—O—, more preferably —O—CH$_2$—(CF$_2$)$_2$—CH$_2$—O— and —O—CH$_2$—(CF$_2$)$_3$—CH$_2$—O—, and still more preferably —O—CH$_2$—(CF$_2$)$_2$—CH$_2$—O—.

Examples of the alkanediyl group which the cyclic ketal structure has include the same ones as that of $A^1$.

Examples of the anion (I) include those represented by the following formulae, preferably those represented by the formulae (Ia-1) to (Ia-4) and (Ia-6), and more preferably those represented by the formulae (Ia-1) to (Ia-4).

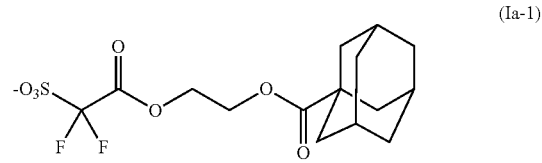

(Ia-1)

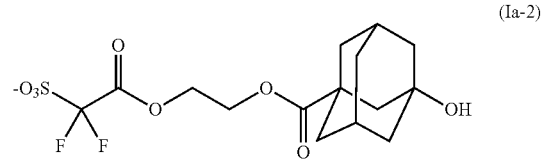

(Ia-2)

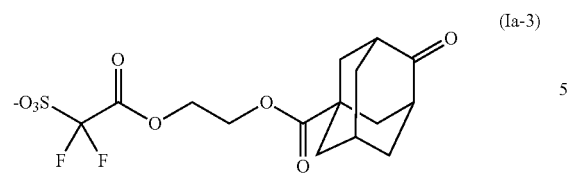 (Ia-3)
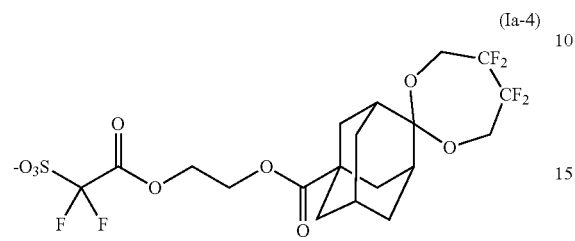 (Ia-4)
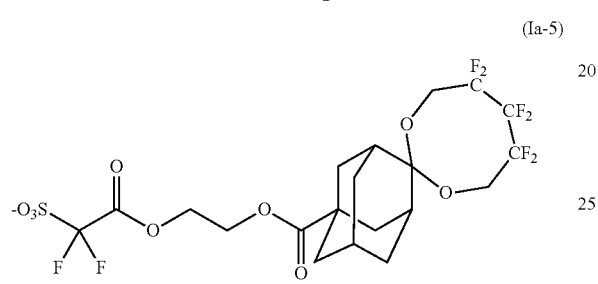 (Ia-5)
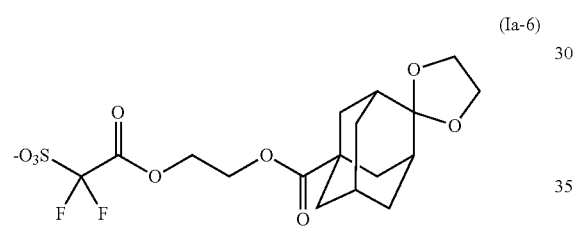 (Ia-6)
Examples of Cation (I) include the following ones, preferably those represented by the formulae (c-1) to (c-3) and (c-5).
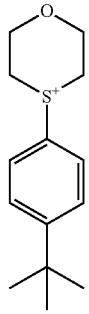 (c-1)
(c-2)
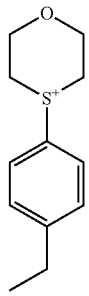
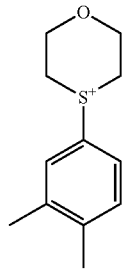 (c-3)
(c-4)
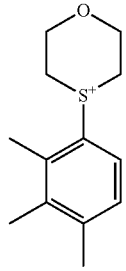 (c-5)
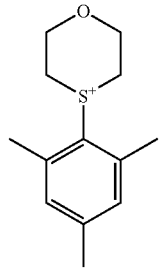 (c-6)
(c-7)

(c-8)
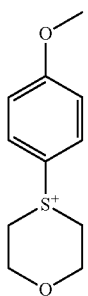
(c-9)
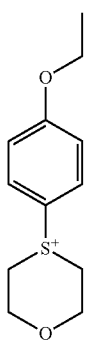
(c-10)
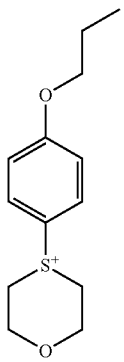
(c-11)
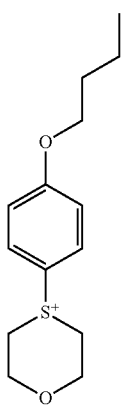
(c-12)
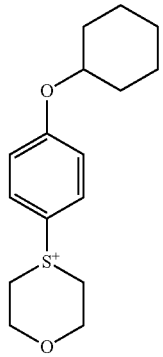
(c-13)
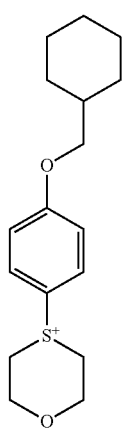
(c-14)
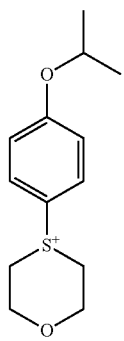
(c-15)
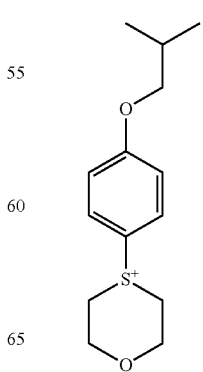

(c-16)
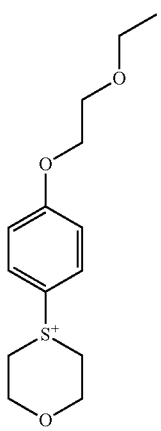
(c-17)
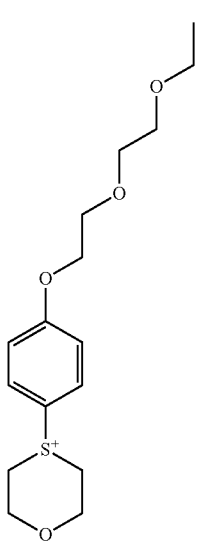
(c-18)
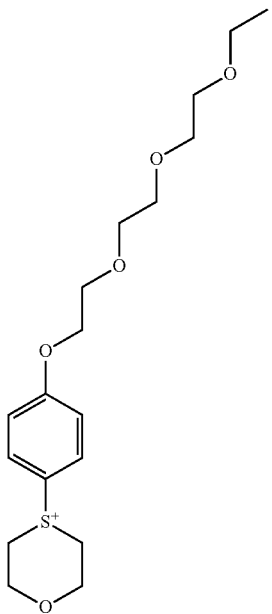
(c-19)
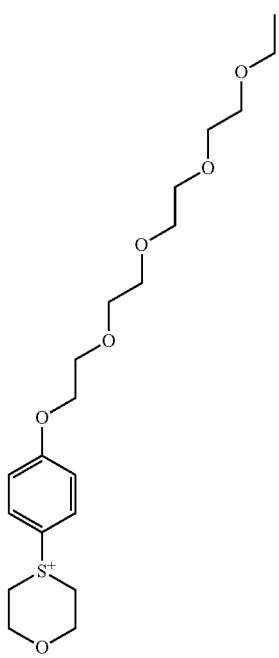
Specific examples of the Salt (I) include those consisting of an anion represented by one of formulae (Ia-1) to (Ia-6) and a cation represented by one of formulae (c-1) to (c-19), preferably those represented by formulae (I-1) to (I-20).
(I-1)
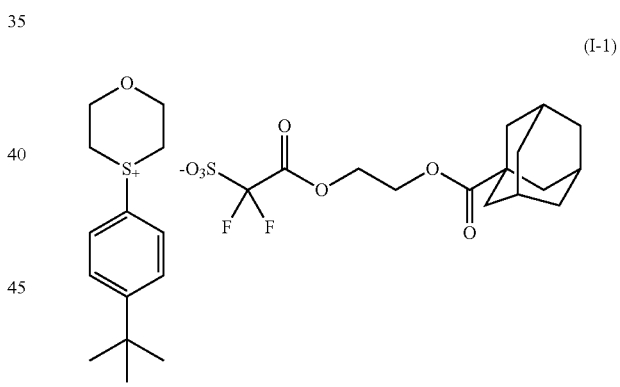
(I-2)
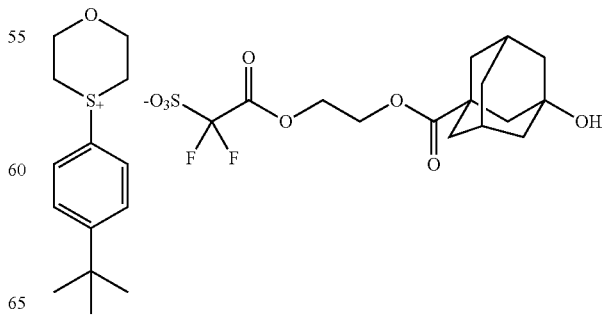

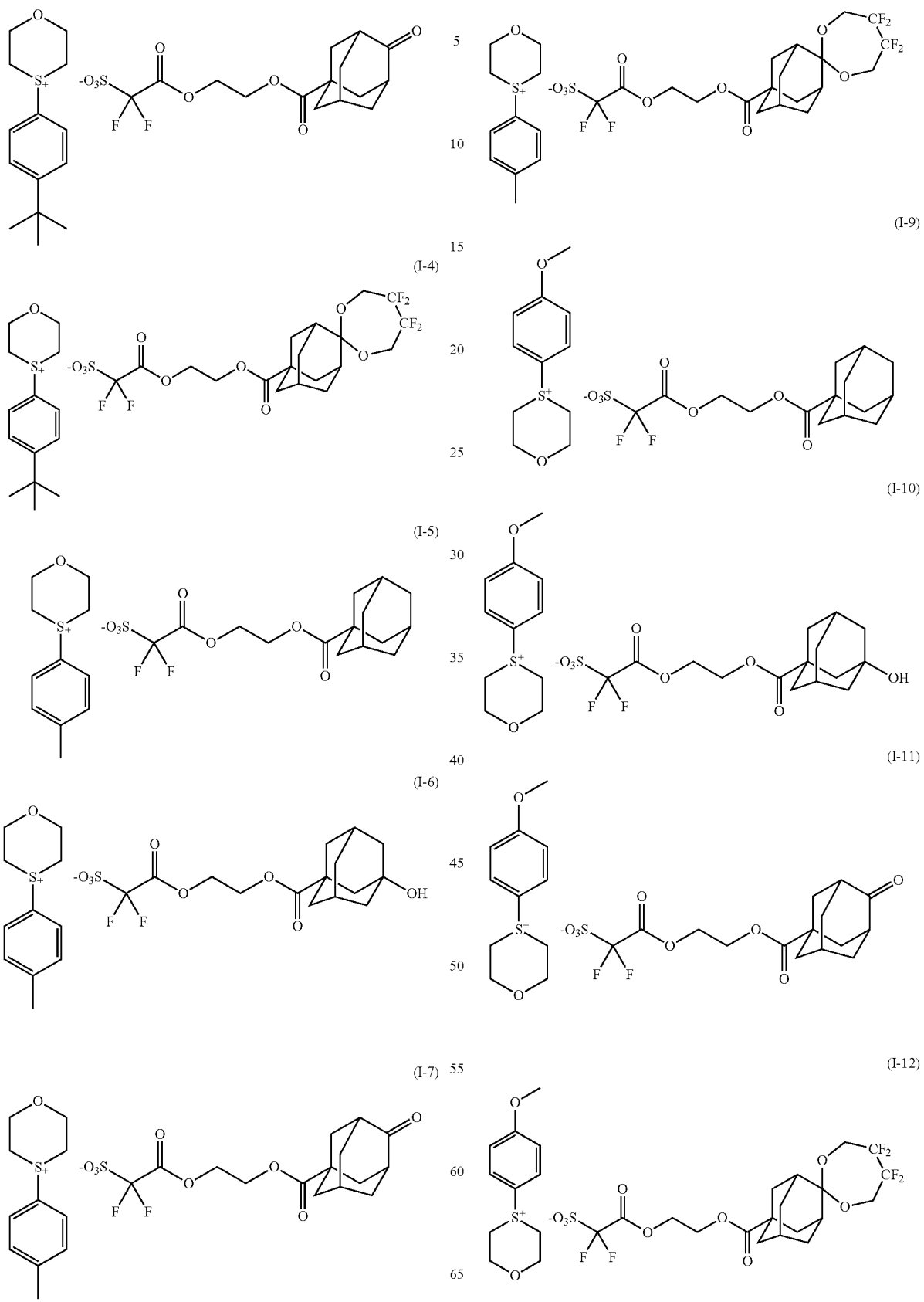

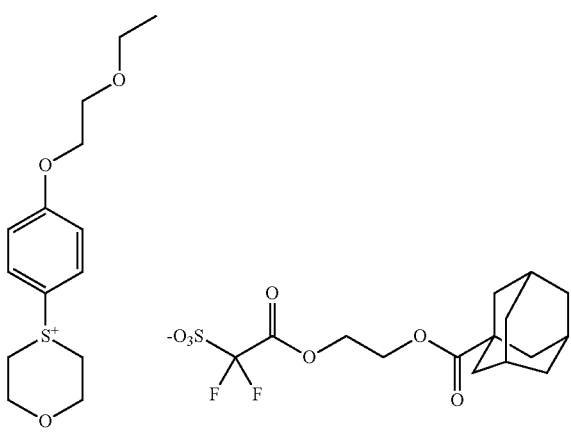
(I-13)
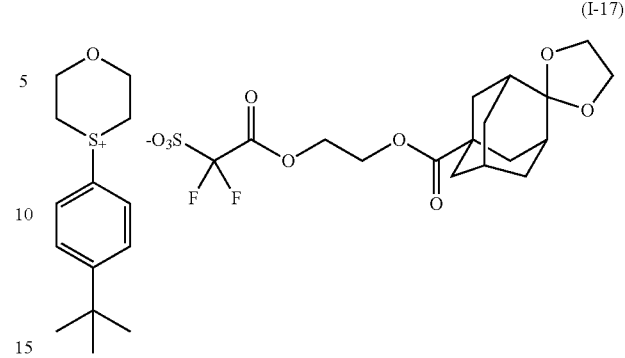
(I-17)
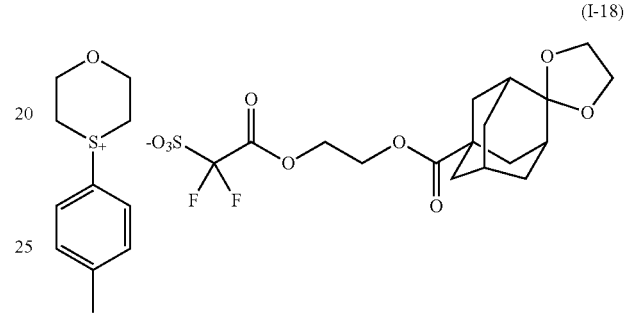
(I-18)
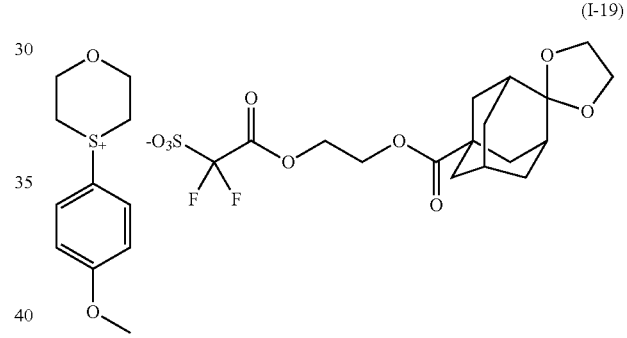
(I-19)
(I-14)
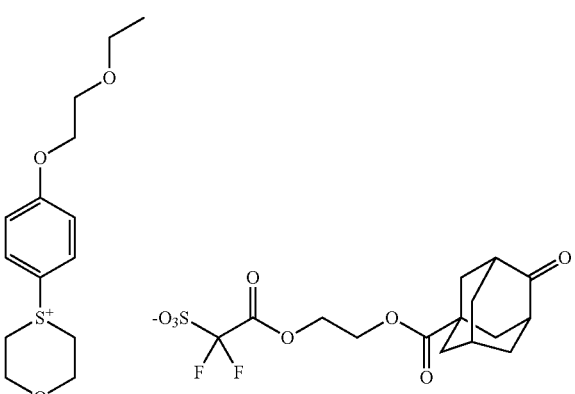
(I-15)
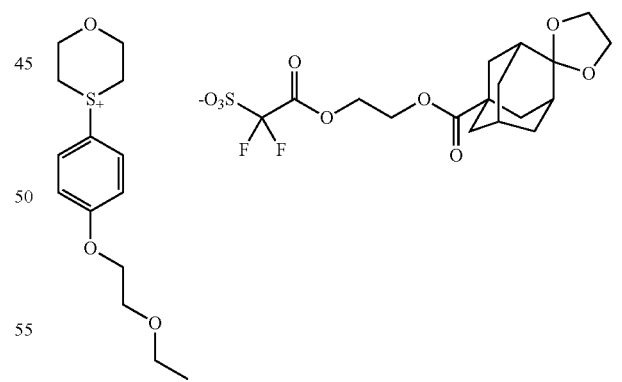
(I-20)
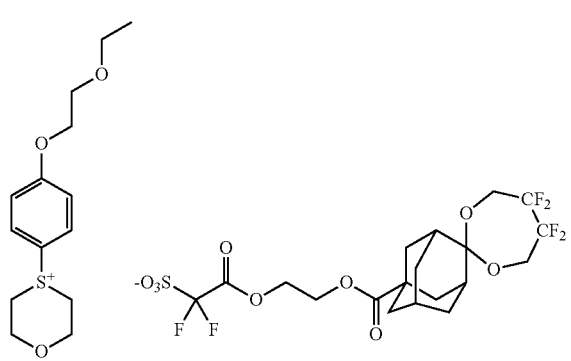
(I-16)
Among them, the salts represented by formulae (I-1) to (I-8), (I-17) and (I-18) are preferred, and the salts represented by formulae (I-1) to (I-4) and (I-17) are more preferred.
Salt (I) can be produced by reacting a salt represented by formula (I-a) with a compound represented by formula (I-b) in a solvent such as acetonitrile, chloroform or water:

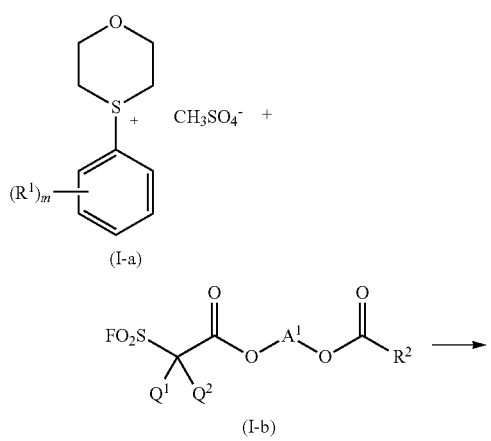

(I-a)

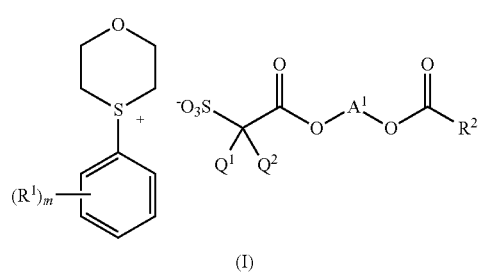

(I-b)

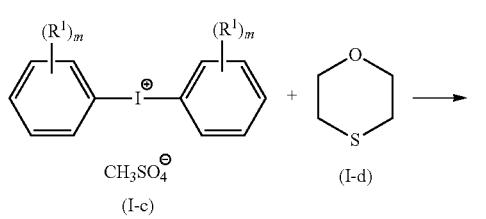

(I)

wherein $R^1$, $R^2$, $Q^1$, $Q^2$, $A^1$ and m are as defined above.

The reaction can be conducted at temperature of preferably −5° C. to 40° C., for 0.5 to 24 hours.

The salt represented by formula (I-a) can be produced by reacting a salt represented by formula (I-c) with a compound represented by formula (I-d), in the presence of a catalyst such as copper (II) acetate, in a solvent such as chloroform:

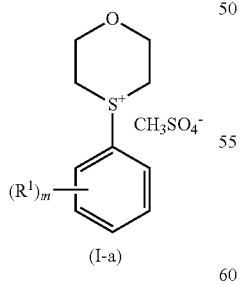

(I-c)                 (I-d)

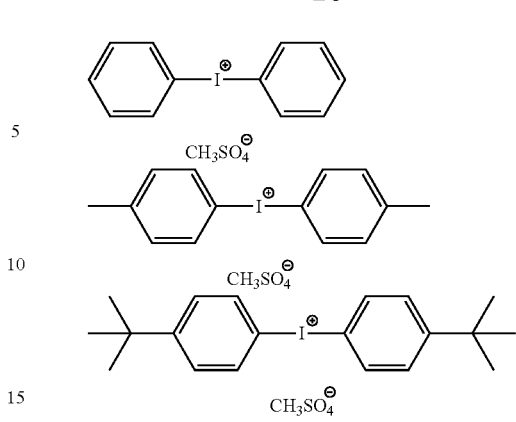

wherein $R^1$ and m are as defined above.

The reaction can be conducted at temperature of preferably 15° C. to 120° C., for 0.5 to 12 hours.

Examples of the salt represented by formula (I-c) include the following ones which are available on the market.

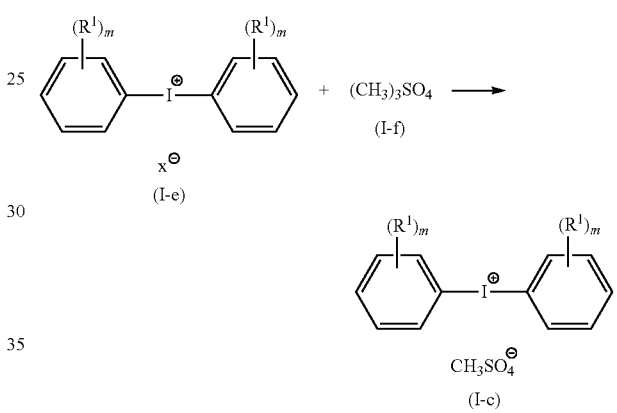

The salt represented by formula (I-c) can be produced by reacting a salt represented by formula (I-e) with a compound represented by formula (I-f) in a solvent such as chloroform:

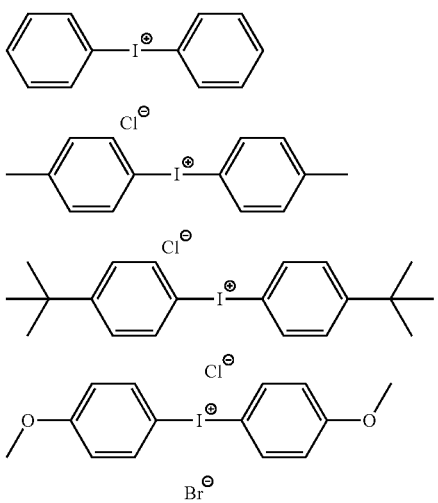

wherein $R^1$ and m are as defined above, and X represents a chlorine atom, a bromine atom or an iodine atom.

The reaction can be conducted at temperature of preferably 15° C. to 80° C., for 0.5 to 24 hours.

Examples of the salt represented by formula (I-e) include the following ones which are available on the market.

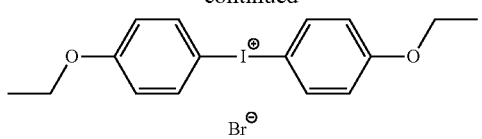

The compound represented by formula (I-b) can be produced by reacting a compound represented by formula (I-g) with a compound represented by formula (I-h), in the presence of a catalyst, in a solvent such as acetonitrile or chloroform:

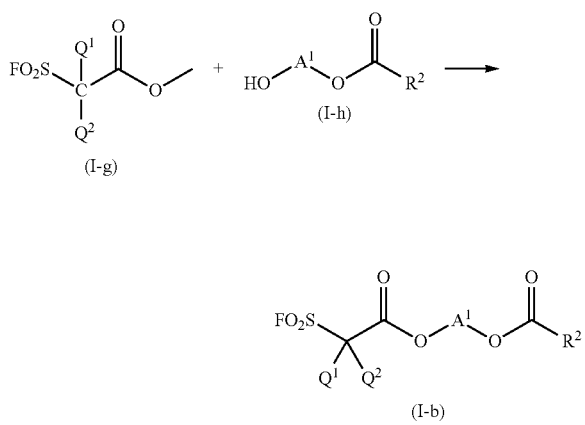

wherein $R^2$, $Q^1$, $Q^2$ and $A^1$ are as defined above.

The reaction can be conducted at temperature of preferably 15° C. to 120° C., for 0.5 to 12 hours.

Examples of the catalyst for the reaction include the following compound.

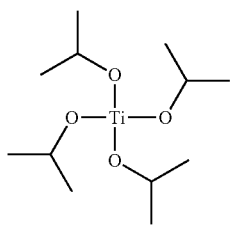

Examples of the compound represented by formula (I-g) include the following compound which is available on the market.

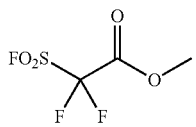

The compound represented by formula (I-h) can be produced by reacting a compound represented by formula (I-i) with a compound represented by formula (I-j), in the presence of a catalyst such as carbonyldiimidazole, in a solvent such as acetonitrile or chloroform:

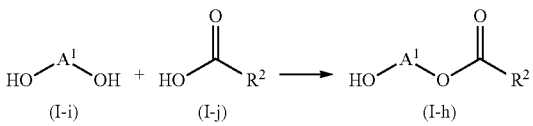

wherein $A^1$ and $R^2$ are as defined above.

Examples of the compound represented by formula (I-i) include the following compound which is available on the market.

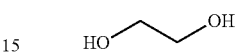

Examples of the compound represented by formula (I-j) include the following compounds which are available on the market.

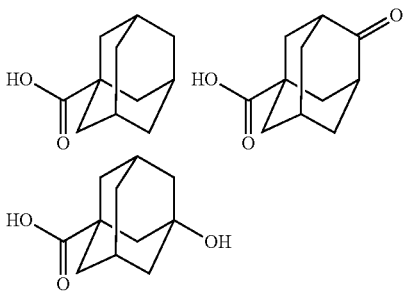

The salt (I) in which $R^2$ is an alicyclic hydrocarbon group having a cyclic ketal structure can be produced by reacting the salt (I) having an oxoadamantyl group as the group represented by $R^2$ with diol in the presence of an acid such as p-toluenesulfonic acid.

The reaction with an acid can be conducted at temperature of preferably 15° C. to 100° C., for 0.5 to 12 hours. Examples of diol include ethylene glycol, propane-1,3-diol, butane-1,4-diol and fluorobutane-1,4-diol.

<Acid Generator>

The acid generator of the disclosure contains a Salt (I). The acid generator of the disclosure may contain two or more kinds of Salts (I).

Here, the acid generator means salts capable of generating an acid with a developer described later.

The acid generator may further contain one or more known acid generators in the art of the photoresist compositions.

The known acid generators, which are sometimes referred to as "acid generator (B)", are described in detail later.

When the acid generator further contains an acid generator (B), the amount ratio of the Salt (I) and the acid generator (B) [the Salt (I): the acid generator (B), weight ratio] is usually 1:99 to 99:1, preferably 2:98 to 98:2, more preferably 5:95 to 95:5, still more preferably 90:10 to 60:40, and further still more preferably 85:15 to 70:30.

<Photoresist Composition>

The photoresist composition of the disclosure contains a Salt (I) and a resin having an acid-labile group which resin is sometimes referred to as "Resin (A)".

The photoresist composition may further contain an acid generator (B), a quencher, or a solvent.

The photoresist composition preferably further contains a quencher, or a solvent, more preferably both of them.

In the photoresist composition, the content of Salt (I) is usually 1 part by mass or more, preferably 2 parts by mass or more, per 100 parts by mass of the resin (A). The content of t Salt (I) is usually 20 parts by mass or less, preferably 15 parts by mass or less, per 100 parts by mass of the resin (A).

<Acid Generator (B)>

The acid generator (B) may be any of an ionic acid generator and a non-ionic acid generator, and preferably an ionic acid generator.

Examples of the acid generator include a salt such as an organic sulfonium salt, an organic sulfonic acid salt, and acid generators as mentioned in JP2013-68914A1, JP2013-3155A1 and JP2013-11905A1.

Specific examples of the acid generator include the following salts represented by the formulae (B1-1) to (B1-30). Among them, those which contain an arylsulfonium cation are preferred, the salts represented by the formulae (B1-1), (B1-2), (B1-3), (B1-6), (B1-7), (B1-11), (B1-12), (B1-13), (B1-14), (B1-20), (B1-21), (B1-22), (B1-23), (B1-24), (B1-25), (B1-26) and (B1-29) are more preferred, and the salts represented by the formulae (B1-1), (B1-2), (B1-3), (B1-6), (B1-7), (B1-11), (B1-12), (B1-13), (B1-14), (B1-20), (B1-21) (B1-22), (B1-23), (B1-24), (B1-25) and (B1-26) are still more preferred.

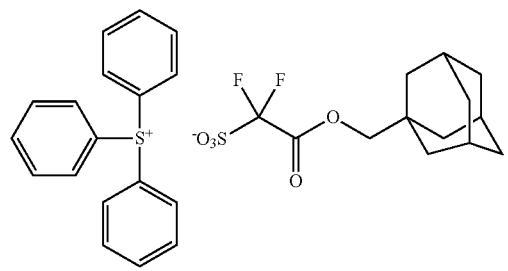

(B1-1)

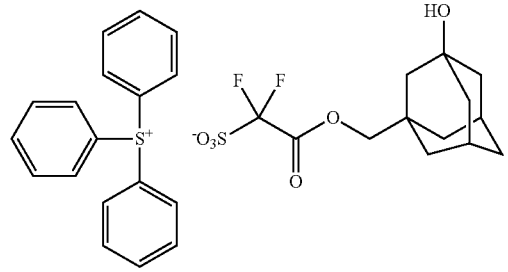

(B1-2)

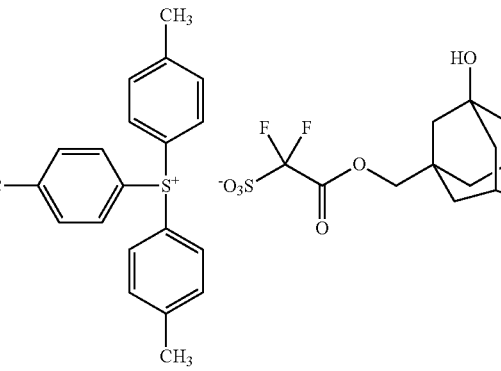

(B1-3)

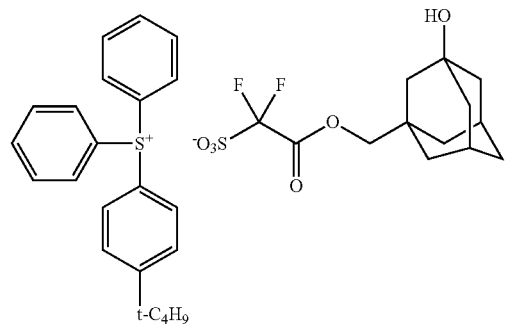

(B1-4)

(B1-5)

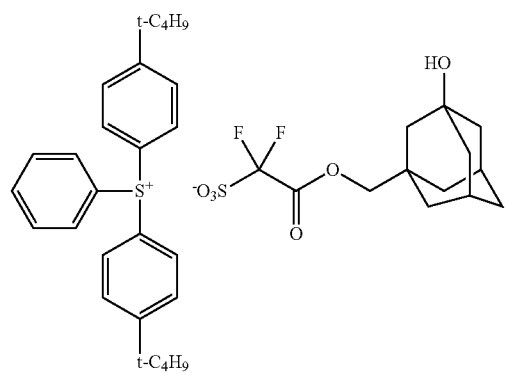

(B1-6)

(B1-7)

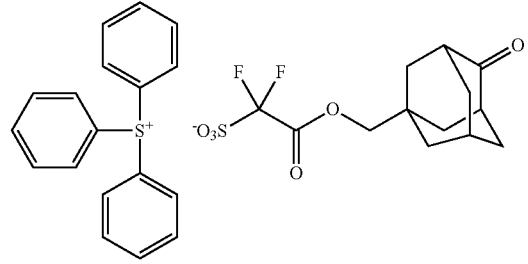

(B1-8)
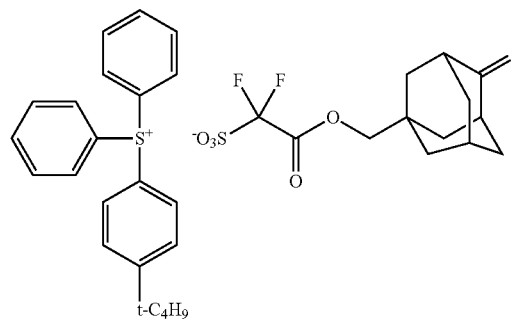
(B1-9)
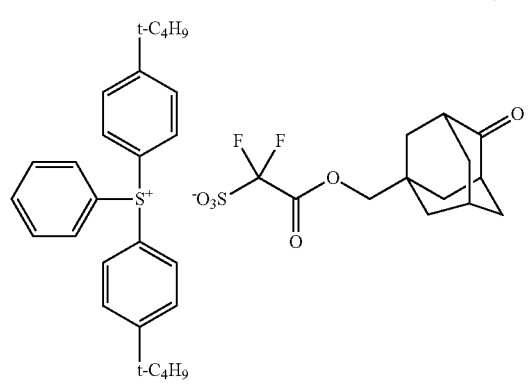
(B1-10)
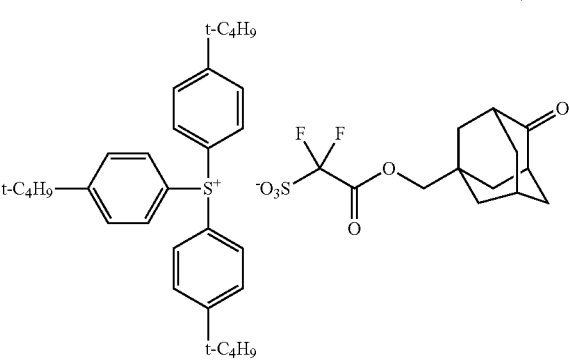
(B1-11)
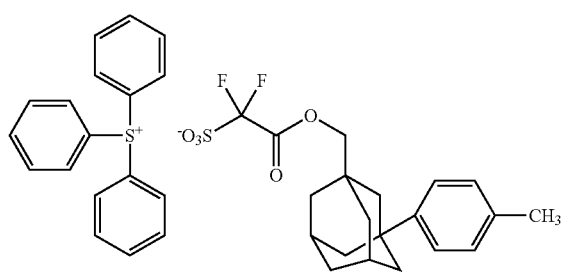
(B1-12)
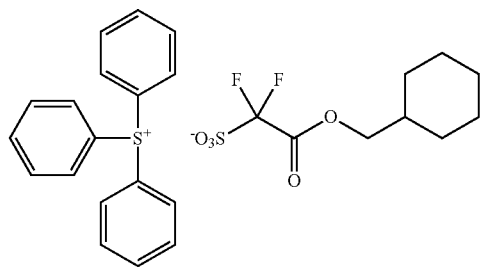
(B1-13)
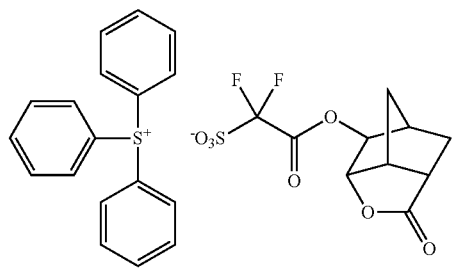
(B1-14)
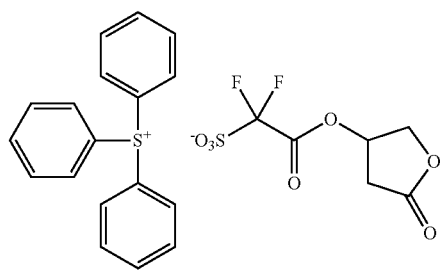
(B1-15)
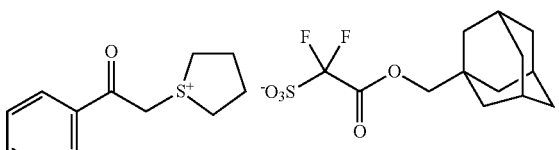
(B1-16)
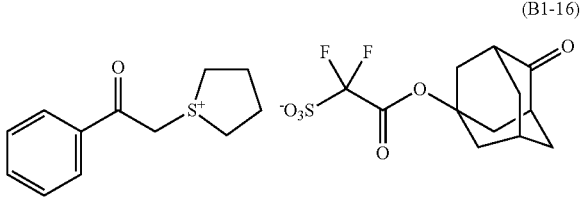
(B1-17)
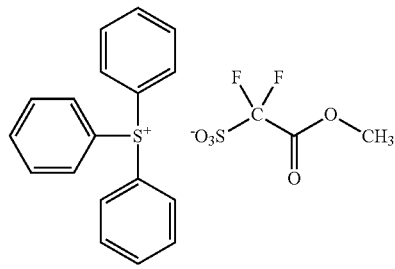

(B1-18)
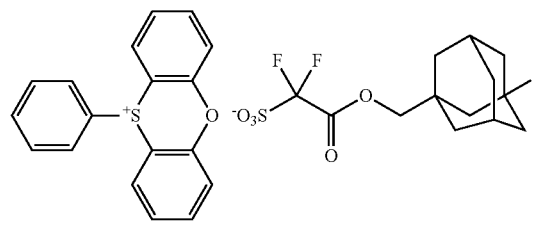
(B1-19)
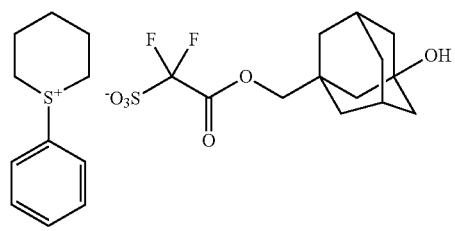
(B1-20)
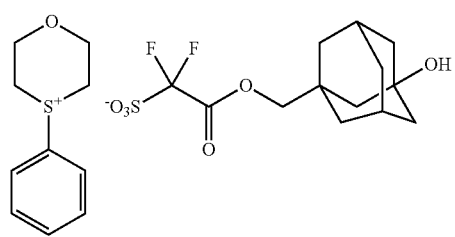
(B1-21)
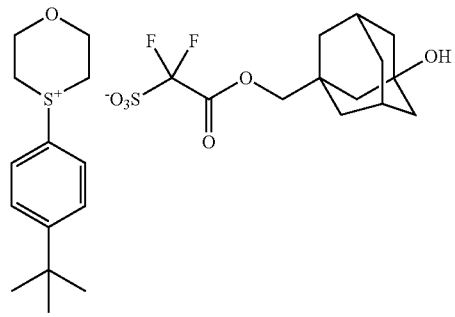
(B1-22)
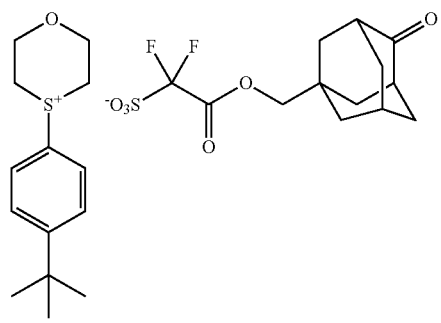
(B1-23)
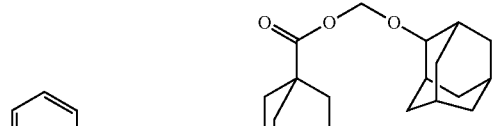
(B1-24)
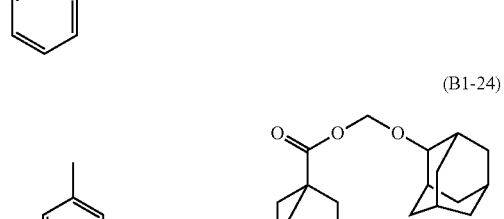
(B1-25)
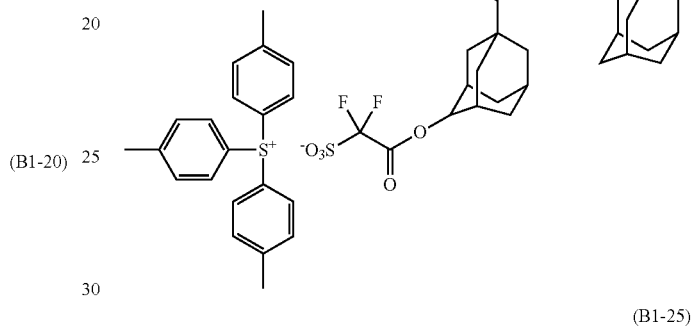
(B1-26)
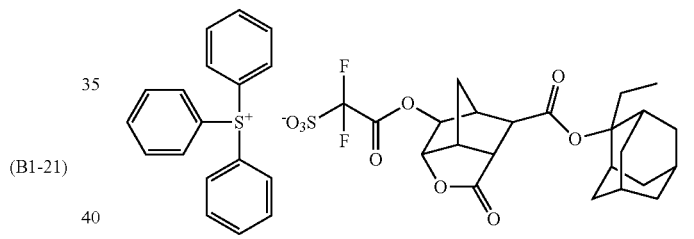
(B1-27)
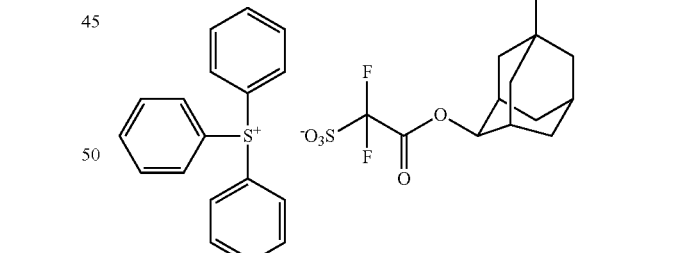

-continued (B1-28)
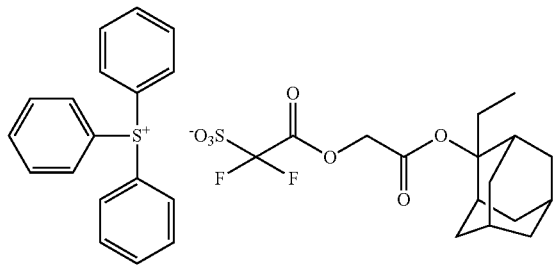

(B1-29)
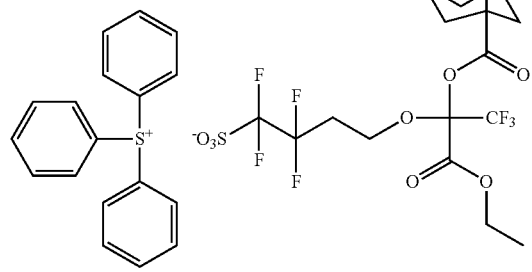

(B1-30)
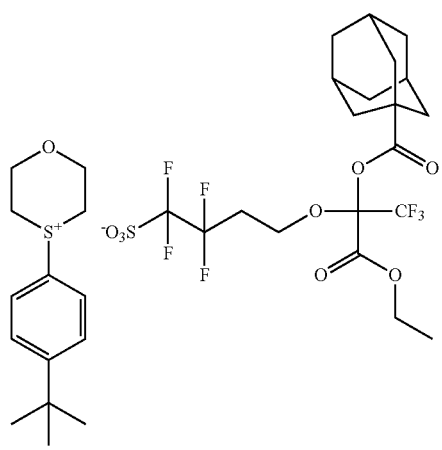

In the photoresist composition of the disclosure, the amount of the acid generator (B) is preferably 1 part by mass to 20 parts by mass, and more preferably 3 parts by mass to 15 parts by mass with respect to 100 parts by mass of the resin (A).

In the photoresist composition of the disclosure, the acid generator (B) may consist of a single salt or contain two or more of salts.

In the photoresist composition of the disclosure, when the photoresist composition contains the salt (I) and the acid generator (B), the total amount of the salt (I) and the acid generator (B) is preferably 1.5% by mass or more and more preferably 3% by mass or more, and preferably 40% by mass or less and more preferably 35% by mass or less with respect to 100 parts by mass of the resin (A).

<Resin (A)>

Resin (A) usually has a structural unit having an acid-labile group.

Hereinafter, the structural unit is sometimes referred to as "structural unit (a1)".

Preferably Resin (A) further has another structural unit than the structural unit (a1), i.e. a structural unit having no acid-labile group, which is sometimes referred to as "structural unit(s)". In this specification, "an acid-labile group" means a functional group having a leaving group which is removed therefrom by the action of an acid to thereby form a hydrophilic group, such as a hydroxyl group or a carboxy group.

Examples of the acid-labile group include
a group represented by the formula (1):

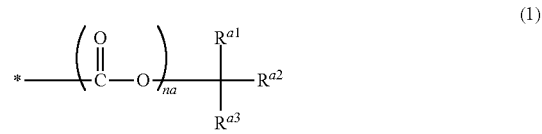

wherein $R^{a1}$, $R^{a2}$ and $R^{a3}$ independently each represent a C1-C8 alkyl group, a C3-C20 alicyclic hydrocarbon group or a group consisting of them, and $R^{a1}$ and $R^{a2}$ can be bonded each other to form a C2-C20 divalent alicyclic hydrocarbon group, "na" represents an integer of 0 or 1, and * represents a binding site; and
a group represented by the formula (2):

wherein $R^{a1'}$ and $R^{a2'}$ independently each represent a hydrogen atom or a C1-C12 hydrocarbon group, and $R^{a3'}$ represents a C1-C20 hydrocarbon group, and $R^{a2'}$ and $R^{a3'}$ can be bonded each other to form a C2-C20 divalent heterocyclic group, and one or more —CH$_2$— in the hydrocarbon group and the divalent heterocyclic group can be replaced by —O— or —S—, X represents an oxygen atom or a sulfur atom, and * represents a binding site.

For $R^{a1}$, $R^{a2}$ and $R^{a3}$, specific examples of the alkyl group include a methyl group, an ethyl group, a propyl group, an isopropyl group, a butyl group, a pentyl group, a hexyl group, a heptyl group and an octyl group.

The alicyclic hydrocarbon group may be monocyclic or polycyclic.

Examples of the alicyclic hydrocarbon group include a monocyclic alicyclic hydrocarbon group such as a C3-C20 cycloalkyl group (e.g. a cyclopentyl group, a cyclohexyl group, a cycloheptyl group and a cyclooctyl group) and a polycyclic alicyclic hydrocarbon group such as a decahydronaphthyl group, an adamantyl group, a norbornyl group, and the followings:

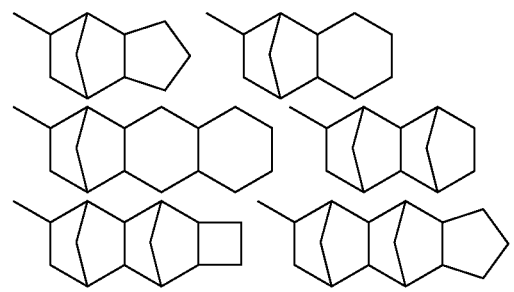

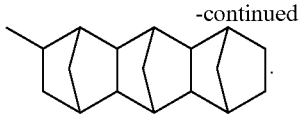

The alicyclic hydrocarbon group preferably has 3 to 16 carbon atoms.

Examples of the group consisting of alkyl and alicyclic hydrocarbon group include a methylcyclohexyl group, a dimethylcyclohexyl group, a methylnorbornyl group, an adamantylmethyl group, and a norbornylethyl group.

The "na" is preferably 0.

When the divalent alicyclic hydrocarbon group is formed by bonding $R^{a3}$ and $R^{a2}$ each other, examples of the moiety —C($R^{a1}$)($R^{a2}$)($R^{a3}$) include the following groups and the divalent hydrocarbon group preferably has 3 to 12 carbon atoms.

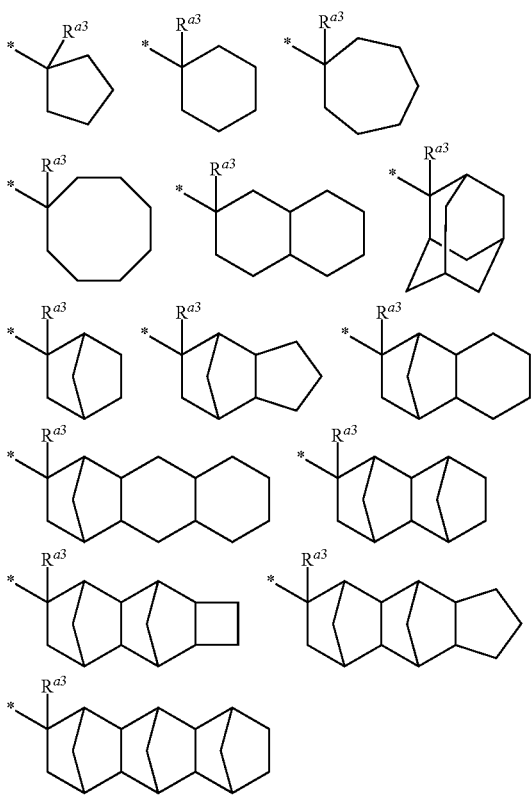

In each formula, $R^{a3}$ is the same as defined above.

Preferred are 1,1'-dialkylalkoxycarbonyl group, i.e., the group represented by the formula (1) wherein $R^{a1}$, $R^{a2}$ and $R^{a3}$ independently each represent a C1-C8 alkyl group such as a tert-butyl group;

2-alkyladamantane-2-ylxoylcarbonyl group, i.e., the group represented by the formula (1) wherein $R^{a1}$ and $R^{a2}$ are bonded each other to form an adamantyl ring and $R^{a3}$ is a C1-C8 alkyl group such as a 2-alkyl-2-adamantyl group; and 1-(adamantane-1-yl)-1-alkylalkoxycarbonyl group, i.e., the group represented by the formula (1) wherein $R^{a1}$ and $R^{a2}$ are C1-C8 alkyl groups and $R^{a3}$ is an adamantyl group.

For formula (2), examples of the hydrocarbon group include an alkyl group, an alicyclic hydrocarbon group, an aromatic hydrocarbon group and a group consisting of two or more of them.

Examples of the alkyl group and the alicyclic hydrocarbon group include the same as described above. Examples of the aromatic hydrocarbon group include an aryl group such as a phenyl group, a naphthyl group, a p-methylphenyl group, a p-tert-butylphenyl group, a p-adamantylphenyl group, a tolyl group, a xylyl group, a cumyl group, a mesityl group, a biphenyl group, an anthryl group, a phenanthryl group, a 2,6-diethylphenyl group and a 2-methyl-6-ethylphenyl group.

When the divalent hydrocarbon group is formed by bonding $R^{a2'}$ and $R^{a3'}$ each other, examples of the moiety —C($R^{a1'}$)($R^{a2'}$)($R^{a3'}$) include the following groups.

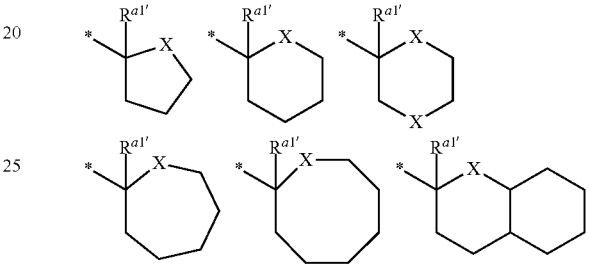

In each formula, $R^{a1'}$ and X are as defined above.

It is preferred that at least one of $R^{a1'}$ and $R^{a2'}$ is a hydrogen atom.

Examples of the group represented by the formula (2) include the following.

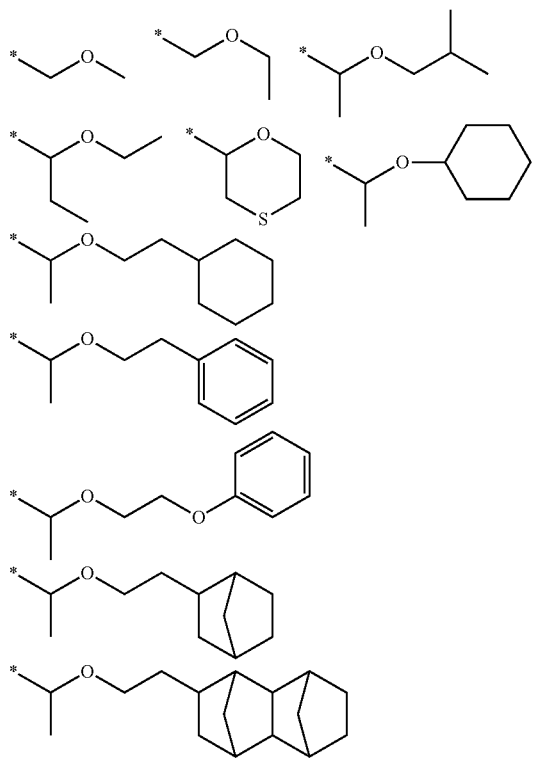

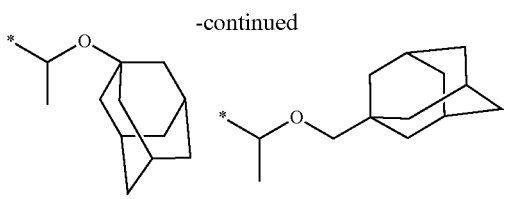

The structural unit (a1) is derived from a compound having an acid-labile group which compound is sometimes referred to as "Monomer (a1)".

Monomer (a1) is preferably a monomer having an acid-labile group and an ethylenic unsaturated group, more preferably a (meth)acrylate monomer having an acid-labile group, and still more preferably a (meth)acrylate monomer having the group represented by formula (1) or (2).

The (meth)acrylate monomer having an acid-labile group is preferably those which have a C5-C20 alicyclic hydrocarbon group.

The resin which has a structural unit derived from such monomers can provide improved resolution for a photoresist pattern to be prepared therefrom.

The structural unit derived from a (meth)acrylate monomer having the group represented by formula (1) is preferably one of structural units represented by formulae (a1-0), (a1-1) and (a1-2):

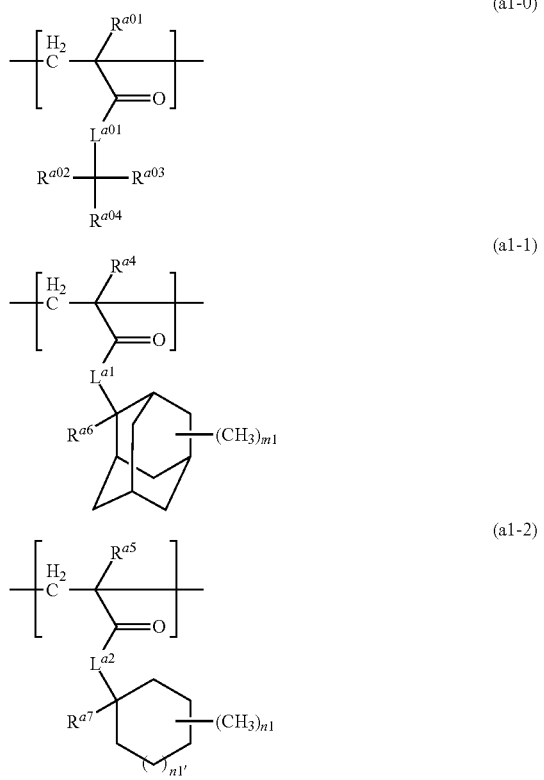

where $L^{a01}$, $L^{a1}$ and $L^{a2}$ each independently represent —O— or *—O—$(CH_2)_{k1}$—CO—O— in which k1 represents an integer of 1 to 7 and * represents a binding site to —CO—, $R^{a01}$, $R^{a4}$ and $R^{a5}$ each independently represent a hydrogen atom or a methyl group, $R^{a02}$, $R^{a03}$, $R^{a04}$, $R^{a6}$ and $R^{a7}$ each independently represent a C1-C8 alkyl group, a C3-C18 alicyclic hydrocarbon group, or a group formed by combining them, m1 represents an integer of 0 to 14, n1 represents an integer of 0 to 10, and n1' represents an integer of 0 to 3.

Hereinafter, the structural units represented by formulae (a1-0), (a1-1) and (a1-2) are respectively referred to as "structural unit (a1-0)", "structural unit (a1-1)" and "structural unit (a1-2)". Resin (A) may have two or more of these structural units.

$L^{a01}$ is preferably *—O— or *—O—$(CH_2)_{f1}$—CO—O— in which * represents a binding site to —CO—, and f1 represents an integer of 1 to 4, and is more preferably *—O— or *—O—$CH_2$—CO—O—, and is especially preferably *—O—.

$R^{a01}$ is preferably a methyl group.

For $R^{a02}$, $R^{a03}$ and $R^{a04}$, examples of the alkyl group, the alicyclic hydrocarbon group and the group formed by combining them include the same as referred for $R^{a1}$, $R^{a2}$ and $R^{a3}$.

The alkyl group preferably has 1 to 6 carbon atoms.

The alicyclic hydrocarbon group preferably has 3 to 8 carbon atoms and more preferably 3 to 6 carbon atoms. The alicyclic hydrocarbon group is preferably a saturated aliphatic cyclic hydrocarbon group.

The group formed by combining them preferably has 18 carbon atoms or less in total, examples of which include a methylcyclohexyl group, a dimethylcyclohexyl group, and a methylnorbornyl group.

Each of $R^{a02}$ and $R^{a03}$ is preferably a C1-C6 alkyl group, more preferably a methyl group and an ethyl group.

$R^{a04}$ is preferably a C1-C6 alkyl group and a C5-C12 alicyclic hydrocarbon group, more preferably a methyl group, an ethyl group, a cyclohexyl group, and an adamantyl group.

Each of $L^{a1}$ and $L^{a2}$ is preferably *—O— or *—O—$(CH_2)_{f1}$—CO—O— in which * represents a binding site to —CO—, and f1 is the same as defined above, and is more preferably *—O— or *—O—$CH_2$—CO—O—, and is especially preferably *—O—.

Each of $R^{a4}$ and $R^{a5}$ is preferably a methyl group.

For $R^{a6}$ and $R^{a7}$, examples of the alkyl group include a methyl group, an ethyl group, a propyl group, an isopropyl group, a butyl group, a tert-butyl group, a pentyl group, a heptyl group, a 2-ethylheptyl group and an octyl group.

For $R^{a6}$ and $R^{a7}$, examples of the alicyclic hydrocarbon group include a monocyclic alicyclic hydrocarbon group such as a cyclohexyl group, a methylcyclohexyl group, a dimethylcyclohexyl group, a cycloheptyl group and a methylcycloheptyl group, and a polycyclic alicyclic hydrocarbon group such as a decahydronaphthyl group, an adamantyl group, a norbornyl group, a methylnorbornyl group.

For $R^{a6}$ and $R^{a7}$, examples of the group consisting of an alkyl group and an alicyclic hydrocarbon group include an aralkyl group such as a benzyl group, and a phenethyl group.

The alkyl group represented by $R^{a6}$ and $R^{a7}$ is preferably a C1-C6 alkyl group.

The alicyclic hydrocarbon group represented by $R^{a6}$ and $R^{a7}$ is preferably a C3-C8 alicyclic hydrocarbon group, more preferably a C3-C6 alicyclic hydrocarbon group.

The "m1" is preferably an integer of 0 to 3, and is more preferably 0 or 1.

The "n1" is preferably an integer of 0 to 3, and is more preferably 0 or 1.

The "n1'" is preferably 0 or 1.

Examples of the structural unit (a1-0) include those represented by formulae (a1-0-1) to (a1-0-12), preferably those represented by formulae (a1-0-1) to (a1-0-10).
(a1-0-1)
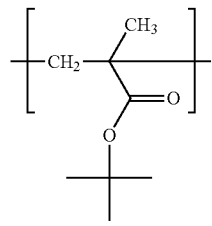
(a1-0-2)
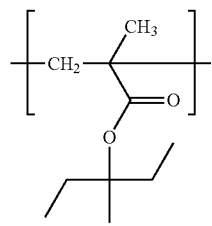
(a1-0-3)
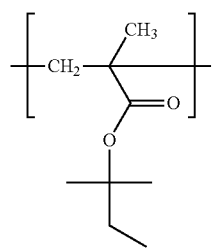
(a1-0-4)
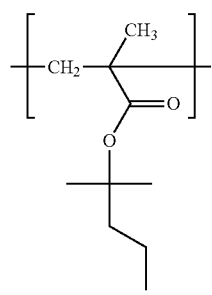
(a1-0-5)
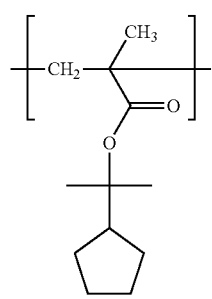
-continued
(a1-0-6)
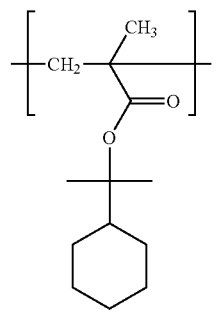
(a1-0-7)
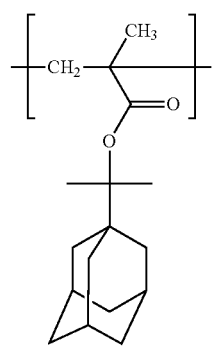
(a1-0-8)
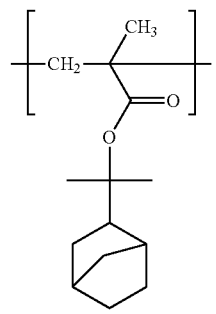
(a1-0-9)
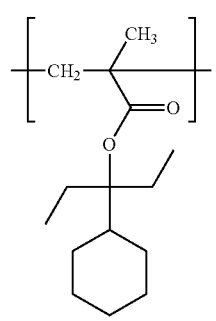
(a1-0-10)
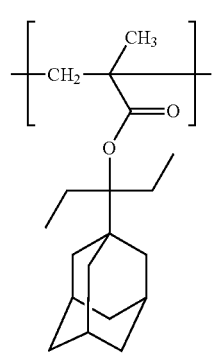

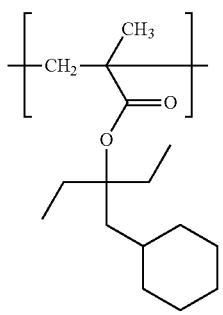
(a1-0-11)

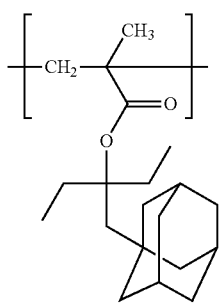
(a1-0-12)

Examples of the structural unit (a1-0) further include such groups that a methyl group has been replaced by a hydrogen atom.

Examples of the monomer from which the structural unit (a1-1) is derived include the monomers described in JP 2010-204646 A, and the following monomers represented by the formulae (a1-1-1) to (a1-1-8), preferably the following monomers represented by the formulae (a1-1-1) to (a1-1-4)

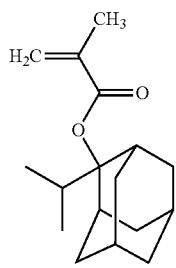
(a1-1-1)

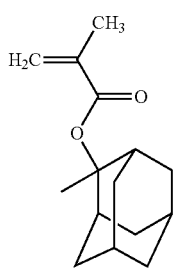
(a1-1-2)

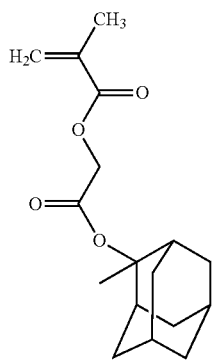
(a1-1-3)

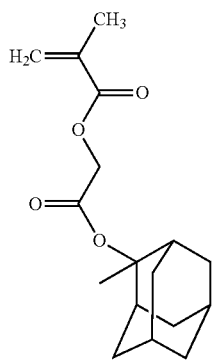
(a1-1-4)

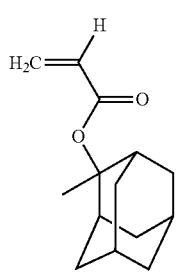
(a1-1-5)

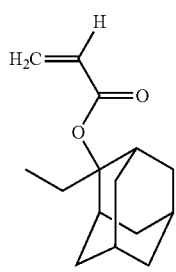
(a1-1-6)

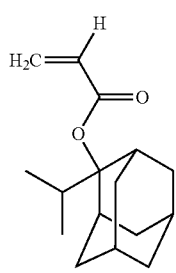
(a1-1-7)

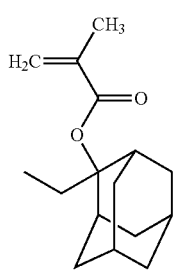

(a1-1-8)

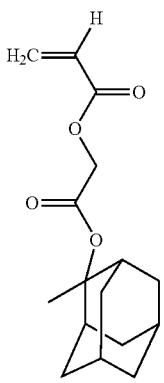

Examples of the monomer from which the structural unit (a1-2) is derived include 1-ethylcyclopentan-1-yl acrylate, 1-ethylcyclopentan-1-yl methacrylate, 1-ethylcyclohexan-1-yl acrylate, 1-ethylcyclohexan-1-yl methacrylate, 1-ethylcycloheptan-1-yl acrylate, 1-ethylcycloheptan-1-yl methacrylate, 1-methylcyclopentan-1-yl acrylate, 1-methylcyclopentan-1-yl methacrylate, 1-isopropylcyclopentan-1-yl acrylate and 1-isopropylcyclopentan-1-yl methacrylate, preferably the monomers represented by the formulae (a1-2-1) to (a1-2-12), more preferably the monomers represented by the formulae (a1-2-3), (a1-2-4), (a1-2-9) and (a1-2-10), still more preferably the monomers represented by the formulae (a1-2-3) and (a1-2-9).

(a1-2-1)
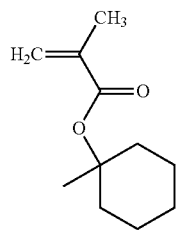

(a1-2-2)
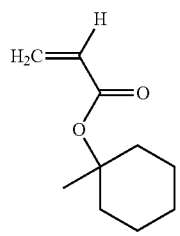

(a1-2-3)
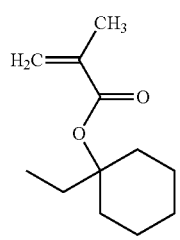

(a1-2-4)
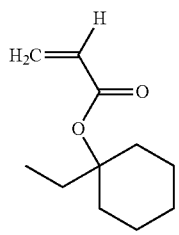

(a1-2-5)
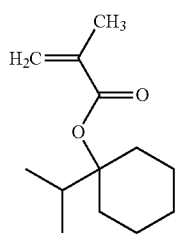

(a1-2-6)
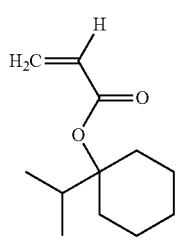

(a1-2-7)
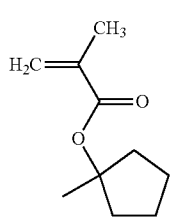

(a1-2-8)
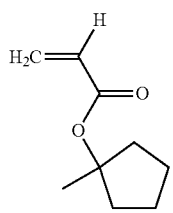

(a1-2-9)
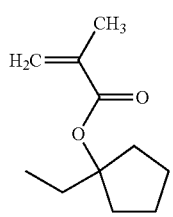

(a1-2-10)
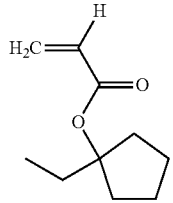

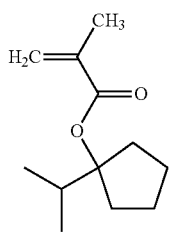

(a1-2-11)

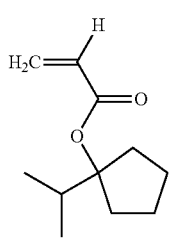

(a1-2-12)

When the resin has one or more of the structural units represented by the formulae (a1-0), (a1-1) and (a1-2), the total content of the structural units is preferably 10 to 95% by mole and more preferably 15 to 90% by mole and still more preferably 20 to 85% by mole based on all the structural units of the resin.

Other examples of the structural unit (a) having a group of formula (1) include one represented by the formula (a1-3):

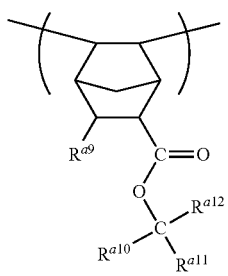

(a1-3)

wherein $R^{a9}$ represents a hydrogen atom, a carboxyl group, a cyano group, a C1-C3 aliphatic hydrocarbon group which can have a hydroxyl group, or a group represented by —COOR$^{a13}$ group in which $R^{a13}$ represents a C1-C8 aliphatic hydrocarbon group or a C3-C20 alicyclic hydrocarbon group, and a group composed of a C1-C8 aliphatic hydrocarbon group and a C3-C20 alicyclic hydrocarbon group, and the aliphatic hydrocarbon group and the alicyclic hydrocarbon group can have a hydroxyl group, and a methylene in the aliphatic hydrocarbon group and the alicyclic hydrocarbon group can be replaced by —O— or —CO—, $R^{a10}$, $R^{a11}$ and $R^{a12}$ each independently represent a C1-C8 alkyl group or a C3-C20 alicyclic hydrocarbon group, and $R^{a10}$ and $R^{a11}$ can be bonded each other to form a C3-C20 ring together with the carbon atom to which $R^{a10}$ and $R^{a11}$ are bonded, and the alkyl group and the alicyclic hydrocarbon group can have a hydroxyl group, and a methylene group in the alkyl group and the alicyclic hydrocarbon group can be replaced by —O— or —CO—.

As $R^{a9}$, examples of the alkyl group which can have a hydroxyl group include a methyl group, an ethyl group, a propyl group, a hydroxymethyl group and a 2-hydroxyethyl group.

Examples of the aliphatic hydrocarbon group represented by $R^{a13}$ include a methyl group, an ethyl group and a propyl group.

Examples of the alicylic hydrocarbon group represented by $R^{a13}$ include a cyclopropyl group, a cyclobutyl group, an adamantyl group, an adamantylmethyl group, a 1-adamantyl-1-methylethyl group, a 2-oxo-oxolan-3-yl group and a 2-oxo-oxolan-4-yl group.

Examples of the alkyl group represented by $R^{a10}$, $R^{a11}$ and $R^{a12}$ include a methyl group, an ethyl group, n-propyl group, an isopropyl group, n-butyl group, sec-butyl group, tert-butyl group, a pentyl group, a hexyl group, a heptyl group, a 2-ethylhexyl group and an octyl group.

The alicylic hydrocarbon group represented by $R^{a10}$, $R^{a11}$ and $R^{a12}$ may be a monocyclic or polycyclic group. Examples of the monocyclic alicyclic hydrocarbon group include cycloalkyl groups such as a cyclopropyl group, a cyclobutyl group, a cyclopentyl group, a cyclohexyl group, a cycloheptyl group, a cyclooctyl group and a cyclodecyl group. Examples of the polycyclic alicyclic hydrocarbon group include a hydronaphthyl group, an adamantyl group, a 2-alkyladamantane-2-yl group, a 1-(adamantane-1-yl)alkane-1-yl group, a norbornyl group, a methylnorbornyl group, and an isobornyl group.

When the divalent hydrocarbon group is formed by bonding $R^{a10}$ and $R^{a11}$, examples of —C($R^{a10}$)($R^{a11}$)($R^{a12}$) include the following ones;

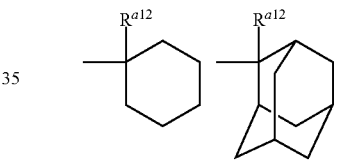

where $R^{a12}$ is as defined above.

Examples of the monomer from which the structural unit represented by the formula (a1-3) is derived include tert-butyl 5-norbornene-2-carboxylate, 1-cyclohexyl-1-methylethyl 5-norbornene-2-carboxylate, 1-methylcyclohexyl 5-norbornene-2-carboxylate, 2-methyl-2-adamantyl 5-norbornene-2-carboxylate, 2-ethyl-2-adamantyl 5-norbornene-2-carboxylate, 1-(4-methylcyclohexyl)-1-methylethyl 5-norbornene-2-carboxylate, 1-(4-hydroxylcyclohexyl)-1-methylethyl 5-norbornene-2-carboxylate, 1-methyl-1-(4-oxocyclohexyl)ethyl 5-norbornene-2-carboxylate and 1-(1-adamantyl)-1-methylethyl 5-norbornene-2-carboxylate.

When the resin has a structural unit represented by the formula (a1-3), the photoresist composition having excellent resolution and higher dry-etching resistance tends to be obtained.

When Resin (A) has the structural unit represented by the formula (a1-3), the content of the structural unit is usually 10 to 95% by mole and preferably 15 to 90% by mole and more preferably 20 to 85% by mole based on all the structural units of the resin.

Other examples of the structural unit (a) having a group of formula (2) include one represented by the formula (a1-4):

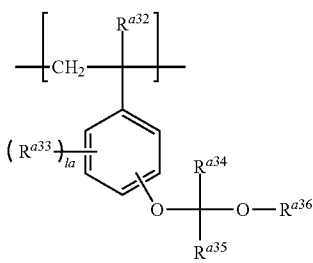

(a1-4)

wherein $R^{a32}$ represents a hydrogen atom, a halogen atom, a C1-C6 alkyl group or a C1-C6 halogenated alkyl group, $R^{a33}$ is independently in each occurrence a halogen atom, a hydroxy group, a C1-C6 alkyl group, a C1-C6 alkoxy group, a C2-C4 acyl group, a C2-C4 acyloxy group, an acryloyl group or a methacryloyl group, la represents an integer of 0 to 4, $R^{a34}$ and $R^{a35}$ each independently represent a hydrogen atom or a C1-C12 hydrocarbon group, $R^{a36}$ represents a C1-C20 hydrocarbon group in which a methylene group can be replaced by —O— or —S—, and $R^{a35}$ and $R^{a36}$ are bonded to each other to jointly represent a C2-C20 divalent hydrocarbon group in which a methylene group can be replaced by —O— or —S—.

Examples of the alkyl group represented by $R^{a32}$ and $R^{a33}$ include a methyl group, an ethyl group, a propyl group, a butyl group, a pentyl group, and a hexyl group, preferably a C1-C4 alkyl group, more preferably a methyl group and an ethyl group, and still more preferably a methyl group.

Examples of halogen atom represented by $R^{a32}$ and $R^{a33}$ include a fluorine atom, a chlorine atom, and a bromine atom.

Examples of the alkoxy group represented by $R^{a33}$ include a methoxy group, an ethoxy group, a propoxy group, an isopropoxy group, a butoxy group, an isobutoxy group, a sec-butoxy group, a tert-butoxy group, a pentyloxy group and a hexyloxy group.

Examples of the acyl group represented by $R^{a33}$ include an acetyl group, a propyonyl group and a butyryl group, and examples of the acyloxy group represented by $R^{a33}$ include an acetyloxy group, a propyonyloxy group and a butyryloxy group.

Examples of the groups represented by $R^{a34}$ and $R^{a35}$ include those as referred to for $R^{a1'}$ and $R^{a2'}$.

Examples of the groups represented by $R^{a36}$ include those as referred to for $R^{a3'}$.

$R^{a32}$ preferably represents a hydrogen atom.

$R^{a33}$ is preferably a C1-C4 alkoxy group, more preferably a methoxy group and an ethoxy group, and still more preferably a methoxy group.

The symbol "la" preferably represents 0 or 1, more preferably 1.

$R^{a34}$ preferably represents a hydrogen atom.

$R^{a35}$ is preferably a C1-C12 monovalent hydrocarbon group, more preferably a methyl group and an ethyl group.

The hydrocarbon group represented by $R^{a36}$ includes a C1-C18 alkyl group, a C3-C18 monovalent alicyclic hydrocarbon group, a C6-C18 monovalent aromatic hydrocarbon group, and any combination of them, and preferably a C1-C18 alkyl group, a C3-C18 monovalent alicyclic hydrocarbon group and a C7-C18 aralkyl group. These groups may be unsubstituted or substituted. The alkyl group and the monovalent alicyclic hydrocarbon group are preferably unsubstituted. As the substituent for the monovalent aromatic hydrocarbon group, a C6-C10 aryloxy group is preferred.

Examples of the monomer from which the structural unit represented by formula (a1-4) is derived include monomers recited in JP2010-204646A1. Among them, the monomers represented by formulae (a1-4-1), (a1-4-2), (a1-4-3), (a1-4-4), (a1-4-5), (a1-4-6), (a1-4-7) and (a1-4-8) are preferred, and the monomers represented by formulae (a1-4-1), (a1-4-2), (a1-4-3), (a1-4-4), (a1-4-5) and (a1-4-8) are more preferred.

(a1-4-1)

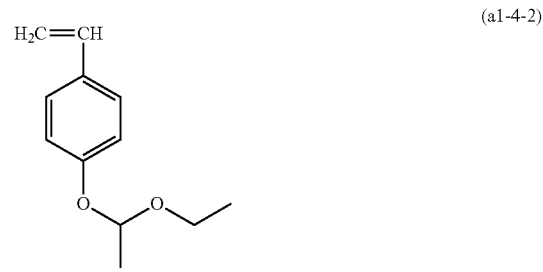

(a1-4-2)

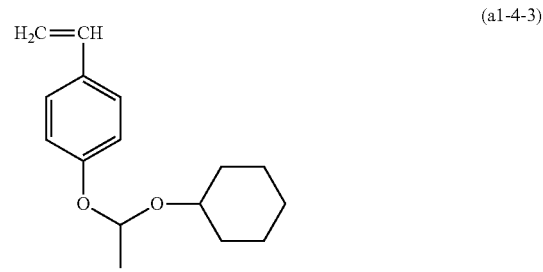

(a1-4-3)

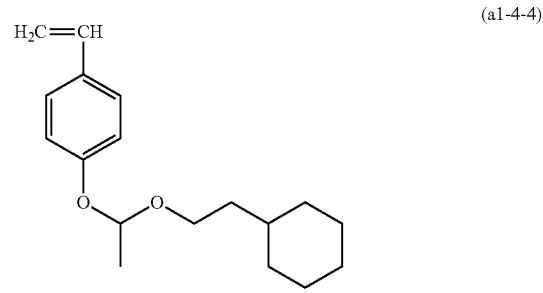

(a1-4-4)

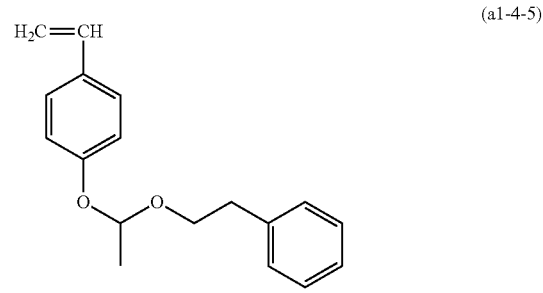

(a1-4-5)

-continued (a1-4-6)
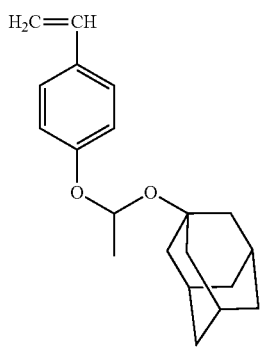

(a1-4-7)
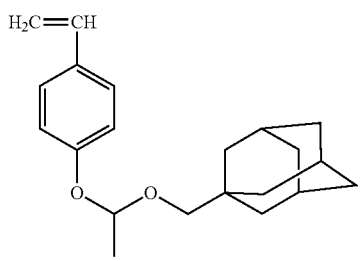

(a1-4-8)
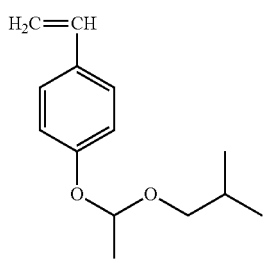

When Resin (A) has a structural unit represented by formula (a1-4), its content is usually 10 to 95% by mole, preferably 15 to 90% by mole and more preferably 20 to 85% by mole based on 100% by mole of all the structural units of the resin.

Other examples of the structural unit having an acid-labile group include one represented by the formula (a1-5):

(a1-5)
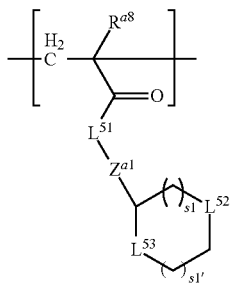

In formula (a1-5), $R^{a8}$ represents a hydrogen atom, a halogen atom, or a C1-C6 alkyl group which may have a halogen atom, $Z^{a1}$ represents a single bond or *—$(CH_2)_{h3}$—CO-$L^{54}$- in which h3 represents an integer of 1 to 4 and * represents a binding site to $L^{51}$, $L^{51}$, $L^{52}$, $L^{53}$ and $L^{54}$ each independently represent an oxygen atom or a sulfur atom, s1 represents an integer of 1 to 3, and s1' represents an integer of 0 to 3.

Herein, the structural unit represented by formula (a1-5) is sometimes referred to as "structural unit (a1-5)".

Examples of halogen atoms include a fluorine atom and a chlorine atom, preferably a fluorine atom.

Examples of the alkyl group which may have a halogen atom include a methyl group, an ethyl group, n-propyl group, an isopropyl group, an n-butyl group, a sec-butyl group, a tert-butyl group, a pentyl group, a hexyl group, a heptyl group, a 2-ethylhexyl group, an octyl group, a fluoromethyl group, and a trifluoromethyl group. In the formula (a1-5), $R^{a8}$ preferably represents a hydrogen atom, a methyl group, or a trifluoromethyl group.

$L^{51}$ represents preferably an oxygen atom.

It is preferred that one of $L^{52}$ and $L^{53}$ represents an oxygen atom, while the other represents a sulfur atom.

s1 preferably represents 1. s1' represents an integer of 0 to 2.

$Z^{a1}$ preferably represents a single bond or *—$CH_2$—CO—O— wherein * represents a binding site to $L^{51}$.

Examples of the monomer from which the structural unit (a-5) is derived include the following ones:

(a1-5-1)
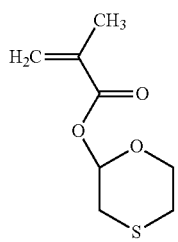

(a1-5-2)
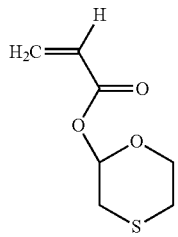

(a1-5-3)
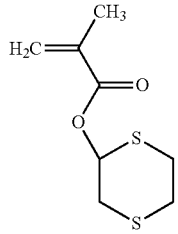

(a1-5-4)
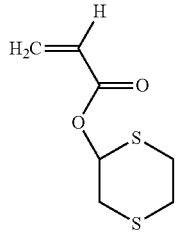

When Resin (A) has a structural unit (a1-5), its content is usually 1 to 50% by mole, preferably 3 to 45% by mole and more preferably 5 to 40% by mole based on 100% by mole of all the structural units of the resin.

Resin (A) has preferably one or more of the structural units (a1-0), (a1-1), (a1-2) and (a1-5), more preferably two or more of these structural units.

Specifically, it has preferably the structural units (a1-1) and (a1-2), the structural units (a1-1) and (a1-5), the structural units (a1-1) and (a1-0), the structural units (a1-5) and (a1-0), the structural units (a1-0), (a1-1) and (a1-2), or the structural units (a1-0), (a1-1) and (a1-5), more preferably the structural units (a1-1) and (a1-2) or the structural units (a1-1) and (a1-5) Resin (A) has preferably the structural unit (a1-1).

The content of the structural unit (a) is usually 10 to 80% by mole and preferably 20 to 60% by mole, based on all the structural units of Resin (A).

The structural unit(s) is derived from a monomer having no acid-labile group.

As to a monomer having no acid-labile group, monomers which have been known to in the art can be used as such monomer, and they are not limited to any specific one provided that it has no acid-labile group.

The structural unit having no acid-labile group preferably has a hydroxyl group or a lactone ring. When the resin (A) has the structural unit derived from the monomer having no acid-labile group and having a hydroxyl group or a lactone ring, a photoresist composition capable of providing a photoresist film with good resolution and adhesiveness of photoresist to a substrate can be obtained.

Hereinafter, the structural unit having no acid-labile group and having a hydroxy group is referred to as "structural unit (a2)", and the structural unit having no acid-labile group and having a lactone ring is referred to as "structural unit (a3)".

The hydroxy group which the structural unit (a2) has may be an alcoholic hydroxy group or a phenolic hydroxy group.

When KrF excimer laser (wavelength: 248 nm) lithography system, or a high energy laser such as electron beam and extreme ultraviolet is used as an exposure system, the resin which has the structural unit (a2) having a phenolic hydroxy group is preferred. When ArF excimer laser (wavelength: 193 nm) is used as an exposure system, the resin which has the structural unit (a2) having an alcoholic hydroxy group is preferred and the resin which has the structural unit (a2-1) described later is more preferred.

Resin (A) may have one or more of the structural units (a2).

Examples of the structural unit (a2) having a phenolic hydroxy group include one represented by the formula (a2-0).

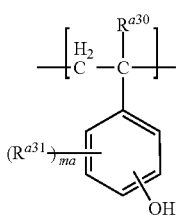

(a2-0)

In formula (a2-0), $R^{a30}$ represents a hydrogen atom, a halogen atom, a C1-C6 alkyl group or a C1-C6 halogenated alkyl group, $R^{a31}$ is independently in each occurrence a halogen atom, a hydroxyl group, a C1-C6 alkyl group, a C1-C6 alkoxy group, a C2-C4 acyl group, a C2-C4 acyloxy group, an acryloyl group or a methacryloyl group, "ma" represents an integer of 0 to 4.

In the formula (a2-0), examples of the halogen atom include a fluorine atom, a chlorine atom, a bromine atom or iodine atom, examples of the C1-C6 alkyl group include a methyl group, an ethyl group, a propyl group, an isopropyl group, a butyl group, an isobutyl group, a sec-butyl group, a tert-butyl group, a pentyl group and a hexyl group, and a C1-C4 alkyl group is preferred and a C1-C2 alkyl group is more preferred and a methyl group is especially preferred.

Examples of the C1-C6 halogenated alkyl group include a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group and a perfluorohexyl group. Examples of the C1-C6 alkoxy group include a methoxy group, an ethoxy group, a propoxy group, an isopropoxy group, a butoxy group, an isobutoxy group, a sec-butoxy group, a tert-butoxy group, a pentyloxy group and a hexyloxy group, and a C1-C4 alkoxy group is preferred and a C1-C2 alkoxy group is more preferred and a methoxy group is especially preferred. Examples of the C2-C4 acyl group include an acetyl group, a propyonyl group and a butyryl group, and examples of the C2-C4 acyloxy group include an acetyloxy group, a propyonyloxy group and a butyryloxy group.

In the formula (a2-0), "ma" is preferably 0, 1 or 2, and is more preferably 0 or 1, and especially preferably 0.

Examples of the monomer from which the structural unit (a2-0) is derived include compounds mentioned in JP2010-204634A. Among them, the structural units represented by formulae (a2-0-1), (a2-0-2), (a2-0-3) and (a2-0-4) are preferred as the structural unit represented by formula (a2-0), and those represented by formulae (a2-0-1) and (a2-0-2) are more preferred.

(a2-0-1)

(a2-0-2)

(a2-0-3)

(a2-0-4)

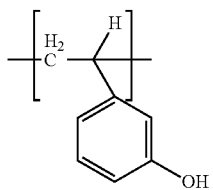

Resin (A) which has a structural unit represented by formula (a2-0) can be produced, for example, by polymerizing a monomer where its phenolic hydroxyl group has been protected with a suitable protecting group, followed by deprotection. Examples of the protecting group for a phenolic hydroxyl group include an acetyl group.

When Resin (A) has the structural unit represented by formula (a2-0), its content is usually 5 to 95% by mole and preferably 10 to 85% by mole and more preferably 15 to 80% by mole based on all the structural units of the resin.

Examples of the structural unit (a2) having an alcoholic hydroxy group include one represented by the formula (a2-1):

(a2-1)

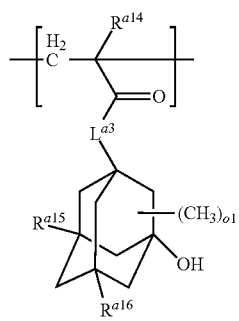

wherein $R^{a14}$ represents a hydrogen atom or a methyl group, $R^{a15}$ and $R^{a16}$ each independently represent a hydrogen atom, a methyl group or a hydroxyl group, $L^{a3}$ represents *—O— or *—O—$(CH_2)_{k2}$—CO—O— in which * represents a binding site to —CO—, and k2 represents an integer of 1 to 7, and "o1" represents an integer of 0 to 10. Hereinafter, the structural unit represented by formula (a2-1) is referred to as "structural unit (a2-1)".

In the formula (a2-1), $R^{a14}$ is preferably a methyl group. $R^{a15}$ is preferably a hydrogen atom. $R^{a16}$ is preferably a hydrogen atom or a hydroxyl group. $L^{a3}$ is preferably *—O— or *—O—$(CH_2)_{f2}$—CO—O— in which * represents a binding site to —CO—, and "f2" represents an integer of 1 to 4, is more preferably *—O— and *—O—$CH_2$—CO—O—, and is still more preferably *—O—, and "o1" is preferably 0, 1, 2 or 3 and is more preferably 0 or 1.

Examples of monomers from which the structural unit represented by formula (a2-1) is derived include compounds mentioned in JP2010-204646A.

Preferred examples of the monomer from which the structural unit represented by formula (a2-1) is derived include those represented by formulae (a2-1-1) to (a2-1-6).

(a2-1-1)

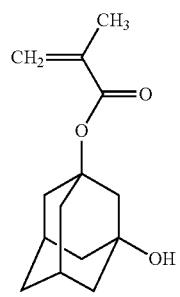

(a2-1-2)

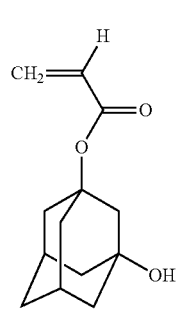

(a2-1-3)

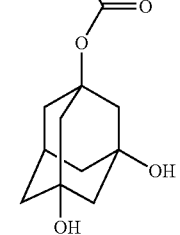

(a2-1-4)

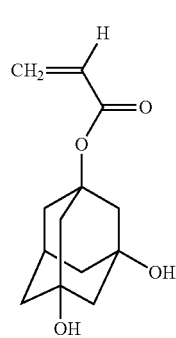

-continued

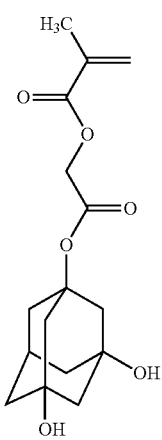

(a2-1-5)

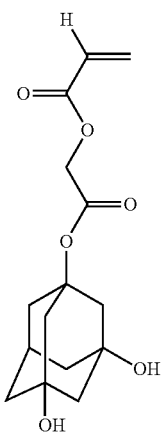

(a2-1-6)

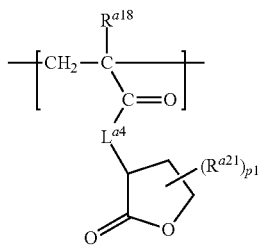

(a3-1)

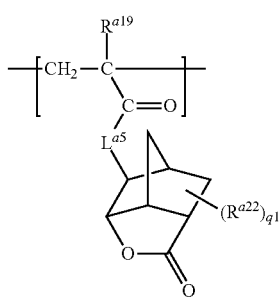

(a3-2)

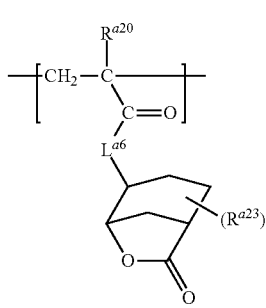

(a3-3)

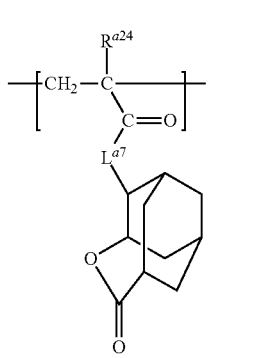

(a3-4)

Among them, more preferred are the monomer represented by formulae (a2-1-1), (a2-1-2), (a2-1-3) and (a2-1-4), still more preferred are the monomers represented by formulae (a2-1-1) and (a2-1-3).

When Resin (A) has the structural unit (a2-1), its content is usually 1 to 45% by mole, preferably 1 to 40% by mole, and more preferably 1 to 35% by mole, and especially preferably 2 to 20% by mole, based on all the structural units of the resin.

Examples of the lactone ring contained in the structural unit (a3) include a monocyclic lactone ring such as β-propiolactone ring, γ-butyrolactone ring and γ-valerolactone ring, and a condensed ring formed from a monocyclic lactone ring and the other ring. Among them, preferred are γ-butyrolactone ring and a condensed lactone ring formed from γ-butyrolactone ring and the other ring.

Preferable examples of the structural unit (a3) include those represented by the formulae (a3-1), (a3-2), (a3-3) and (a3-4).

In formulae, $L^{a4}$, $L^{a5}$ and $L^{a6}$ each independently represent *—O— or *—O—$(CH_2)_{k3}$—CO—O— in which * represents a binding site to —CO— and k3 represents an integer of 1 to 7, $R^{a18}$, $R^{a19}$ and $R^{a20}$ each independently represent a hydrogen atom or a methyl group, $R^{a21}$ represents a C1-C4 aliphatic hydrocarbon group, $R^{a22}$ and $R^{a23}$ are independently in each occurrence a carboxyl group, a cyano group or a C1-C4 aliphatic hydrocarbon group, $R^{a24}$ each independently represent a hydrogen atom, a halogen atom, or a C1-C6 alkyl group which may have a halogen atom, $L^{a7}$ represents a single bond, $*^1$-$L^{a8}$-O—, $*^1$-$L^{a8}$-CO—O—, $*^1$-$L^{a8}$-CO—O-$L^{a9}$-CO—O— or $*^1$-$L^{a8}$-CO—O-$L^{a9}$-O— in which $L^{a8}$ and $L^{a9}$ each independently represent C1-C6 alkanediyl group, $*^1$ represents a binding site to —CO—, and p1 represents an integer of 0 to 5, q1 and r1 independently each represent an integer of 0 to 3.

Examples of halogen atom represented by $R^{a24}$ include a fluorine atom, a chlorine atom, a bromine atom and an iodine atom.

Examples of the alkyl group represented by $R^{a24}$ include a methyl group, an ethyl group, a propyl group, a butyl group, a pentyl group, and a hexyl group, preferably a C1-C4 alkyl group, and more preferably a methyl group and an ethyl group.

As to $R^{a24}$, examples of the alkyl group which has an halogen atom include a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group, a perfluorohexyl group, a trichloromethyl group, a tribromomethyl group, and a triiodomethyl group.

As to $L^{a8}$ and $L^{a9}$, examples of the alkanediyl group include a methylene group, an ethylene group, a propane-1,3-diyl group, a butane-1,4-diyl group, a pentane-1,5-diyl group and a hexane-1,6-diyl group, a butane-1,3-diyl group, 2-methylpropane-1,3-diyl group, a 2-methylpropane-1,2-diyl group, a pentane-1,4-diyl group and a 2-methylbutane-1,4-diyl group.

It is preferred that $L^{a4}$, $L^{a5}$ and $L^{a6}$ each independently represent *—O— or *—O—$(CH_2)_{d1}$—CO—O— in which * represents a binding site to —CO— and d1 represents an integer of 1 to 4, and it is more preferred that $L^{a4}$, $L^{a5}$ and $L^{a6}$ are *—O— and *—O—$CH_2$—CO—O—, and it is still more preferred that $L^{a4}$, $L^{a5}$ and $L^{a6}$ are *—O—.

$R^{a18}$, $R^{a19}$ and $R^{a20}$ are preferably methyl groups. $R^{a21}$ is preferably a methyl group. It is preferred that $R^{a22}$ and $R^{a23}$ are independently in each occurrence a carboxyl group, a cyano group or a methyl group.

It is preferred that p1, q1 and r1 each independently represent an integer of 0 to 2, and it is more preferred that p1, q1 and r1 each independently represent 0 or 1.

$R^{a24}$ is preferably a hydrogen atom or a C1-C4 alkyl group, more preferably a hydrogen atom, a methyl group or an ethyl group, and still more preferably a hydrogen atom or a methyl group.

$L^{a7}$ represents preferably a single bond or $*^1$-$L^{a8}$-CO—O—, more preferably a single bond, $*^1$—$CH_2$—CO—O— or $*^1$—$C_2H_4$—CO—O—.

Examples of the monomer from which the structural unit (a3) is derived include those mentioned in JP2010-204646A, JP2000-122294A and JP2012-41274A. As the structural unit (a3), preferred are those represented by the formulae (a3-1-1) to (a3-1-4), the formulae (a3-2-1) to (a3-2-4), the formulae (a3-3-1) to (a3-3-4) and the formulae (a3-4-1) to (a3-4-12), more preferred are those represented by the formulae (a3-1-1), (a3-1-2), (a3-2-3), (a3-2-4) and (a3-4-1) to (a3-4-12), still more preferred are those represented by the formulae (a3-4-1) to (a3-4-12), and further still more preferred are those represented by the formulae (a3-4-1) to (a3-4-6).

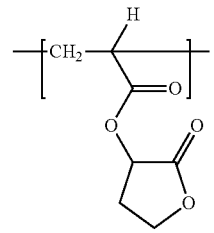

(a3-1-1)

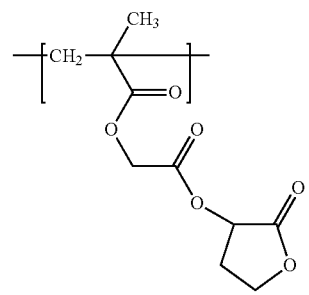

(a3-1-2)

(a3-1-3)

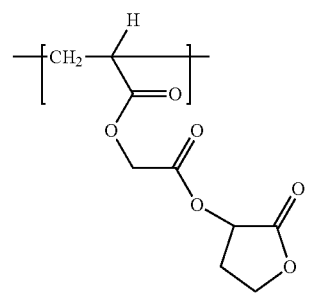

(a3-1-4)

(a3-2-1)

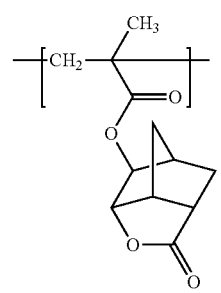

(a3-2-2)

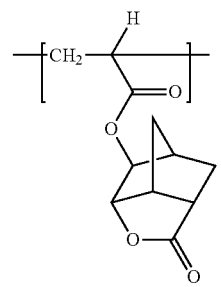

(a3-2-3)
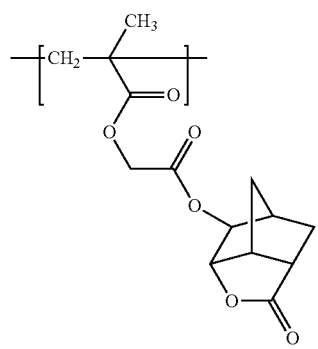
(a3-2-4)
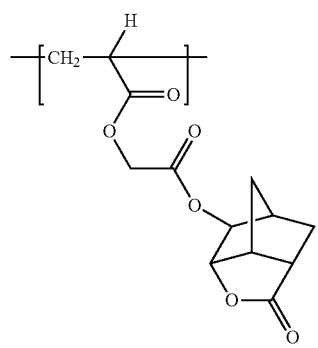
(s3-3-1)
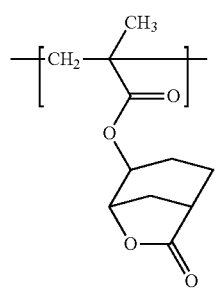
(a3-3-2)
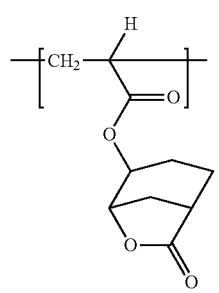
(a3-3-3)
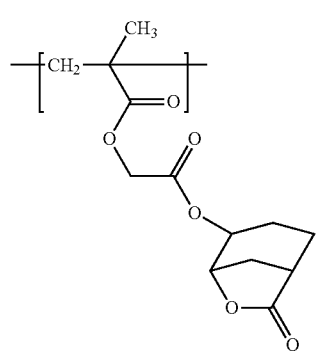
(a3-3-4)
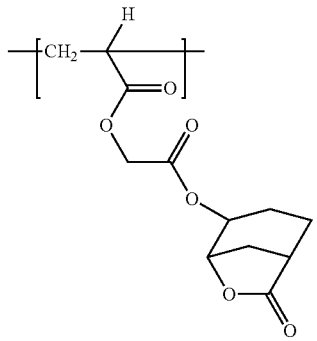
(a3-4-1)
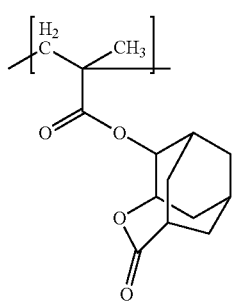
(a3-4-2)
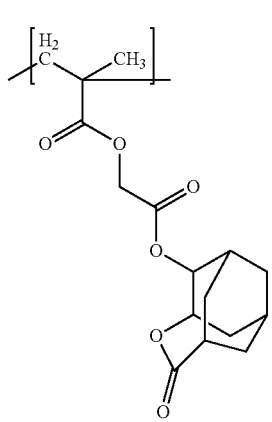
(a3-4-3)
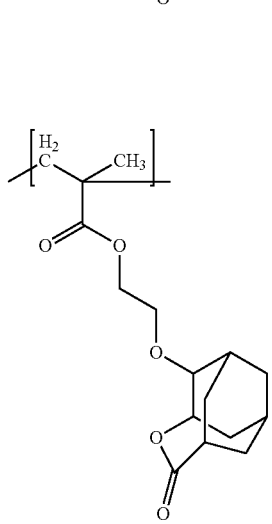

(a3-4-4)
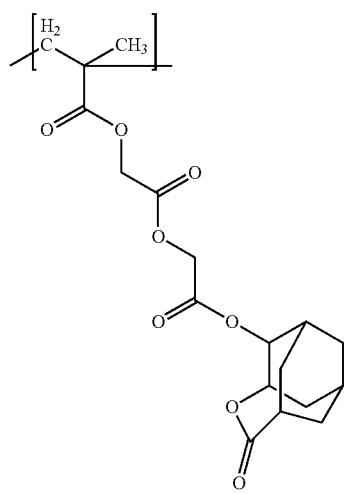
(a3-4-5)
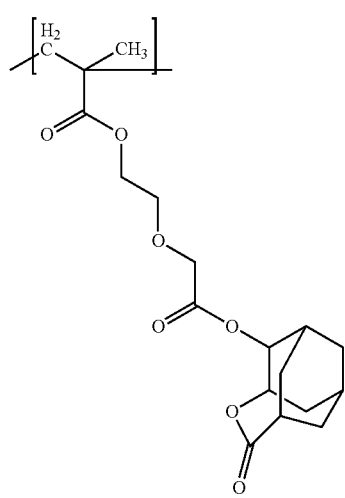
(a3-4-6)
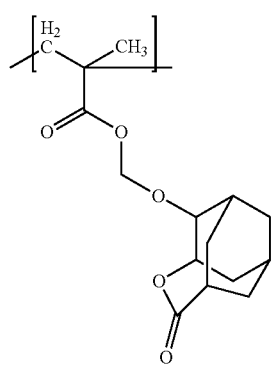
(a3-4-7)
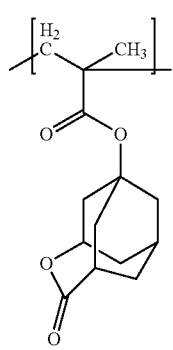
(a3-4-8)
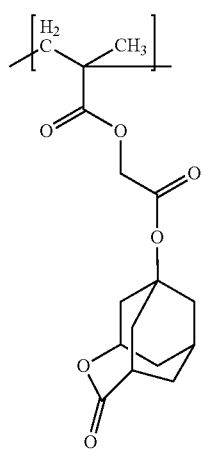
(a3-4-9)
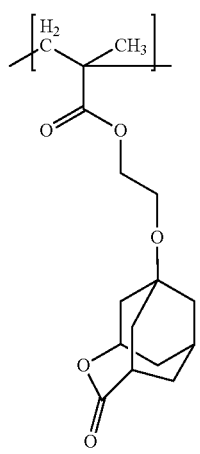

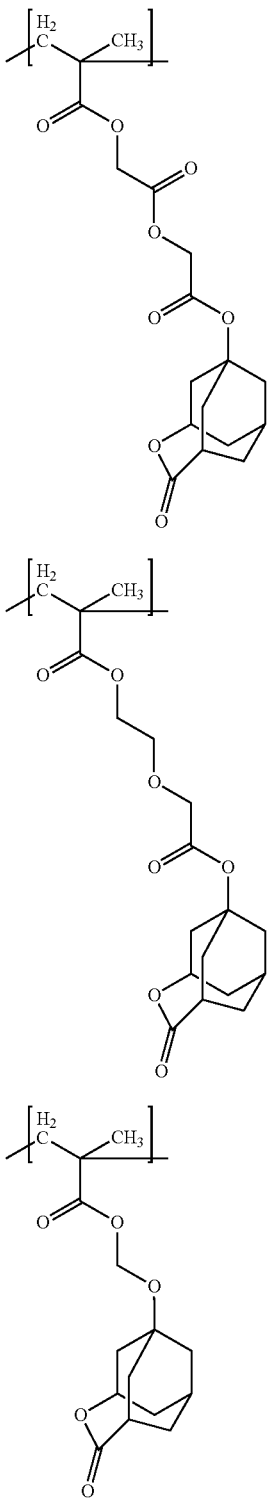

(a3-4-10)

(a3-4-11)

(a3-4-12)

Specific examples of the structural unit (a3) include those where methyl groups of formulae (a3-4-1) to (a3-4-6) have been replaced by hydrogen atoms.

When Resin (A) has the structural unit (a3), its content thereof is preferably 5 to 70% by mole, and more preferably 10 to 65% by mole and more preferably 10 to 60% by mole, based on all the structural units of the resin.

When Resin (A) has the structural unit represented by formula (a3-1), (a3-2), (a3-3) or (a3-4), the total content of them is preferably 5 to 60% by mole, and more preferably 5 to 50% by mole and more preferably 10 to 50% by mole, based on all the structural units of the resin.

Examples of another structural unit having no acid-labile group include a structural unit having a halogen atom and a structural unit which has a hydrocarbon not being removed therefrom by action of an acid.

Examples of the structural unit having a halogen atom, which is sometimes referred to as "structural unit (a4)", include a structural unit represented by formula (a4-0).

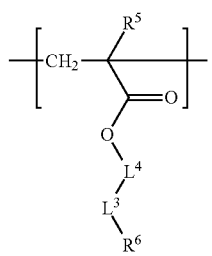

(a4-0)

In the formula (a4-0), $R^5$ represents a hydrogen atom or a methyl group, $L^4$ represents a single bond or a C1 to C4 saturated aliphatic hydrocarbon group, $L^3$ represents a $C_1$ to $C_8$ perfluoroalkanediyl group, or a $C_3$ to $C_{12}$ perfluorocycloalkanediyl group, and $R^6$ represents a hydrogen atom or a fluorine atom.

Examples of the saturated aliphatic hydrocarbon group for $L^4$ include $C_1$ to $C_4$ alkanediyl group, i.e., a linear alkanediyl group such as methylene, ethylene, propane-1,3-diyl, butane-1,4-diyl; and a branched alkanediyl group ethane-1,1-diyl, propane-1,2-diyl, butane-1,3-diyl, 2-methylpropane-1,3-diyl and 2-methylpropane-1,2-diyl groups.

$L^4$ is preferably a single bond, methylene or ethylene group, and more preferably a single bond or methylene group.

Examples of the perfluoroalkanediyl group for $L^3$ include difluoromethylene, perfluoroethylene, perfluoroethyl fluoromethylene, perfluoropropane-1,3-diyl, a perfluoropropane-1,2-diyl, perfluoropropane-2,2-diyl, perfluorobutane-1,4-diyl, perfluorobutane-2,2-diyl, perfluorobutane-1,2-diyl, perfluoropentane-1,5-diyl, perfluoropentane-2,2-diyl, perfluoropentane-3,3-diyl, perfluorohexane-1,6-diyl, perfluorohexane-2,2-diyl, perfluorohexane-3,3-diyl, perfluoroheptane-1,7-diyl, perfluoroheptane-2,2-diyl, perfluoroheptane-3,4-diyl, perfluoroheptane-4,4-diyl, perfluorooctan-1,8-diyl, perfluorooctan-2,2-diyl, perfluorooctan-3,3-diyl and perfluorooctan-4,4-diyl groups.

Examples of the perfluoro cycloalkanediyl group for $L^3$ include perfluorocyclohexanediyl, perfluorocyclopentanediyl, perfluorocycloheptanediyl and perfluoroadamantanediyl groups.

$L^3$ is preferably a $C_1$ to $C_6$ perfluoroalkanediyl group, more preferably a $C_1$ to $C_3$ perfluoroalkanediyl group.

Examples of the structural unit represented by formula (a4-0) include those as follow.

(a4-0-1) through (a4-0-13): chemical structures of fluorinated methacrylate polymer repeat units.

(a4-0-14)

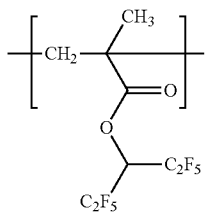

(a4-0-15)

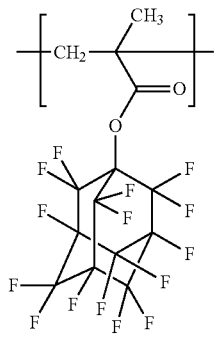

(a4-0-16)

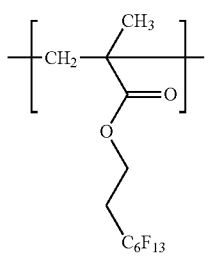

Examples of the structural unit represented by formula (a4-0) include the structural units represented by the above formulae in which a methyl group corresponding to $R^5$ has been replaced by a hydrogen atom.

Examples of the structural unit (a4) include those represented by formula (a4-1):

(a4-1)

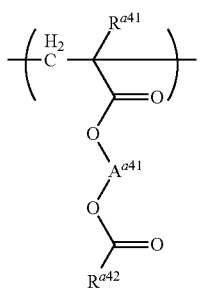

wherein $R^{a41}$ represents a hydrogen atom or a methyl group, $R^{a42}$ represents an optionally substituted $C_1$ to $C_{20}$ hydrocarbon group where a methylene group may be replaced by an oxygen atom or a carbonyl group, and $A^{a41}$ represents an optionally substituted $C_1$ to $C_6$ alkanediyl group or a group represented by formula (a-g1), (a-g1)

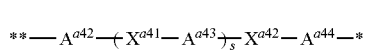

wherein s represents 0 or 1, $A^{a42}$ and $A^{a44}$ each independently represent an optionally substituted $C_1$ to $C_5$ aliphatic hydrocarbon group, $A^{a43}$ represents a single bond or an optionally substituted $C_1$ to $C_5$ aliphatic hydrocarbon group, and $X^{a41}$ and $X^{a42}$ each independently represent —O—, —CO—, —CO—O— or —O—CO—, provided that the total number of the carbon atoms contained in the group of $A^{a42}$, $A^{a43}$, $A^{a44}$, $X^{a41}$ and $X^{a42}$ is 7 or less, at least one of $A^{a41}$ and $R^{a42}$ has a halogen atom as a substituent, and

* and ** represent a binding site, and * represents a binding site to —O—CO— $R^{a42}$.

The hydrocarbon group for $R^{a42}$ may be a chain aliphatic hydrocarbon group, a cyclic aliphatic hydrocarbon group, an aromatic hydrocarbon group and a combination thereof.

The chain aliphatic hydrocarbon group and the cyclic aliphatic hydrocarbon group may have a carbon-carbon unsaturated bond, and is preferably a chain saturated aliphatic hydrocarbon group and a cyclic saturated aliphatic hydrocarbon group. Examples of the saturated aliphatic hydrocarbon group include a linear or branched alkyl group, a monocyclic or polycyclic alicyclic hydrocarbon group, and an aliphatic hydrocarbon group formed by combining the alkyl group and the alicyclic hydrocarbon group.

Examples of the chain aliphatic hydrocarbon group include an alkyl group such as methyl, ethyl, propyl, butyl, pentyl, hexyl, heptyl, octyl, decyl, dodecyl and hexadecyl groups.

Examples of the alicyclic hydrocarbon group include a cycloalkyl group such as cyclopentyl, cyclohexyl, cycloheptyl, cyclooctyl groups; and polycyclic hydrocarbon groups such as decahydronaphtyl, adamantyl and norbornyl groups as well as groups below. * represents a binding site.

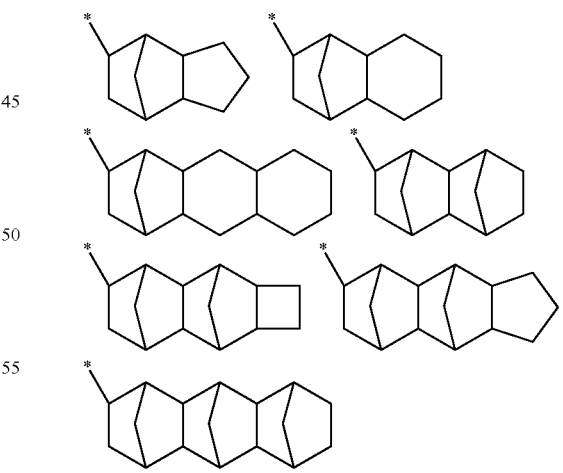

Examples of the aromatic hydrocarbon group include an aryl group such as phenyl, naphthyl, anthryl, biphenyl, phenanthryl and fluorenyl groups.

The hydrocarbon group for $R^{a42}$ is preferably a chain saturated aliphatic hydrocarbon group, a cyclic aliphatic hydrocarbon group, and a combination thereof. The hydrocarbon group may have a carbon-carbon unsaturated bond, is preferably a chain and a cyclic saturated aliphatic hydrocarbon groups, and a combination thereof.

Examples of the substituent for $R^{a42}$ include a halogen atom or a group represented by formula (a-g3):

$$*-X^{a43}-A^{a45} \quad (a\text{-}g3)$$

wherein $X^{a43}$ represent an oxygen atom, a carbonyl group, a carbonyloxy group or an oxycarbonyl group, $A^{a45}$ represents a $C_1$ to $C_{17}$ aliphatic hydrocarbon group that has a halogen atom, and \* represents a binding site.

Examples of the halogen atom include a fluorine atom, a chlorine atom, a bromine atom and an iodine atom, and preferably a fluorine atom.

Examples of the aliphatic hydrocarbon group for $A^{a45}$ include the same ones as those for $R^{a42}$.

$R^{a42}$ is preferably an aliphatic hydrocarbon group that may have a halogen atom, and more preferably an alkyl group having a halogen atom and/or an aliphatic hydrocarbon group having the group represented by the formula (a-g3).

When $R^{a42}$ is an aliphatic hydrocarbon group having a halogen atom, an aliphatic hydrocarbon group having a fluorine atom is preferred, a perfluoroalkyl group or a perfluorocycloalkyl group are more preferred, a $C_1$ to $C_6$ perfluoroalkyl group is still more preferred, a $C_1$ to $C_3$ perfluoroalkyl group is particularly preferred.

Examples of the perfluoroalkyl group include perfluoromethyl, perfluoroethyl, perfluoropropyl, perfluorobutyl, perfluoropentyl, perfluorohexyl, perfluoroheptyl and perfluorooctyl groups. Examples of the perfluorocycloalkyl group include perfluorocyclohexyl group.

When $R^{a42}$ is an aliphatic hydrocarbon group having the group represented by the formula (a-g3), the total number of the carbon atoms contained in the aliphatic hydrocarbon group including the group represented by the formula (a-g3) is preferably 15 or less, more preferably 12 or less. The number of the group represented by the formula (a-g3) is preferably one when the group represented by the formula (a-g3) is the substituent.

The aliphatic hydrocarbon group having the group represented by the formula (a-g3) is more preferably a group represented by formula (a-g2):

$$*-A^{a46}-X^{a44}-A^{a47} \quad (a\text{-}g2)$$

wherein $A^{a46}$ represents a $C_1$ to $C_{17}$ aliphatic hydrocarbon group that may have a halogen atom, $X^{a44}$ represent a carbonyloxy group or an oxycarbonyl group, $A^{a47}$ represents a $C_1$ to $C_{17}$ aliphatic hydrocarbon group that may have a halogen atom, provided that the total number of the carbon atoms contained in the group of $A^{a46}$, $X^{a44}$ and $A^{a47}$ is 18 or less, at least one of $A^{a46}$ and $A^{a47}$ has a halogen atom, and \* represents a binding site to a carbonyl group.

The aliphatic hydrocarbon group for $A^{a46}$ has preferably 1 to 6 carbon atoms, more preferably 1 to 3 carbon atoms.

The he aliphatic hydrocarbon group for $A^{a47}$ has preferably 4 to 15 carbon atoms, more preferably 5 to 12 carbon atoms. $A^{a47}$ is more preferably a cyclohexyl group or an adamantyl group.

Preferred examples of $*-A^{a46}-X^{a44}-A^{a47}$ include the following ones.

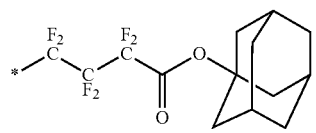

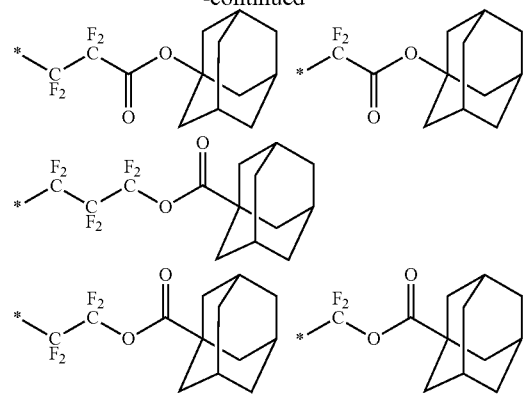

Examples of the alkanediyl group for $A^{a41}$ include a linear alkanediyl group such as methylene, ethylene, propane-1,3-diyl, butane-1,4-diyl, pentane-1,5-diyl and hexane-1,6-diyl groups;

a branched alkanediyl group such as propane-1,2-diyl, butan-1,3-diyl, 2-methylpropane-1,2-diyl, 1-methylbutane-1,4-diyl, 2-methylbutane-1,4-diyl groups.

Examples of the substituent on the alkanediyl group for $A^{a41}$ include a hydroxy group and a $C_1$ to $C_6$ alkoxy group.

$A^{a41}$ is preferably a $C_1$ to $C_4$ alkanediyl group, more preferably a $C_2$ to $C_4$ alkanediyl group, and still more preferably an ethylene group.

In the group represented by the formula (a-g1) (which is sometimes referred to as "group (a-g1)"), examples of the aliphatic hydrocarbon group for $A^{a42}$, $A^{a43}$ and $A^{a44}$ include methylene, ethylene, propane-1,3-diyl, propane-1,2-diyl, butane-1,4-diyl, 1-methylpropane-1,3-diyl, 2-methylpropane-1,3-diyl and 2-methylpropane-1,2-diyl groups.

Examples of the substituent on the aliphatic hydrocarbon group for $A^{a42}$, $A^{a43}$ and $A^{a44}$ include a hydroxy group and a $C_1$ to $C_6$ alkoxy group.

s is preferably 0.

Examples of the group (a-g1) in which $X^{a42}$ represents an oxygen atom, a carbonyl group, a carbonyloxy group, or an oxycarbonyl group include the following ones. In the formula, \* and \*\* each represent a binding site, and \*\* represents a binding site to —O—CO—$R^{a42}$.

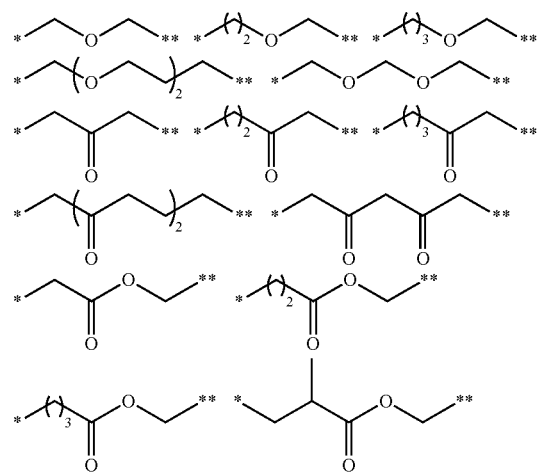

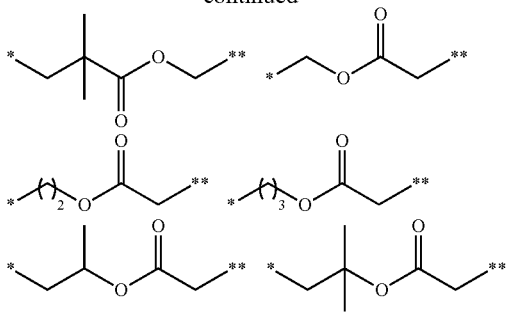

The structural unit represented by the formula (a4-1) is preferably structural units represented by formula (a4-2) and formula (a4-3):

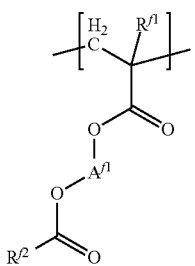

wherein $R^{f1}$ represents a hydrogen atom or a methyl group,
$A^{f1}$ represent a $C_1$ to $C_6$ alkanediyl group, and
$R^{f2}$ represents a $C_1$ to $C_{10}$ hydrocarbon group that has a fluorine atom;

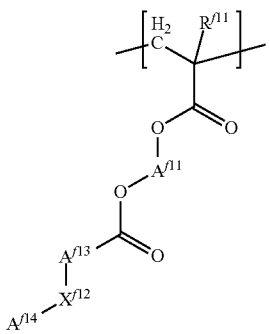

where $R^{f11}$ represents a hydrogen atom or a methyl group,
$A^{f11}$ represent a $C_1$ to $C_6$ alkanediyl group,
$A^{f13}$ represents a $C_1$ to $C_{18}$ aliphatic hydrocarbon group that may have a fluorine atom,
$X^{f12}$ represents an oxycarbonyl group or a carbonyloxy group,
$A^{f14}$ represents a $C_1$ to $C_{17}$ aliphatic hydrocarbon group that may have a fluorine atom, and
provided that at least one of $A^{f13}$ and $A^{f14}$ represents an aliphatic hydrocarbon group having a fluorine atom.

Examples of the alkanediyl group for $A^{f1}$ include a linear alkanediyl group such as methylene, ethylene, propane-1,3-diyl, propane-1,2-diyl, butane-1,4-diyl, pentane-1,5-diyl and hexane-1,6-diyl groups;
a branched alkanediyl group such as 1-methylpropane-1,3-diyl, 2-methylpropane-1,3-diyl, 2-methylpropane-1,2-diyl, 1-methylbutane-1,4-diyl and 2-methylbutane-1,4-diyl groups.

The hydrocarbon group for $R^{f2}$ includes an aliphatic hydrocarbon group and an aromatic hydrocarbon group. The aliphatic hydrocarbon group includes chain and cyclic groups, and a combination thereof.

The aliphatic hydrocarbon group is preferably an alkyl group and a cyclic aliphatic hydrocarbon group.

Examples of the alkyl group include methyl, ethyl, n-propyl, isopropyl, n-butyl, sec-butyl, tert-butyl, n-pentyl, n-hexyl, n-heptyl, n-octyl and 2-ethylhexyl groups.

Examples of the cyclic aliphatic hydrocarbon group include any of a monocyclic group and a polycyclic group. Examples of the monocyclic alicyclic hydrocarbon group include a cycloalkyl group such as cyclopropyl, cyclobutyl, cyclopentyl, cyclohexyl, methylcyclohexyl, dimethylcyclohexyl, cycloheptyl, cyclooctyl, and cyclodecyl groups, Examples of the polycyclic hydrocarbon groups includes decahydronaphthyl, adamantyl, 2-alkyladamantane-2-yl, 1-(adamantane-1-yl) alkane-1-yl, norbornyl, methylnorbornyl and isobornyl groups.

Examples of the hydrocarbon group having a fluorine atom for $R^{f2}$ include an alkyl group having a fluorine atom and an alicyclic hydrocarbon group having a fluorine atom.

Specific examples of an alkyl group having a fluorine atom include a fluorinated alkyl group such as difluoromethyl, trifluoromethyl, 1,1-difluoroethyl, 2,2-difluoroethyl, 2,2,2-trifluoroethyl, perfluoroethyl, 1,1,2,2-tetrafluoropropyl, 1,1,2,2,3,3-hexafluoropropyl, perfluoroethylmethyl, 1-(trifluoromethyl)-1,2,2,2-tetrafluoroethyl, perfluoropropyl, 1-(trifluoromethyl)-2,2,2-trifluoroethyl, perfluoropropyl, 1,1,2,2-tetrafluorobutyl, 1,1,2,2,3,3-hexafluorobutyl, 1,1,2,2,3,3,4,4-octafluorobutyl, perfluorobutyl, 1,1-bis(trifluoro)methyl-2,2,2-trifluoroethyl, 2-(perfluoropropyl)ethyl, 1,1,2,2,3,3,4,4-octafluoropentyl, perfluoropentyl, 1,1,2,2,3,3,4,4,5,5-decafluoropentyl, 1,1-bis(trifluoromethyl)2,2,3,3,3-pentafluoropropyl, 2-(perfluorobutyl)ethyl, 1,1,2,2,3,3,4,4,5,5-decafluorohexyl, 1,1,2,2,3,3,4,4,5,5,6,6-dodeca fluorohexyl, perfluoropentylmethyl and perfluorohexyl groups.

Examples of the alicyclic hydrocarbon group having a fluorine atom include a fluorinated cycloalkyl group such as perfluorocyclohexyl and perfluoroadamantyl groups.

In the formula (a4-2), $A^{f1}$ is preferably a $C_2$ to $C_4$ alkanediyl group, and more preferably an ethylene group.

$R^{f2}$ is preferably a $C_1$ to $C_6$ fluorinated alkyl group.

Examples of the alkanediyl group for $A^{f11}$ include the same ones as those for $A^{f1}$.

Examples of the aliphatic hydrocarbon group for $A^{f13}$ include any of a divalent chain or cyclic aliphatic hydrocarbon group, or a combination thereof. The aliphatic hydrocarbon group may have a carbon-carbon unsaturated bond, and is preferably a saturated aliphatic hydrocarbon group.

The aliphatic hydrocarbon group that may have a fluorine atom for $A^{f13}$ is preferably the saturated aliphatic hydrocarbon group that may have a fluorine atom, and more preferably perfuloroalkandiyl group.

Examples of the divalent chain aliphatic hydrocarbon that may have a fluorine atom include an alkanediyl group such as methylene, ethylene, propanediyl, butanediyl and pentanediyl groups; a perfluoroalkanediyl group such as difluoromethylene, perfluoroethylene, perfluoropropanediyl, perfluorobutanediyl and perfluoropentanediyl groups.

The divalent cyclic aliphatic hydrocarbon group that may have a fluorine atom is any of monocyclic or polycyclic group.

Examples of the monocyclic aliphatic hydrocarbon group include cyclohexanediyl and perfluorocyclohexanediyl groups.

Examples of the polycyclic aliphatic hydrocarbon group include adamantanediyl, norbornanediyl and perfluoroadamantanediyl groups.

Examples of the aliphatic hydrocarbon group for $A'^{14}$ include a chain aliphatic hydrocarbon group, a cyclic aliphatic hydrocarbon group, and a combination thereof. The aliphatic hydrocarbon group may have a carbon-carbon unsaturated bond, and is preferably a saturated aliphatic hydrocarbon group.

The aliphatic hydrocarbon group that may have a fluorine atom for $A'^{14}$ for $A'^{14}$ is preferably the saturated aliphatic hydrocarbon group that may have a fluorine atom.

Examples of the chain aliphatic hydrocarbon group that may have a halogen atom include trifluoromethyl, difluoromethyl, methyl, perfluoromethyl, 1,1,1-trifluoroethyl, 1,1,2,2-tetrafluoroethyl, ethyl, perfluoropropyl, 1,1,1,2,2-pentafluoropropyl, propyl, perfluorobutyl, 1,1,2,2,3,3,4,4-octafluorobutyl, butyl, perfluoropentyl, 1,1,1,2,2,3,3,4,4-nonafluoropentyl, pentyl, hexyl, perfluorohexyl, hepthyl, perfluoroheptyl, octyl and perfluorooctyl groups.

The cyclic aliphatic hydrocarbon group that may have a fluorine atom may be any of a monocyclic hydrocarbon group and a polycyclic hydrocarbon group. Examples of the group containing the monocyclic aliphatic hydrocarbon group include cyclopropylmethyl, cyclopropyl, cyclobutylmethyl, cyclopentyl, cyclohexyl and perfluorocyclohexyl groups. Examples of the group containing the polycyclic aliphatic hydrocarbon group includes adamantyl, adamantylmethyl, norbornyl, norbornylmethyl, perfluoroadamantyl and perfluoroadamantylmethyl groups.

In the formula (a4-3), $A'^{11}$ is preferably an ethylene group.

The aliphatic hydrocarbon group for $A'^{13}$ is preferably a $C_1$ to $C_6$ aliphatic hydrocarbon group, more preferably a $C_2$ to $C_3$ aliphatic hydrocarbon group.

The aliphatic hydrocarbon group for $A'^{14}$ is preferably a $C_3$ to $C_{12}$ aliphatic hydrocarbon group, more preferably a $C_3$ to $C_{10}$ aliphatic hydrocarbon group. Among these, $A'^{14}$ is preferably a group containing a $C_3$ to $C_{12}$ alicyclic hydrocarbon group, more preferably cyclopropylmethyl, cyclopentyl, cyclohexyl, norbornyl and adamantyl groups.

Examples of the structural unit represented by formula (a4-2) include structural units represented by formula (a4-1-1) to formula (a4-1-22).

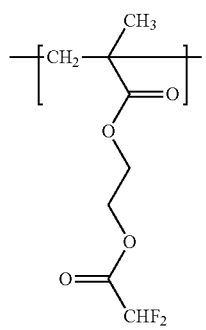

(a4-1-1)

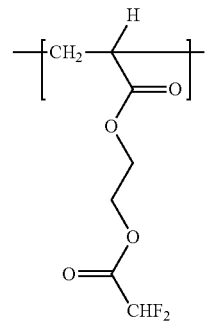

(a4-1-2)

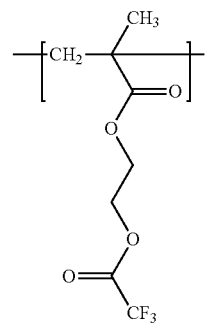

(a4-1-3)

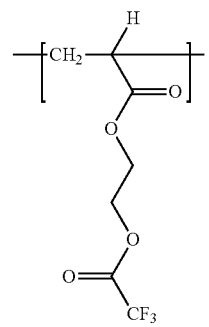

(a4-1-4)

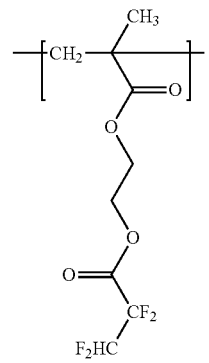

(a4-1-5)

(a4-1-6)
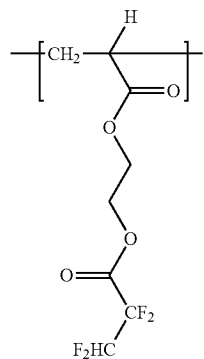
(a4-1-7)
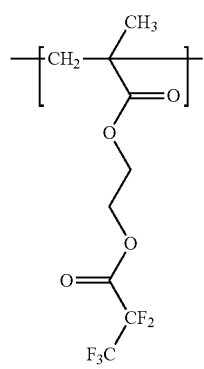
(a4-1-8)
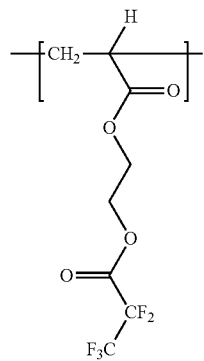
(a4-1-9)
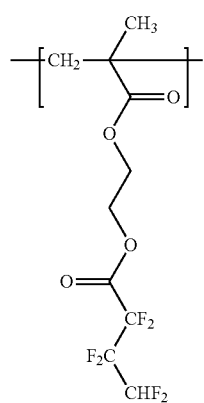
(a4-1-10)
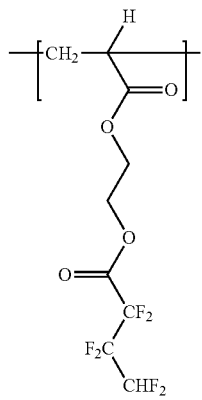
(a4-1-11)
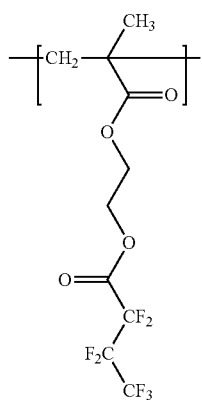
(a4-1-12)
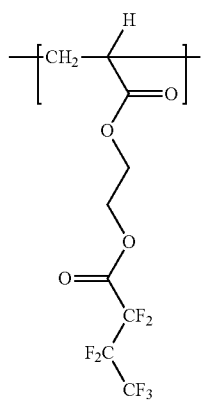
(a4-1-13)
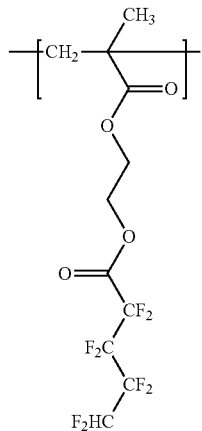

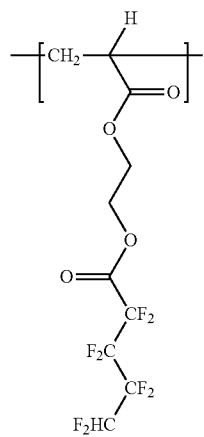
(a4-1-14)
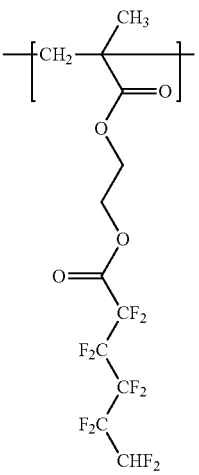
(a4-1-17)
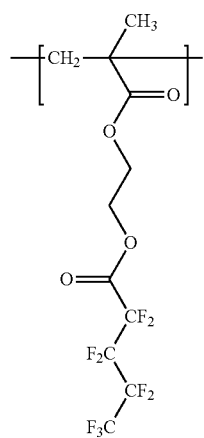
(a4-1-15)
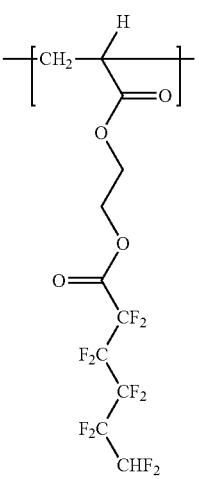
(a4-1-18)
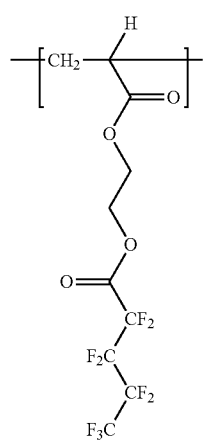
(a4-1-16)
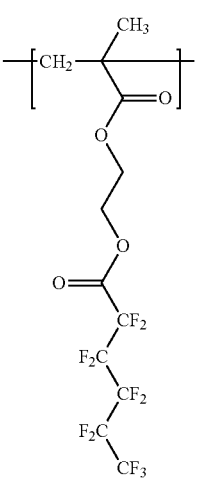
(a4-1-19)

(a4-1-20)
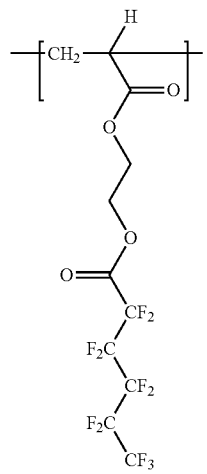
(a4-1-21)
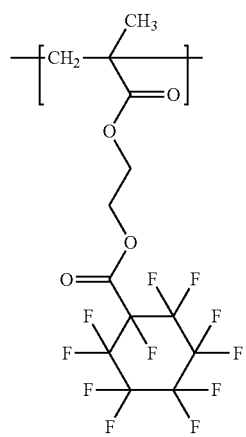
(a4-1-22)
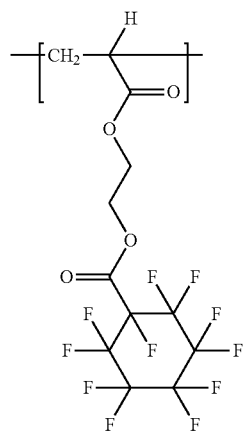
(a4-1'-1)
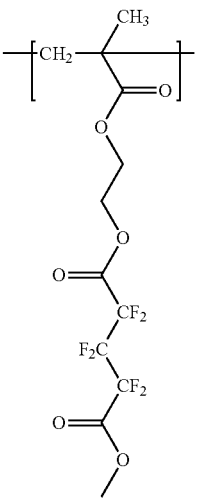
(a4-1'-2)
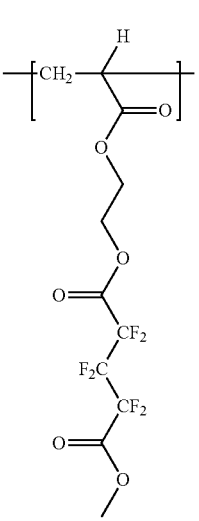
(a4-1'-3)
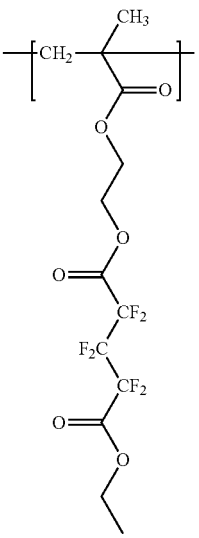
Examples of the structural unit represented by formula (a4-3) include structural units represented by formula (a4-1'-1) to formula (a4-1'-22).

(a4-1'-4)
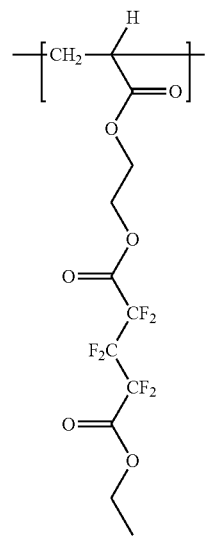
(a4-1'-5)
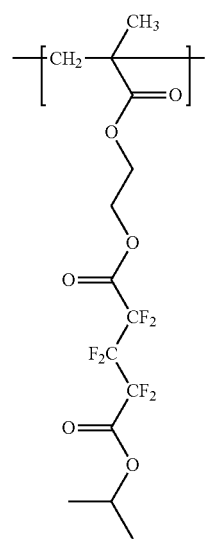
(a4-1'-6)
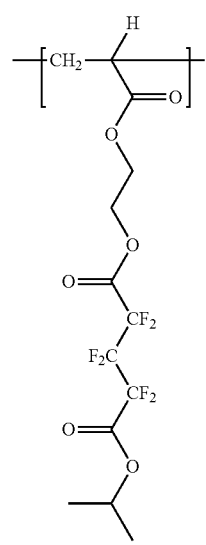
(a4-1'-7)
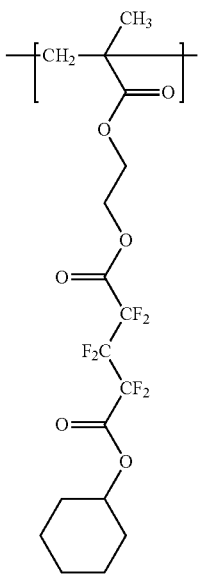
(a4-1'-8)
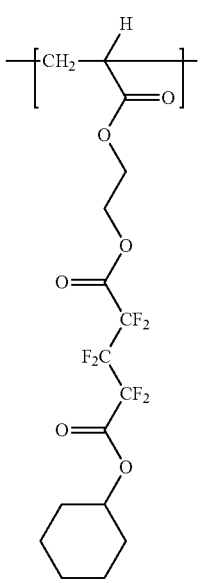

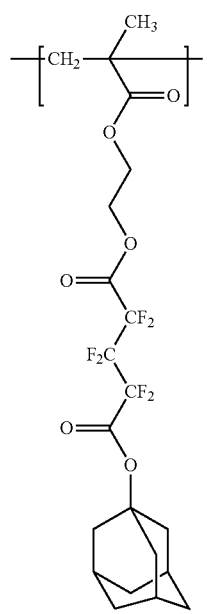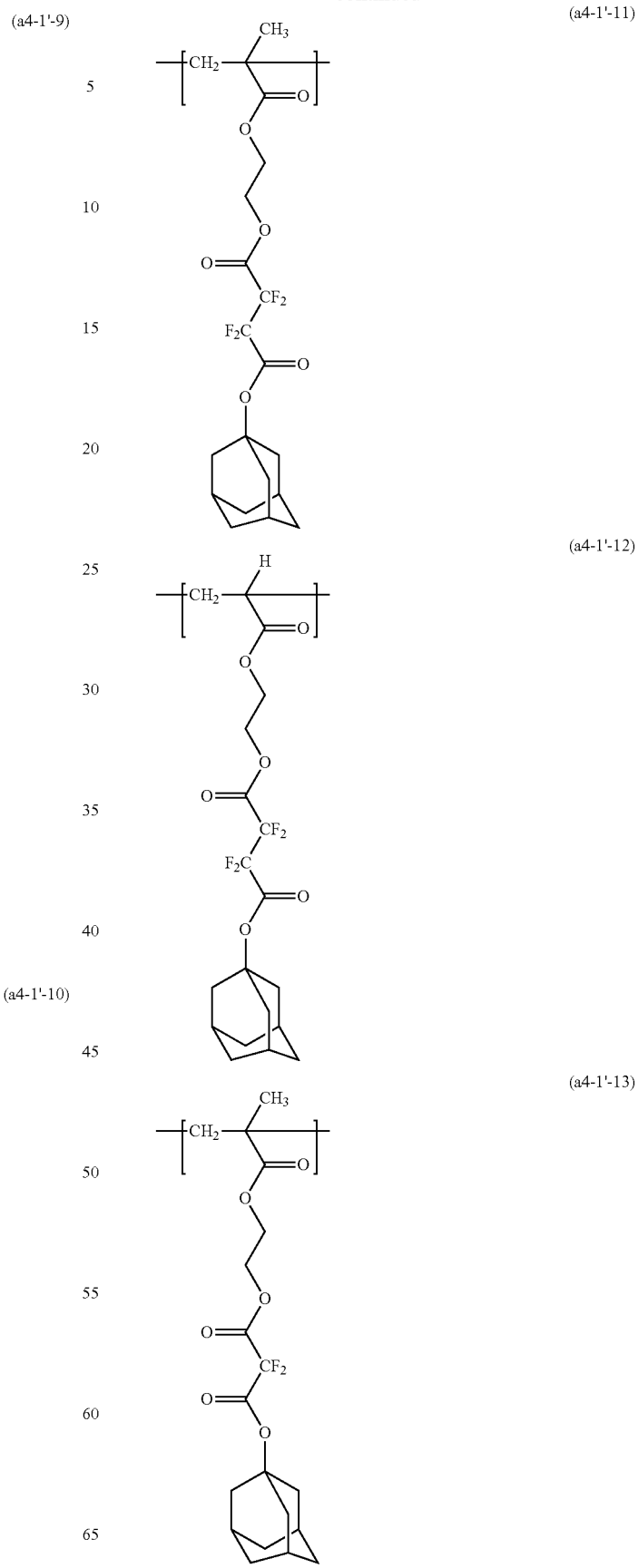

(a4-1'-14)
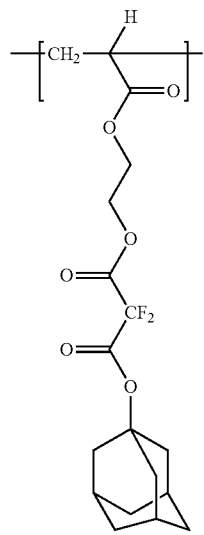
(a4-1'-15)
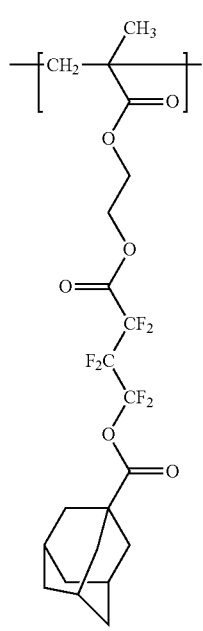
(a4-1'-16)
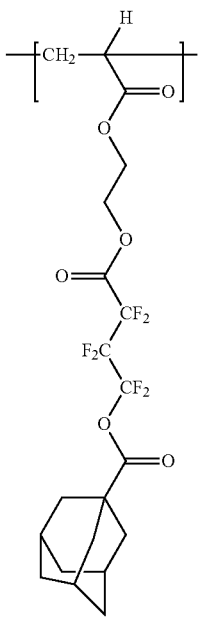
(a4-1'-17)
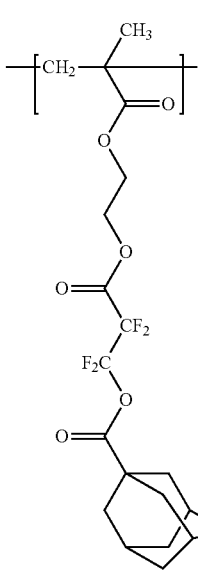

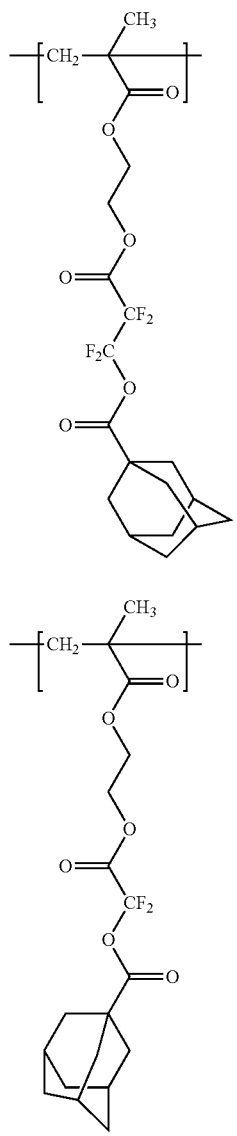

(a4-1'-18)

(a4-1'-19)

(a4-1'-20)

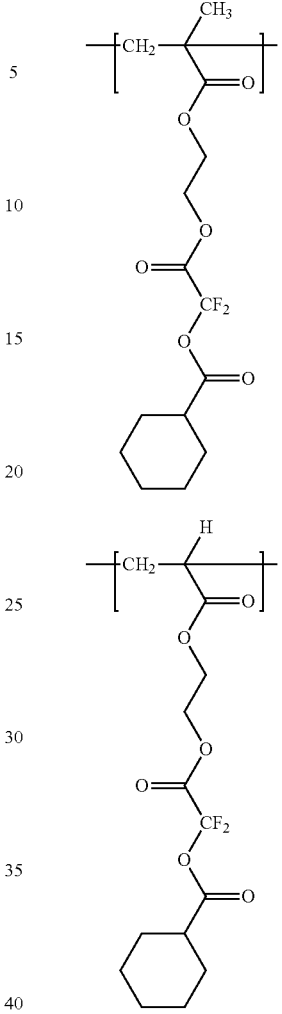

(a4-1'-21)

(a4-1'-22)

Examples of the structural unit (a4) include a structural unit represented by formula (a4-4):

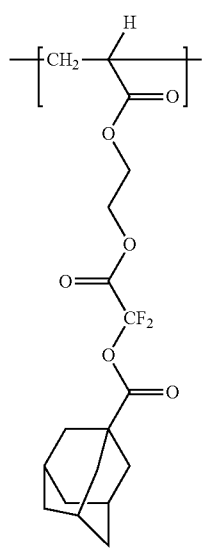

(a4-4)

wherein $R^{f21}$ represents a hydrogen atom or a methyl group, $A^{f21}$ represents *—$(CH_2)_{j1}$—, *—$(CH_2)_{j2}$—O—$(CH_2)_{j3}$— or *—$(CH_2)_{j4}$—CO—O—$(CH_2)_{j5}$—, where * represents a binding site to an oxygen atom, j1 to j5 each independently represents an integer of 1 to 6, and $R^{f22}$ represents a $C_1$ to $C_{10}$ hydrocarbon group having a fluorine atom.

Examples of the hydrocarbon group having a fluorine atom for $R'^{22}$ include the same ones as those for $R'^{2}$ in the formula (a4-2) $R'^{22}$ is preferably a $C_1$ to $C_{10}$ alkyl group having a fluorine atom or a $C_3$ to $C_{10}$ alicyclic hydrocarbon group having a fluorine atom, more preferably a $C_1$ to $C_{10}$ alkyl group having a fluorine atom, and still more preferably a $C_1$ to $C_6$ alkyl group having a fluorine atom.

In the formula (a4-4), $A'^{21}$ is preferably $-(CH_2)_{j1}-$, more preferably a methylene group or an ethylene group, and still more preferably a methylene group.

Examples of the structural unit represented by the formula (a4-4) include the following ones.

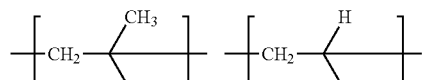

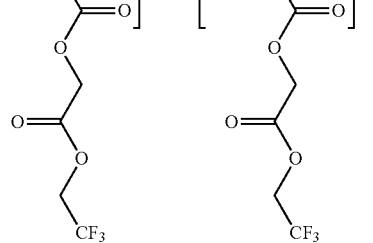

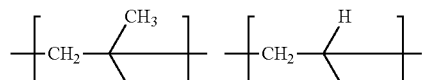

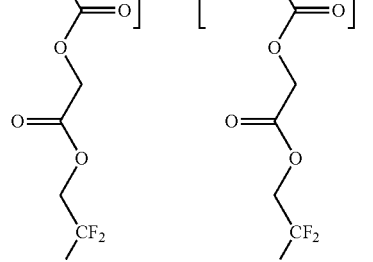

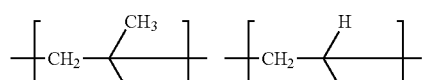

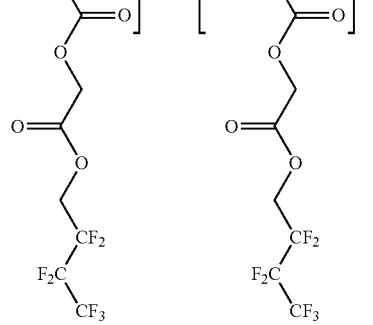

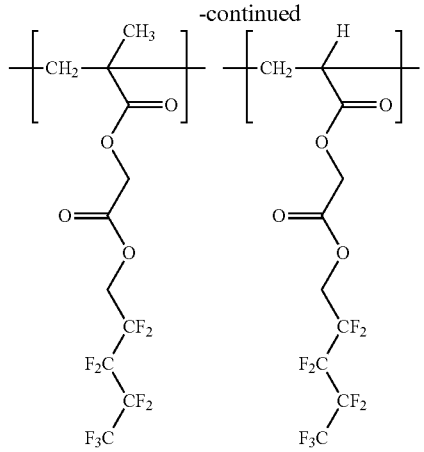

-continued

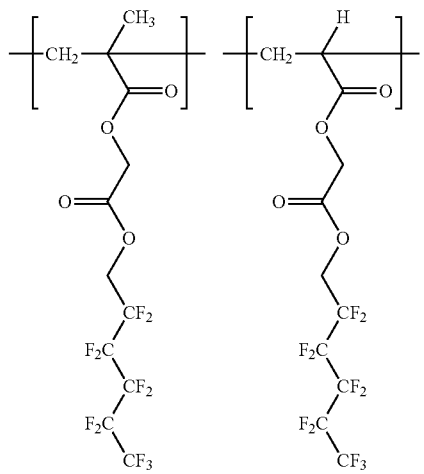

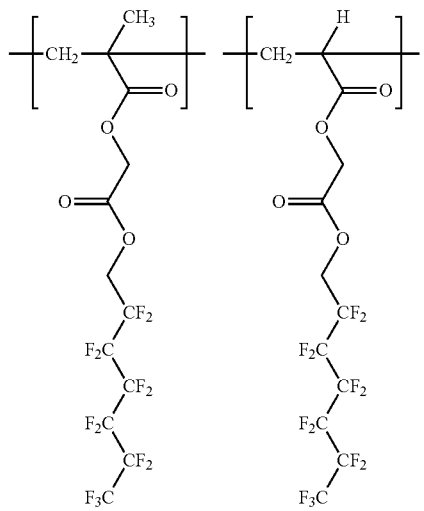

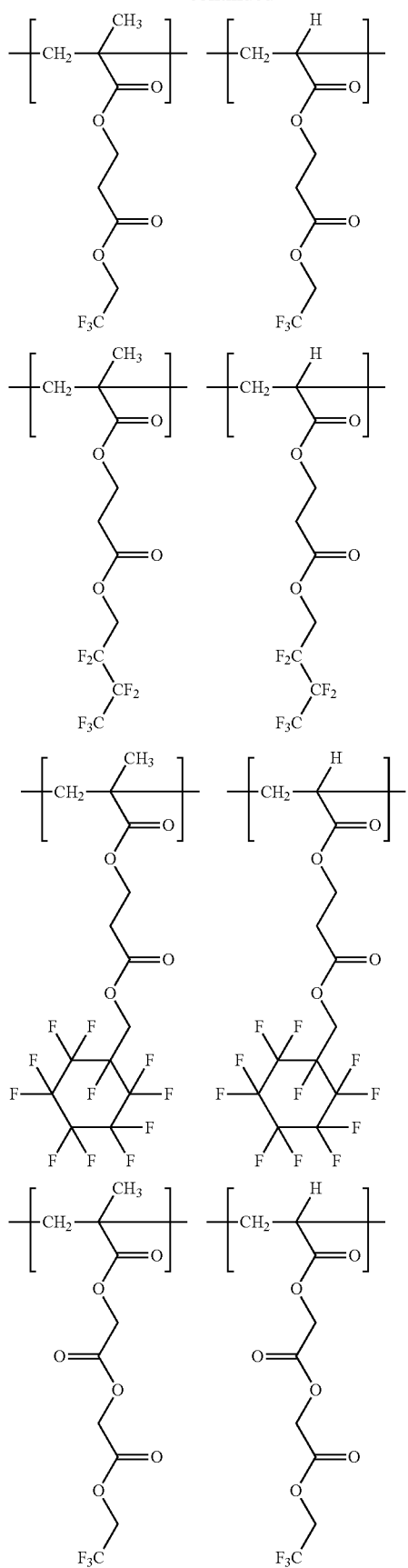

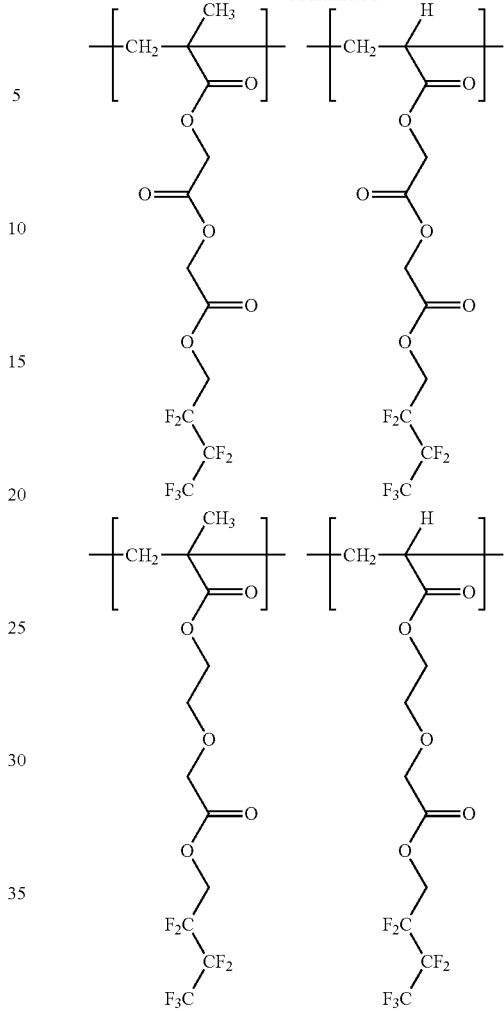

When Resin (A) has the structural unit (a4), the content thereof is usually 1 to 20% by mole, preferably 2 to 15% by mole, and more preferably 3 to 10% by mole, based on all the structural units of the resin.

The structural unit which has a hydrocarbon not being removed therefrom by action of an acid may have a linear, branched or cyclic hydrocarbon, preferably an alicyclic hydrocarbon group.

Examples of the structural unit having a hydrocarbon group not being removed therefrom by action of an acid include one represented by formula (a5-1):

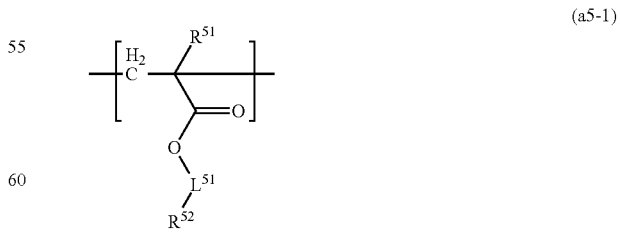

(a5-1)

where $R^{51}$ represents a hydrogen atom or a methyl group; $R^{52}$ represents a C3-C18 alicyclic hydrocarbon group, provided that the alicyclic hydrocarbon group has no substituent on the carbon atom bonded to $L^{51}$; and $L^{51}$ represents a single bond or a C1-C8 alkanediyl group where a methylene group can be replaced by an oxygen atom or carbonyl group.

The alicyclic hydrocarbon group represented by $R^{52}$ may be monocyclic or polycyclic one.

Examples of the alicyclic hydrocarbon group include a monocyclic hydrocarbon group such as a C3-C18 cycloalkyl group (e.g. a cyclopropyl group, a cyclobutyl group, a cyclopentyl group, a cyclohexyl group) and a polycyclic alicyclic hydrocarbon group such as an adamantyl group, or a norbornyl group.

Examples of the alicyclic hydrocarbon group having a substituent include a 3-hydroxyadamantyl group, and a 3-methyladamantyl group.

Examples of the $C_1$ to $C_8$ aliphatic hydrocarbon group include an alkyl group such as methyl, ethyl, n-propyl, isopropyl, n-butyl, sec-butyl, tert-butyl, n-pentyl, n-hexyl, n-heptyl, 2-ethylhexyl and n-octyl groups.

Examples of the alicyclic hydrocarbon group having a substituent for $R^{52}$ include 3-hydroxyadamantyl group and 3-methyladamantyl group.

$R^{52}$ is preferably an unsubstituted $C_3$ to $C_{18}$ alicyclic hydrocarbon group, and more preferably an adamantyl, norbornyl or cyclohexyl group.

Examples of the divalent saturated hydrocarbon group for $L^{51}$ include a divalent saturated aliphatic hydrocarbon group and a divalent saturated alicyclic hydrocarbon group, and a divalent saturated aliphatic hydrocarbon group is preferred.

Examples of the divalent saturated aliphatic hydrocarbon group include an alkanediyl group such as methylene, ethylene, propanediyl, butanediyl and pentanediyl groups.

Examples of the divalent saturated alicyclic hydrocarbon group include any of a monocyclic group and a polycyclic group.

Examples of the monocyclic group include a cycloalkanediyl group such as cyclopentanediyl and cyclohexanediyl groups. Examples of the polycyclic group include adamantanediyl and norbornanediyl groups.

Examples of the saturated hydrocarbon group in which a methylene group has been replaced by an oxygen atom or a carbonyl group include groups represented by formula (L1-1) to formula (L1-4).

In formula (L1-1) to formula (L1-4), * represents a binding site to an oxygen atom.

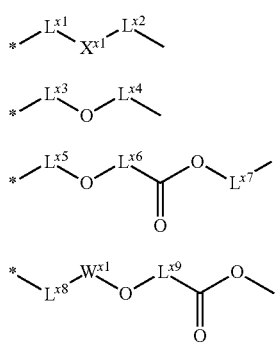

In the formulae, $X^{X1}$ represents an oxycarbonyl group or a carbonyloxy group, $L^{X1}$ represents a $C_1$ to $C_{16}$ divalent saturated aliphatic hydrocarbon group, $L^{X2}$ represents a single bond or a $C_1$ to $C_{15}$ divalent saturated aliphatic hydrocarbon group, provided that the total number of the carbon atoms contained in the groups of $L^{X1}$ and $L^{X2}$ is 16 or less;

$L^{X3}$ represents a single bond or a $C_1$ to $C_{17}$ divalent saturated aliphatic hydrocarbon group, $L^{X4}$ represents a single bond or a $C_1$ to $C_{16}$ divalent saturated aliphatic hydrocarbon group, provided that the total number of the carbon atoms contained in the groups of $L^{X3}$ and $L^{X4}$ is 17 or less;

$L^{X5}$ represents a $C_1$ to $C_{15}$ divalent saturated aliphatic hydrocarbon group, $L^{X6}$ and $L^{X7}$ each independently represent a single bond or a $C_1$ to $C_{14}$ divalent saturated aliphatic hydrocarbon group, provided that the total number of the carbon atoms contained in the groups of $L^{X5}$, $L^{X6}$ and $L^{X7}$ is 15 or less;

$L^{X8}$ and $L^{X9}$ each independently represent a single bond or a $C_1$ to $C_{12}$ divalent saturated aliphatic hydrocarbon group, $W^{X1}$ represents a $C_3$ to $C_{15}$ divalent saturated alicyclic hydrocarbon group, provided that the total number of the carbon atoms contained in the groups of $L^{X8}$, $L^{X9}$ and $W^{X1}$ is 15 or less.

$L^{X1}$ is preferably a $C_1$ to $C_8$ divalent saturated aliphatic hydrocarbon group, and more preferably a methylene group or an ethylene group.

$L^{X2}$ is preferably a single bond or a $C_1$ to $C_8$ divalent saturated aliphatic hydrocarbon group, and more preferably a single bond.

$L^{X3}$ is preferably a $C_1$ to $C_8$ divalent saturated aliphatic hydrocarbon group.

$L^{X4}$ is preferably a single bond or a $C_1$ to $C_8$ divalent saturated aliphatic hydrocarbon group.

$L^{X5}$ is preferably a $C_1$ to $C_8$ divalent saturated aliphatic hydrocarbon group, and more preferably a methylene group or an ethylene group.

$L^{X6}$ is preferably a single bond or a $C_1$ to $C_8$ divalent saturated aliphatic hydrocarbon group, and more preferably a methylene group or an ethylene group.

$L^{X7}$ is preferably a single bond or a $C_1$ to $C_8$ divalent saturated aliphatic hydrocarbon group.

$L^{X8}$ is preferably a single bond or a $C_1$ to $C_8$ divalent saturated aliphatic hydrocarbon group, and more preferably a single bond or a methylene group.

$L^{X9}$ is preferably a single bond or a $C_1$ to $C_8$ divalent saturated aliphatic hydrocarbon group, and more preferably a single bond or a methylene group.

$W^{X1}$ is preferably a $C_3$ to $C_{10}$ divalent saturated alicyclic hydrocarbon group, and more preferably a cyclohexanediyl or adamantanediyl group.

Examples of the group represented by the formula (L1-1) include the following ones.

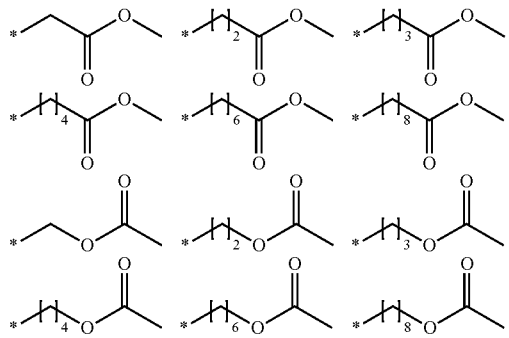

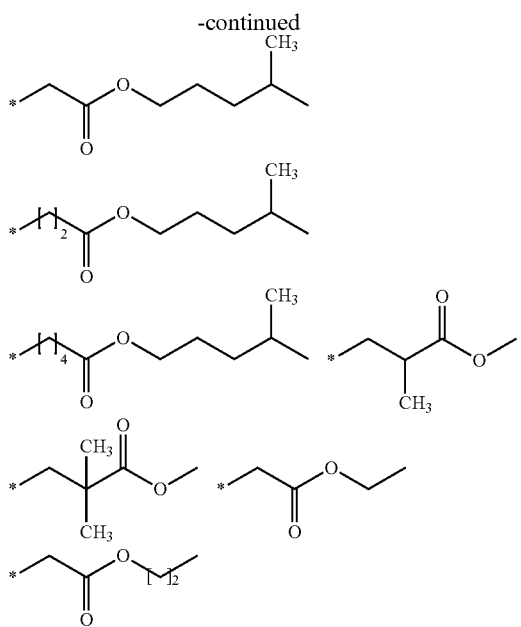

Examples of the group represented by the formula (L1-2) include the following ones.

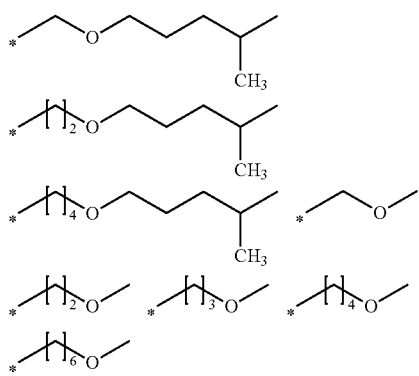

Examples of the group represented by the formula (L1-3) include the following ones.

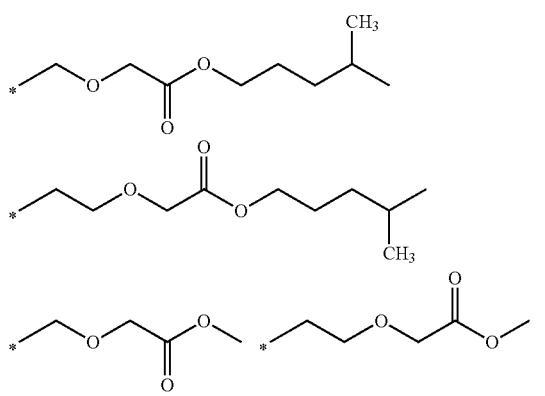

Examples of the group represented by the formula (L1-4) include the following ones.

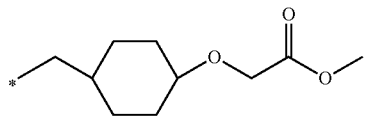
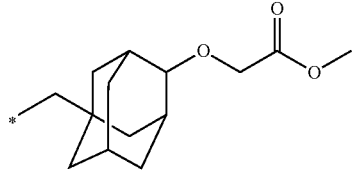
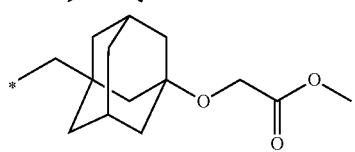
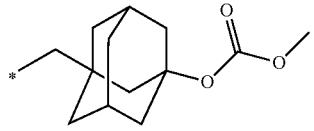
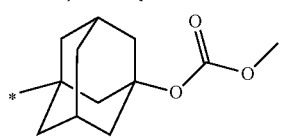

$L^{51}$ is preferably a single bond, a $C_1$ to $C_8$ divalent saturated hydrocarbon group or the group represented by the formula (L1-1), more preferably a single bond, a C1 to C6 divalent saturated hydrocarbon group or the group represented by the formula (L1-1).

Examples of the structural unit represented by formula (a5-1) include the following ones.

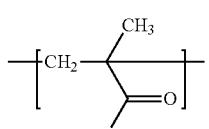 (a5-1-1)

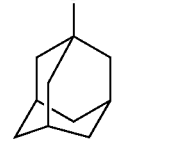 (a5-1-2)

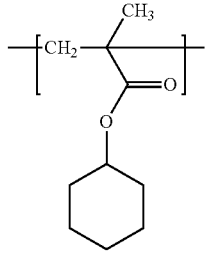

-continued
(a5-1-3)
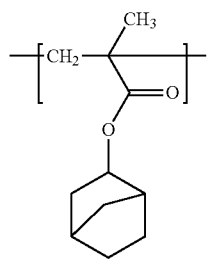
(a5-1-4)
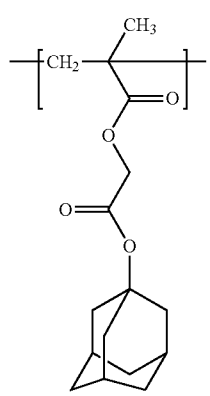
(a5-1-5)
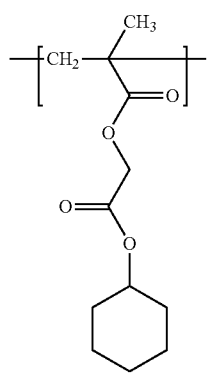
(a5-1-6)
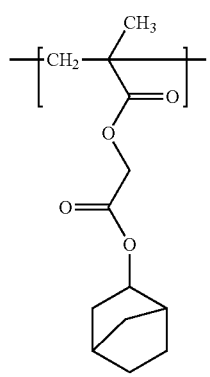
-continued
(a5-1-7)
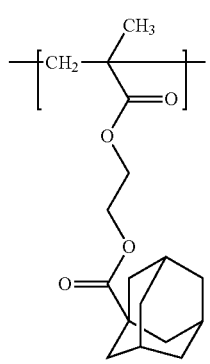
(a5-1-8)
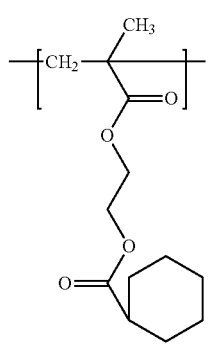
(a5-1-9)
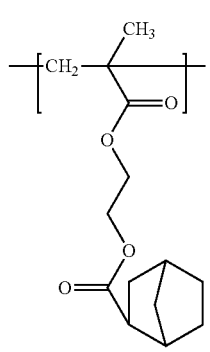
(a5-1-10)
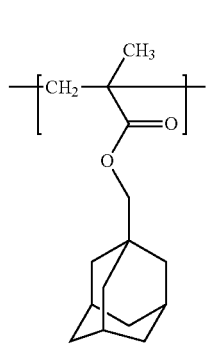

(a5-1-11) 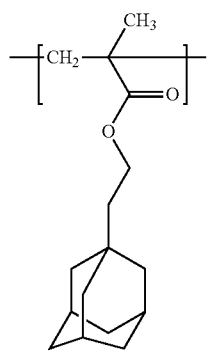

(a5-1-12) 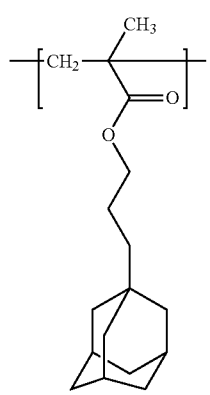

(a5-1-13) 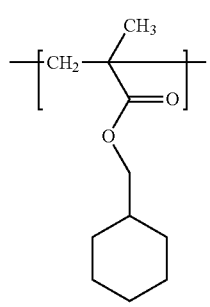

(a5-1-14) 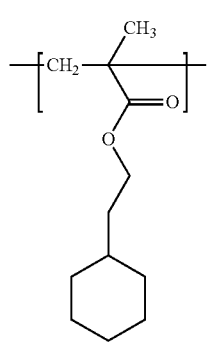

(a5-1-15) 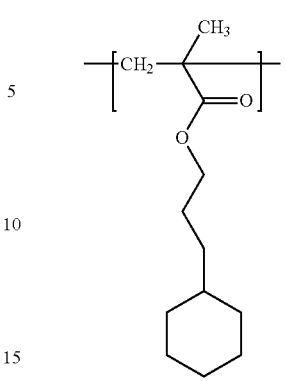

(a5-1-16) 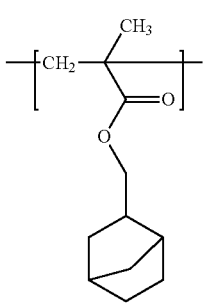

(a5-1-17) 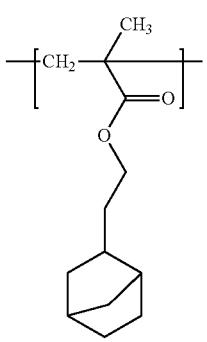

(a5-1-18) 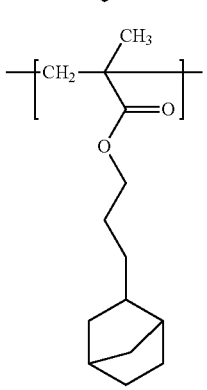

Examples of the structural units represented by formula (a5-1) include structural units represented by the above formulae in which a methyl group corresponding to $R^{51}$ has been replaced by a hydrogen atom.

When the resin (A) further has the structural unit represented by formula (a5), the content thereof is preferably 1 to 30% by mole, more preferably 2 to 20% by mole, and still more preferably 3 to 15% by mole, based on all the structural units of the resin.

Resin (A) has preferably the structural unit (a) and the structural unit having no acid-labile group.

In Resin (A), the structural unit (a1) is one of the structural unit (a1-1) and the structural unit (a1-2), more preferably the structural unit (a1-2). The structural unit (a1-2) is preferably which comprises a cyclohexyl group or a cyclopentyl group.

The structural unit having no acid-labile group is preferably one of the structural unit (a2) and the structural unit (a3). The structural unit (a2) is preferably the structural unit (a2-1). The structural unit (a3) is preferably one of the structural unit (a3-1), the structural unit (a3-2) and the structural unit (a3-4). Resin (A) has preferably the structural unit (a1-1). The content of the structural unit (a1-1) is preferably 15% by mole or more of the total amount of the structural unit (a). The more is the structural unit having an adamantyl group, the more improved is the resistance of the photoresist film to dry etching.

Resin (A) can be produced according to known polymerization methods such as radical polymerization, using monomers corresponding to the structural units as mentioned above.

The resin has usually 2,000 or more of the weight-average molecular weight, preferably 2,500 or more of the weight-average molecular weight, more preferably 3,000 or more of the weight-average molecular weight. The resin has usually 50,000 or less of the weight-average molecular weight, preferably more 30,000 or less of the weight-average molecular weight, and preferably more 15,000 or less of the weight-average molecular weight.

The weight-average molecular weight can be measured with gel permeation chromatography.

The photoresist composition of the disclosure may further contain another resin than Resin (A).

Examples of another resin than Resin (A) include what consists of structural units having no acid-labile group, preferably what comprises, not the structural unit (a1), but the structural unit (a4). Here, another resin than Resin (A) is sometimes referred to as "Resin (X)".

Resin (X) may be one which consists of the structural unit (a4), or one which further has the structural unit (a2), the structural unit (a3) or another structural unit having no acid-labile group, known in the art.

Resin (X), the content of the structural unit (a4) is preferably 40% by mole or more, more preferably 45% by mole or more, still more preferably 50% by mole or more, based on all the structural units of the resin.

Resin (X) usually has 6000 or more of the weight-average molecular weight, preferably 7000 or more of the weight-average molecular weight. The resin usually has 80,000 or less of the weight-average molecular weight, preferably has 60,000 or less of the weight-average molecular weight.

The weight-average molecular weight can be measured with known methods such as liquid chromatography or gas chromatography.

Resin (X) can be produced according to known polymerization methods such as radical polymerization, using monomers corresponding to the structural units as mentioned above.

When the photoresist composition contains Resin (X), the content of the resin is preferably 1 to 60 weight parts, more preferably 1 to 50 weight parts, and still more preferably 1 to 40 weight parts, and further still more preferably 2 to 30 weight parts, relative to 100 parts of Resin (A).

The total content of the resins in the photoresist composition is usually 80% by mass or more based on sum of the solid components, and usually 99% by mass or less.

In this specification, "solid component" means components other than solvent in the photoresist composition.

The photoresist composition of the disclosure may further contain a solvent.

The amount of the solvent is usually 90% by weight or more, preferably 92% by weight or more preferably 94% by weight or more based on total amount of the photoresist composition. The amount of the solvent is usually 99.9% by weight or less and preferably 99% by weight or less based on total amount of the photoresist composition. The content can be measured with known methods such as liquid chromatography or gas chromatography.

Examples of the solvent include a glycol ether ester such as ethyl cellosolve acetate, methyl cellosolve acetate and propylene glycol monomethyl ether acetate; a glycol ether such as propylene glycol monomethyl ether; an ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone.

The photoresist compositions of the disclosure may further contain a quencher. The "quencher" has the property that it can trap an acid, especially an acid generated from the acid generator by applying a radiation.

Examples of the quencher include a basic nitrogen-containing organic compound and a weak acid salt.

Examples of the basic nitrogen-containing organic compound include an amine compound such as an aliphatic amine, an aromatic amine and an ammonium salt. Examples of the aliphatic amine include a primary amine, a secondary amine and a tertiary amine. Examples of the aromatic amine include an aromatic amine in which an aromatic ring has an amino group such as aniline and a heteroaromatic amine such as pyridine.

Examples of the quencher include 1-naphthylamine, 2-naphthylamine, aniline, diisopropylaniline, 2-, 3- or 4-methylaniline, 4-nitroaniline, N-methylaniline, N,N-dimethylaniline, diphenylamine, hexylamine, heptylamine, octylamine, nonylamine, decylamine, dibutylamine, pentylamine, dioctylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethyldipentylamine, ethyldihexylamine, ethyldiheptylamine, ethyldioctylamine, ethyldinonylamine, ethyldidecylamine, dicyclohexylmethylamine, 2-tris[2-(2-methoxyethoxy)ethyl]amine, triisopropanolamine, ethylenediamine, tetramethylenediamine, hexamethylenediamine, 4,4'-diamino-1,2-diphenylethane, 4,4'-diamino-3,3'-dimethyldiphenylmethane, 4,4'-diamino-3,3'-diethyldiphenyl methane, piperazine, morpholine, piperidine, hindered amine compound having a piperidine structure, 2,2'-methylenebisaniline, imidazole, 4-methylimidazole, pyridine, 4-methylpyridine, 1,2-di(2-pyridyl)ethane, 1,2-di(4-pyridyl)ethane, 1,2-di(2-pyridyl)ethene, 1,2-di(4-pyridyl)ethene, 1,3-di(4-pyridyl) propane, 1,2-di(4-pyridyloxy) ethane, di(2-pyridyl) ketone, 4,4'-dipyridyl sulfide, 4,4'-dipyridyl disulfide, 2,2'-dipyridylamine, 2,2'-dipicolylamine and bipyridine.

Examples of the quaternary ammonium salts include tetramethylammonium hydroxide, tetrabutylammonium hydroxide, tetrahexylammonium hydroxide, tetraoctylammonium hydroxide, phenyltrimethylammonium hydroxide, (3-trifluoromethylphenyl)trimethylammonium hydroxide and (2-hydroxyethyl)trimethylammonium hydroxide (so-called "choline").

The weak acid salt is usually lower in acidity than the acid generator as mentioned above and Salt (I), examples of which include carboxylic acid salts and sulfonic acid salts.

The acidity in the weak acid salt is shown by the acid dissociation constant (pKa).

The acid dissociation constant of acid generated from the weak acid salt is usually salt of −3<pKa.

The weak acid salt is preferably a salt of −1<pKa<7, and more preferably a salt of 0<pKa<5.

Specific examples of the weak acid salt include JP2012-229206A1, JP2012-6908A1, JP2011-191745A1, JP2012-72109A1, JP2011-39502A1 and the following ones.

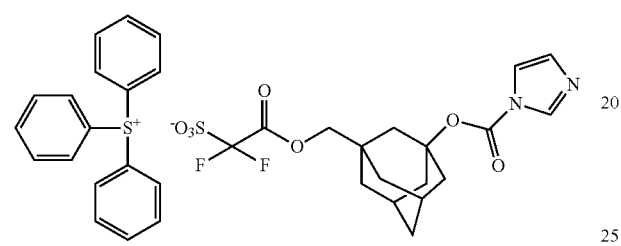

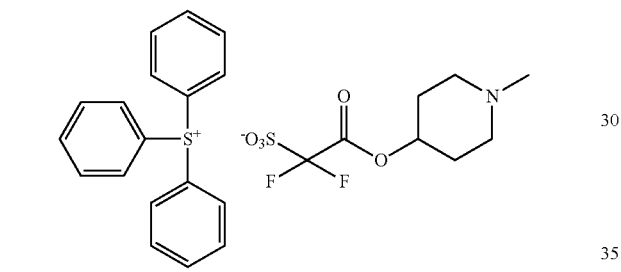

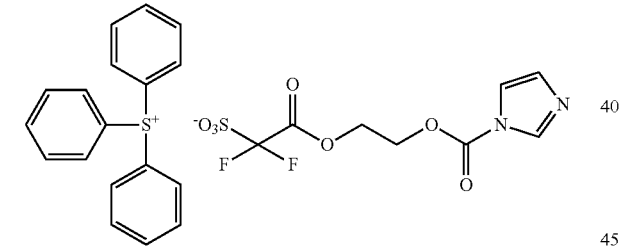

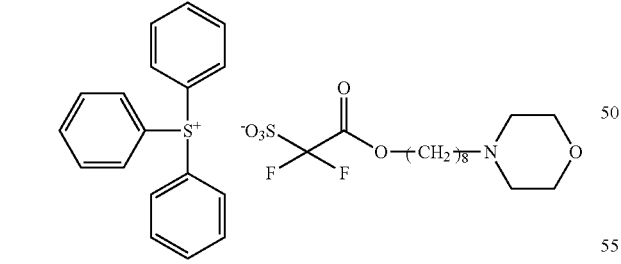

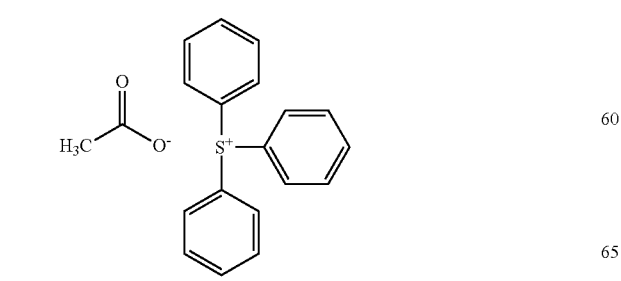

-continued

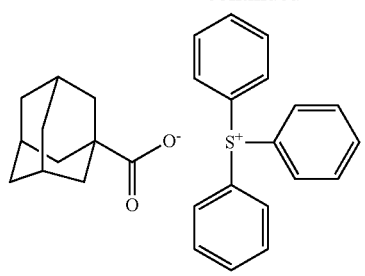

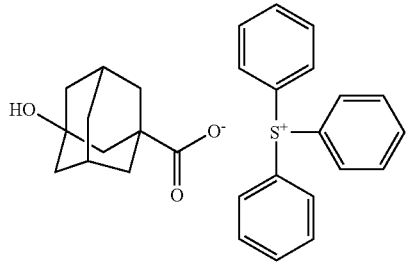

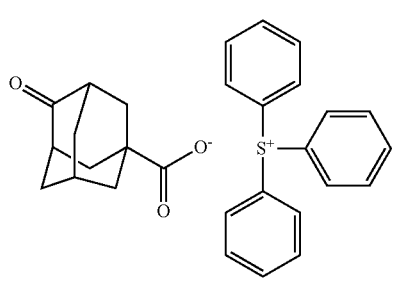

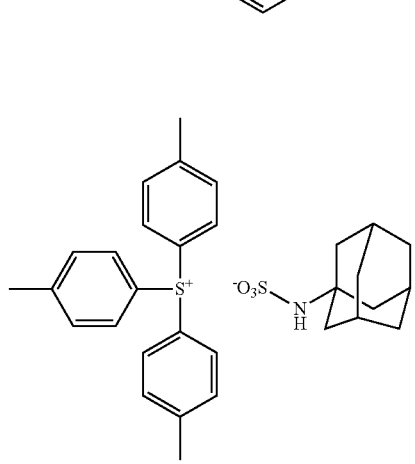

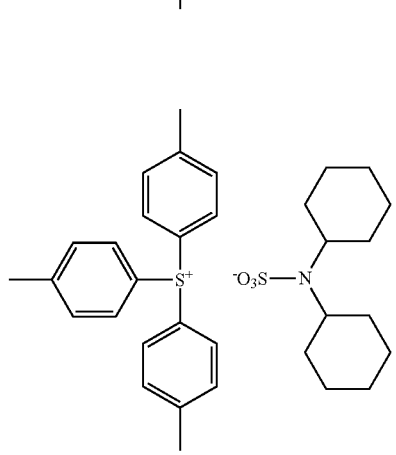

-continued

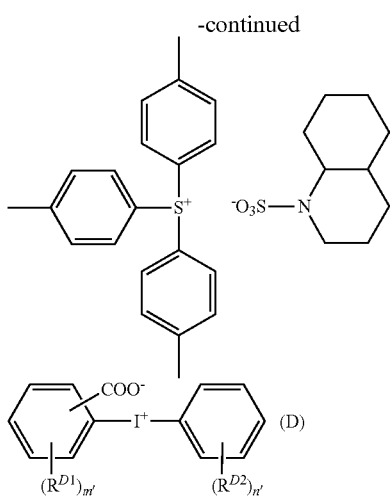

In the formula (D), $R^{D1}$ and $R^{D2}$ in each occurrence independently represent a $C_1$ to $C_{12}$ hydrocarbon group, a $C_1$ to $C_6$ alkoxyl group, a $C_2$ to $C_7$ acyl group, a $C_2$ to $C_7$ acyloxy group, a $C_2$ to $C_7$ alkoxycarbonyl group, a nitro group or a halogen atom;

m' and n' each independently represent an integer of 0 to 4.

Examples of the hydrocarbon group for $R^{D1}$ and $R^{D2}$ include any of an aliphatic hydrocarbon group, an alicyclic hydrocarbon group, an aromatic hydrocarbon group and a combination thereof.

Examples of the aliphatic hydrocarbon group include an alkyl group such as methyl, ethyl, propyl, isopropyl, butyl, isobutyl, tert-butyl, pentyl, hexyl and nonyl groups.

The alicyclic hydrocarbon group is any one of monocyclic or polycyclic hydrocarbon group, and saturated or unsaturated hydrocarbon group. Examples thereof include a cycloalkyl group such as cyclopropyl, cyclobutyl, cyclopentyl, cyclohexyl, cyclononyl and cyclododecyl groups; adamantyl and norbornyl groups.

Examples of the aromatic hydrocarbon group include an aryl group such as phenyl, 1-naphthyl, 2-naphthyl, 2-methylphenyl, 3-methylphenyl, 4-methylphenyl, 4-ethylphenyl, 4-propylphenyl, 4-isopropylphenyl, 4-butylphenyl, 4-tert-butylphenyl, 4-hexylphenyl, 4-cyclohexylphenyl, anthryl, p-adamantylphenyl, tolyl, xylyl, cumenyl, mesityl, biphenyl, phenanthryl, 2,6-diethylphenyl and 2-methyl-6-ethylphenyl groups.

Examples of the combination thereof include an alkylcycloalkyl, a cycloalkyl-alkyl, aralkyl (e.g., phenylmethyl, 1-phenylethyl, 2-phenylethyl, 1-phenyl-1-propyl, 1-phenyl-2-propyl, 2-phenyl-2-propyl, 3-phenyl-1-propyl, 4-phenyl-1-butyl, 5-phenyl-1-pentyl and 6-phenyl-1-hexyl groups) groups.

Examples of the alkoxyl group include methoxy and ethoxy groups.

Examples of the acyl group include acetyl, propanonyl, benzoyl and cyclohexanecarbonyl groups.

Examples of the acyloxy group include a group in which oxy group (—O—) bonds to an acyl group.

Examples of the alkoxycarbonyl group include a group in which the carbonyl group (—CO—) bonds to the alkoxy group.

Example of the halogen atom is a chlorine atom, a fluorine atom and bromine atom.

In the formula (D), $R^{D1}$ and $R^{D2}$ in each occurrence independently preferably represent a $C_1$ to $C_8$ alkyl group, a $C_3$ to $C_{10}$ cycloalkyl group, a $C_1$ to $C_6$ alkoxyl group, a $C_2$ to $C_4$ acyl group, a $C_2$ to $C_4$ acyloxy group, a $C_2$ to $C_4$ alkoxycarbonyl group, a nitro group or a halogen atom.

m' and n' independently preferably represent an integer of 0 to 3, more preferably an integer of 0 to 2, and more preferably 0.

Specific examples of the salt of the formula (D) include compounds below.

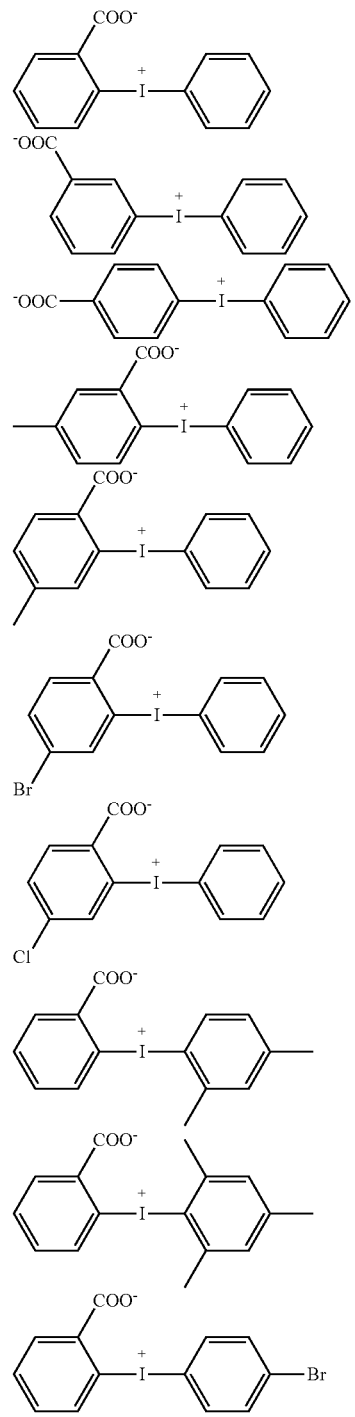

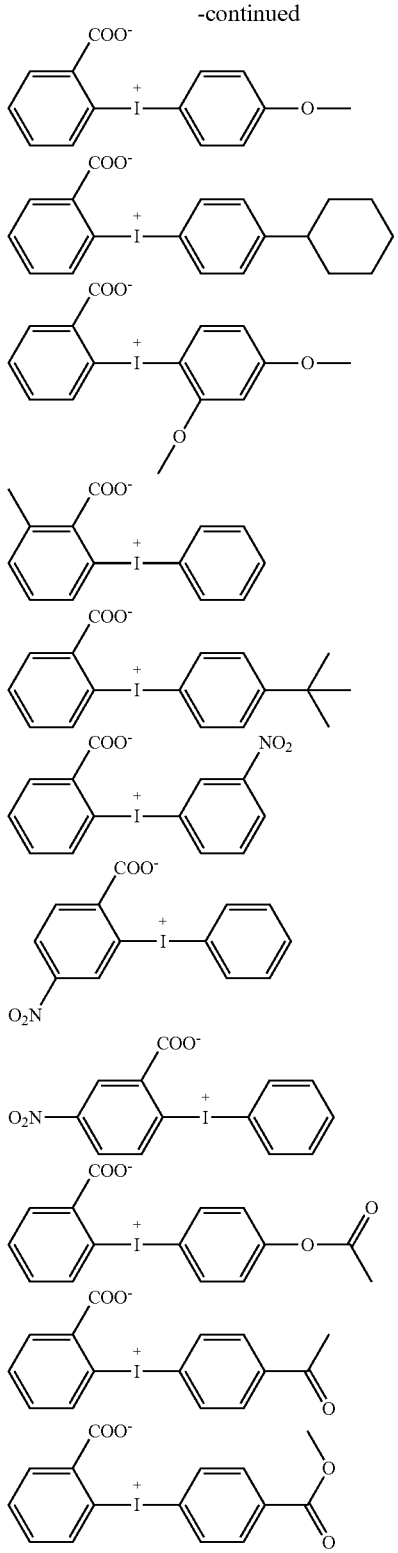

The content of quencher is preferably 0.01 to 5% by mass, more preferably 0.01 to 4% by mass, and still more preferably 0.01 to 3% by mass, based on sum of the solid components.

The photoresist compositions of the disclosure may further contain, if necessary, a small amount of various additives known in the art such as a sensitizer, a dissolution inhibitor, other polymers, a surfactant, a stabilizer and a dye.

The photoresist compositions of the disclosure can usually be prepared by mixing, in a solvent, Salt (I) and Resin (A), and if necessary a known acid generator, a quencher, and/or additives at a suitable ratio for the composition, optionally followed by filtrating the mixture with a filter having 0.003 µm to 0.2 µm of a pore size.

The order of mixing these components is not limited to any specific order. The temperature at mixing the components is usually 10 to 40° C., which can be selected in view of the resin or the like.

The mixing time is usually 0.5 to 24 hours, which can be selected in view of the temperature. The means for mixing the components is not limited to specific one. The components can be mixed by being stirred.

The amounts of the components in the photoresist compositions can be adjusted by selecting the amount to be used for production of them.

The photoresist compositions of the disclosure are useful for a chemically amplified photoresist composition.

The photoresist compositions of the disclosure are useful for a chemically amplified photoresist composition.

A photoresist pattern can be produced by the following steps (1) to (5):

(1) a step of applying the photoresist composition of the disclosure on a substrate, (2) a step of forming a composition film by conducting drying, (3) a step of exposing the composition film to radiation, (4) a step of baking the exposed composition film, and (5) a step of developing the baked composition film with an alkaline developer.

The applying of the photoresist composition on a substrate is usually conducted using a conventional apparatus such as spin coater. The photoresist composition is preferably filtrated with filter having a pore size of 0.01 to 0.2 µm before applying. Examples of the substrate include a silicon wafer or a quartz wafer on which a sensor, a circuit, a transistor or the like is formed.

The formation of the composition film is usually conducted using a heating apparatus such as hot plate or a decompressor, and the heating temperature is usually 50 to 200° C. When the pressure is reduced during heating, the operation pressure is usually 1 to $1.0*10^5$ Pa. The heating time is usually 10 to 180 seconds.

The composition film obtained is exposed to radiation using an exposure system. The exposure is usually conducted through a mask having a pattern corresponding to the desired photoresist pattern. Examples of the exposure source include a light source radiating laser light in a UV-region such as a KrF excimer laser (wavelength: 248 nm), an ArF excimer laser (wavelength: 193 nm) and a $F_2$ laser (wavelength: 157 nm), and a light source radiating harmonic laser light in a far UV region or a vacuum UV region by wavelength conversion of laser light from a solid laser light source (such as YAG or semiconductor laser).

The temperature of baking of the exposed composition film is usually 50 to 200° C., and preferably 70 to 150° C.

The development of the baked composition film is usually carried out using a development apparatus. The development method includes dipping methods, paddle methods, spray methods and dynamic dispense method. The developing temperature is preferably 5 to 60° C., and the developing time is preferably 5 to 300 seconds.

The positive and negative type photoresist patterns can be obtained by the development depending on a developer to be used therefor.

When a positive type photoresist pattern is prepared from the photoresist composition of the disclosure, the development can be conducted with an alkaline developer. The alkaline developer to be used may be any one of various aqueous alkaline solution used in the art. Generally, an aqueous solution of tetramethylammonium hydroxide or (2-hydroxyethyl)trimethylammonium hydroxide (commonly known as "choline") is often used. The alkaline developer may contain a surfactant.

After development, the photoresist film having photoresist pattern is preferably washed with ultrapure water, and the remained water on the photoresist film and the substrate is preferably removed therefrom.

When a negative type photoresist pattern is prepared from the photoresist composition of the disclosure, the development can be conducted with a developer containing an organic solvent, such developer is sometimes referred to as "organic developer". Examples of an organic solvent for organic developer include ketone solvents such as 2-hexanone, 2-heptanone; glycolether ester solvents such as propyleneglycolmonomethylether acetate; ester solvents such as butyl acetate; glycolether solvents such as propyleneglycolmonomethylether; amide solvents such as N,N-dimethylacetamide; and aromatic hydrocarbon solvents such as anisole.

The content of organic solvent is preferably from 90% to 100% by weight, more preferably from 95% to 100% by weight, in an organic developer. Preferred is that the organic developer essentially consists of an organic solvent.

Among them, the organic developer is preferably a developer comprising butyl acetate and/or 2-heptanone.

The total content of butyl acetate and 2-heptanone is preferably from 50% to 100% by weight, more preferably from 90% to 100% by weight. Preferred is that the organic developer essentially consists of butyl acetate and/or 2-heptanone.

The organic developer may comprise a surfactant or a very small amount of water.

Development with an organic developer can be stopped by replacing the developer by other solvent than it such as alcohol.

The photoresist composition of the disclosure provides is suitable for KrF excimer laser lithography, ArF excimer laser lithography, EUV (extreme ultraviolet) lithography and EB (electron beam) lithography, particularly for ArF excimer laser lithography.

EXAMPLES

The invention as mentioned above will be described more specifically by Examples, which are not construed to limit the scope of the disclosure.

The "%" and "part(s)" used to represent the content of any component and the amount of any material used in the following examples and comparative examples are on a mass basis unless otherwise specifically noted.

The weight-average molecular weight of any material used in the following examples is determined with gel permeation chromatography under the following condition.

Equipment: HLC-8120 GCP type, manufactured by TOSOH CORPORATION

Column: Three of TSKgel Multipore HXL-M with guard column, manufactured by TOSOH CORPORATION Solvent: tetrahydrofuran
Flow rate: 1.0 mL/min.
Detector: RI Detector
Column temperature: 40° C.
Injection volume: 100 μL
Standard reference material: Standard polystyrene (manufactured by TOSOH CORPORATION)

Structures of compounds were determined by mass spectrometry (Liquid Chromatography: 1100 Type, manufactured by AGILENT TECHNOLOGIES LTD., Mass Spectrometry: LC/MSD Type, manufactured by AGILENT TECHNOLOGIES LTD.).

Here, the values at the peaks of spectrum are referred to as "MASS."

Example 1

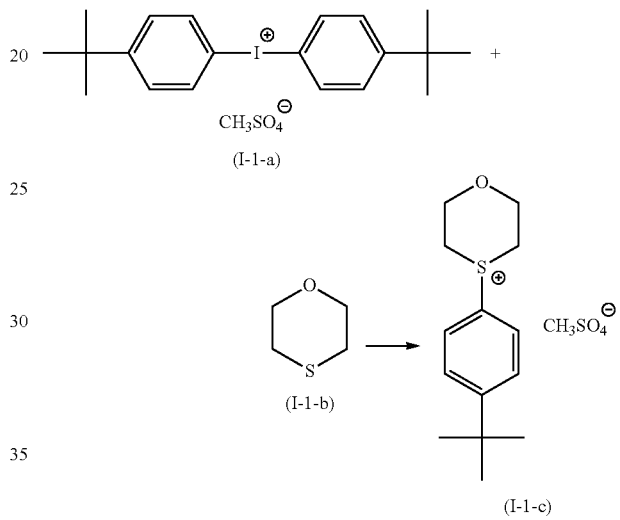

To a reactor, 50 parts of the salt represented by the formula (I-1-a), 10.33 parts of the compound represented by the formula (I-1-b) and 350 parts of chloroform were added and then they were stirred at 23° C. for 30 minutes.

To the resulting mixture, 0.2 parts of copper (II) dibenzoate was added and refluxed at 80° C. for 2 hours, followed by being concentrated.

To the obtained concentrate, 440 parts of tert-butylmethylether were added and the obtained mixture was stirred, followed by being filtrated to obtain 32.96 parts of the salt represented by the formula (I-1-c).

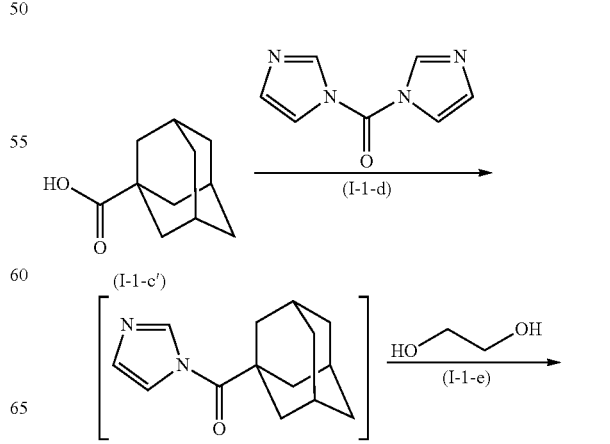

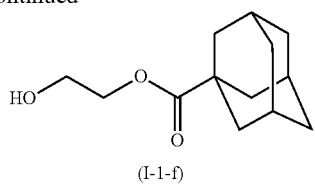

(I-1-f)

After mixing 12.3 parts of the salt represented by the formula (I-1-c') and 40 parts of acetonitrile, they were stirred at 23° C. for 30 minutes. To the mixture, 11.63 parts of the compound represented by the formula (I-1-d) was added, and then stirred at 40° C. for 1 hour. To the reaction mixture, a mixed solution containing 8.47 parts of the salt represented by the formula (I-1-e) and 20 parts of acetonitrile, followed by being stirred at 23° C. for 3 hours. The obtained mixture was concentrated, and then separated using column [silica gel 60N (spherical shape, neutral), 100 to 210 μm, eluent: mixture of n-heptane and ethyl acetate (n-heptane/ethyl acetate=1/2)] to obtain 9.95 parts of the compound represented by the formula (I-1-f).

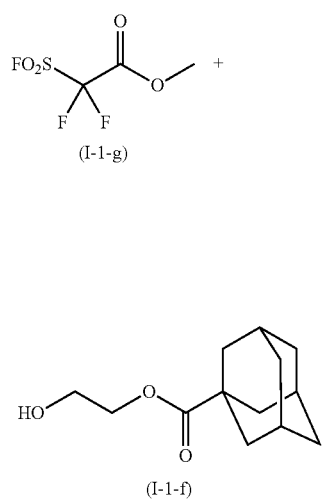

Into the reactor, 3 parts of the compound represented by the formula (I-1-g), 5.16 parts of the compound represented by the formula (I-1-f), 80 parts of chloroform and 1.34 parts of the compound represented by the formula (I-1-h) were fed and stirred at 23° C. for 30 minutes, followed by being refluxed at 80° C. for 5 hours while removing water which was generated by the reflux. After the reflux, the obtained mixture was cooled to 23° C., and 6.7 parts of silica gel was added thereto and stirred at 23° C. for 30 minutes, followed by being filtrated. The obtained filtrate was concentrated to obtain 5.23 parts of the salt represented by the formula (I-1-i).

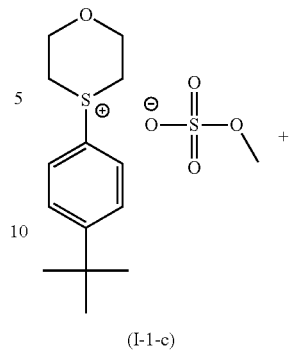

(I-1-c)

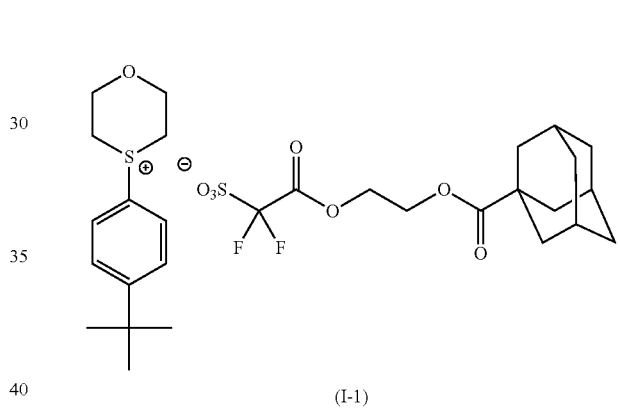

(I-1-i)

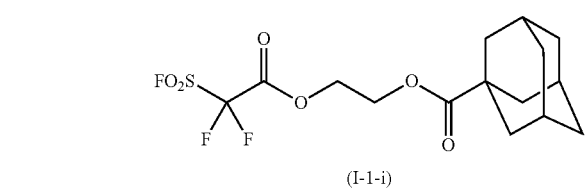

(I-1)

Into a reactor, 5.68 parts of the compound represented by the formula (I-1-c), 57.1 parts of chloroform, 19.9 parts of ion-exchanged water and 3.02 parts of triethylamine were added and stirred at 23° C. for 30 minutes, followed by being cooled to 5° C.

To the obtained mixture, a mixed solution of 5.22 parts of the compound represented by the formula (I-1-i) and 5.22 parts of chloroform was dropped for 30 minutes, and stirred at 23° C. for one hour, followed by separating an organic layer.

To the obtained organic layer, 33 parts of 5% aqueous oxalic acid solution was added, stirred at 23° C. for 30 minutes, followed by separating an organic layer. To the obtained organic layer, 33 parts of ion-exchanged water was added and stirred at 23° C. for 30 minutes, followed by separating an organic layer. The washing step with water was conducted three times. The washed organic layer was concentrated. To the obtained residue, 30 parts of tert-butylmethylether was added and removed supernatant therefrom.

The obtained residue was concentrated to obtain 4.51 parts of the salt represented by formula (I-1).

MS (ESI(+) Spectrum): M$^+$ 237.1
MS (ESI(−) Spectrum): M$^-$ 381.1

Example 2

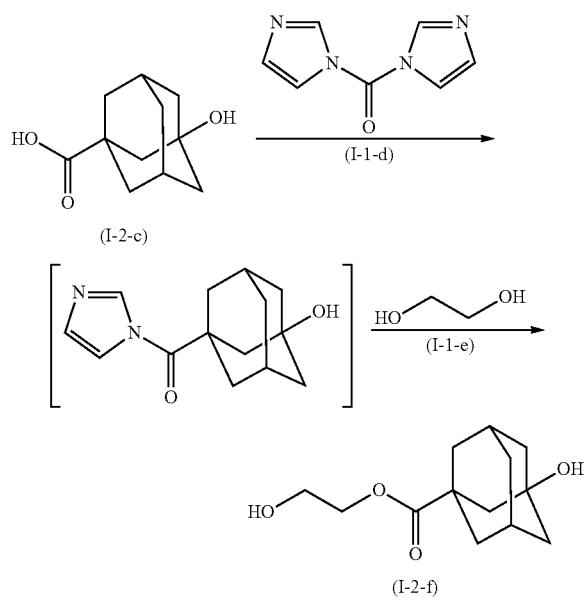

After mixing 13.39 parts of the salt represented by the formula (I-2-c) and 40 parts of acetonitrile, they were stirred at 23° C. for 30 minutes.

To the mixture, 11.63 parts of the compound represented by the formula (I-1-d) was added, followed by being stirred at 40° C. for 1 hour.

To the reaction mixture, a mixed solution containing 8.47 parts of the salt represented by the formula (I-1-e) and 20 parts of acetonitrile, followed by being stirred at 23° C. for 3 hours.

The obtained mixture was concentrated, and then separated using column [silica gel 60N (spherical shape, neutral), 100 to 210 μm, eluent: mixture of n-heptane and ethyl acetate (n-heptane/ethyl acetate=1/2)] to obtain 10.22 parts of the salt represented by the formula (I-2-f).

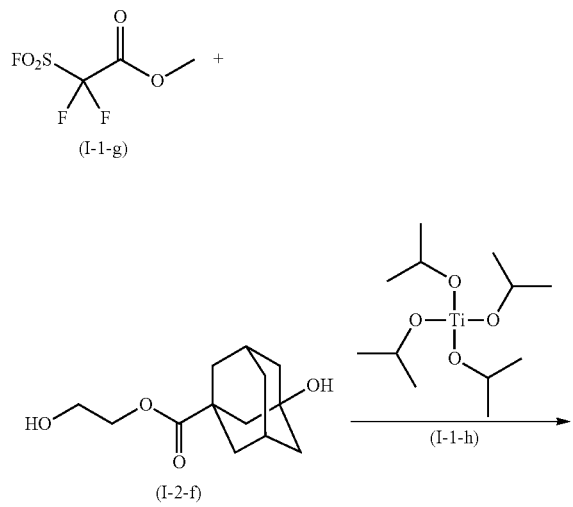

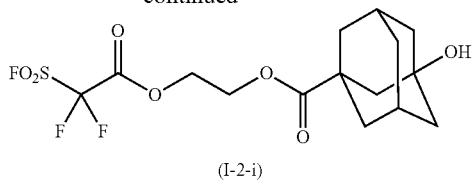

Into the reactor, 3 parts of the compound represented by the formula (I-1-g), 5.53 parts of the compound represented by the formula (I-2-f), 80 parts of chloroform and 1.34 parts of the compound represented by the formula (I-1-h) were fed and stirred at 23° C. for 30 minutes, followed by being refluxed at 80° C. for 5 hours while removing water which was generated by the reflux. After the reflux, the obtained mixture was cooled to 23° C., and 6.8 parts of silica gel was added thereto and stirred at 23° C. for 30 minutes, followed by being filtrated. The obtained filtrate was concentrated to obtain 5.68 parts of the salt represented by the formula (I-2-i)

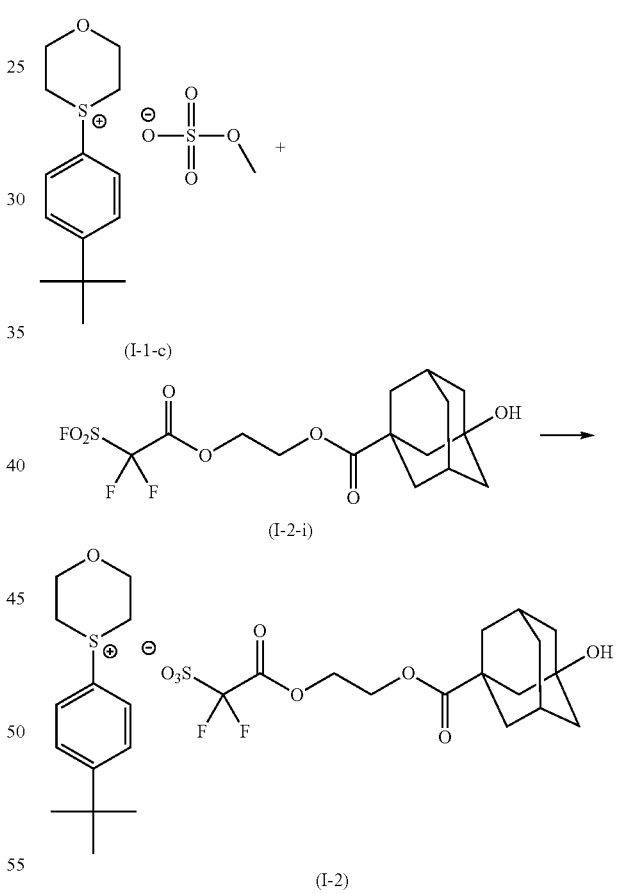

Into a reactor, 5.68 parts of the compound represented by the formula (I-1-c), 57.1 parts of chloroform, 19.9 parts of ion-exchanged water and 3.02 parts of triethylamine were added and stirred at 23° C. for 30 minutes, followed by being cooled to 5° C.

To the obtained mixture, a mixed solution of 5.44 parts of the compound represented by the formula (I-2-i) and 5.44 parts of chloroform was dropped for 30 minutes, and stirred at 23° C. for one hour, followed by separating an organic layer.

To the obtained organic layer, 33 parts of 5% aqueous oxalic acid solution was added, stirred at 23° C. for 30 minutes, followed by separating an organic layer. To the obtained organic layer, 33 parts of ion-exchanged water was added and stirred at 23° C. for 30 minutes, followed by separating an organic layer. The washing step with water was conducted three times. The washed organic layer was concentrated. To the obtained residue, 30 parts of tert-butylmethylether was added and removed supernatant therefrom.

The obtained residue was concentrated to obtain 4.34 parts of the salt represented by formula (I-2).

MS (ESI(+) Spectrum): M+ 237.1
MS (ESI(−) Spectrum): M− 397.1

Example 3

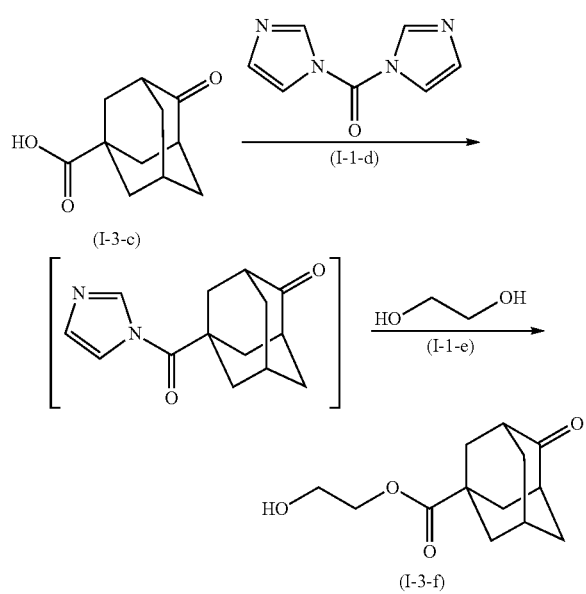

After mixing 13.25 parts of the salt represented by the formula (I-3-c) and 40 parts of acetonitrile, they were stirred at 23° C. for 30 minutes.

To the mixture, 11.63 parts of the compound represented by the formula (I-1-d) was added, followed by being stirred at 40° C. for 1 hour.

To the reaction mixture, a mixed solution containing 8.47 parts of the salt represented by the formula (I-1-e) and 20 parts of acetonitrile, followed by being stirred at 23° C. for 3 hours.

The obtained mixture was concentrated, and then separated using column [silica gel 60N (spherical shape, neutral), 100 to 210 μm, eluent: mixture of n-heptane and ethyl acetate (n-heptane/ethyl acetate=1/2)] to obtain 10.34 parts of the salt represented by the formula (I-3-f).

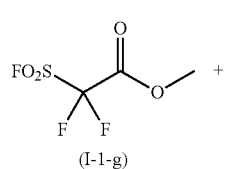

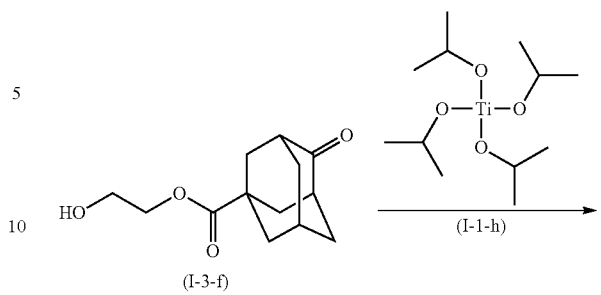

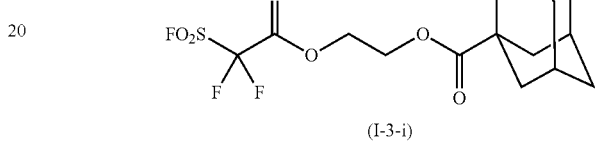

Into the reactor, 3 parts of the compound represented by the formula (I-1-g), 5.48 parts of the compound represented by the formula (I-3-f), 80 parts of chloroform and 1.34 parts of the compound represented by the formula (I-1-h) were fed and stirred at 23° C. for 30 minutes, followed by being refluxed at 80° C. for 5 hours while removing water which was generated by the reflux. After the reflux, the obtained mixture was cooled to 23° C., and 6.8 parts of silica gel was added thereto and stirred at 23° C. for 30 minutes, followed by being filtrated. The obtained filtrate was concentrated to obtain 5.75 parts of the salt represented by the formula (I-3-i).

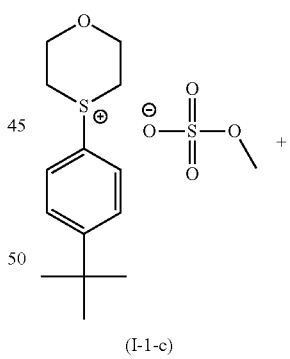

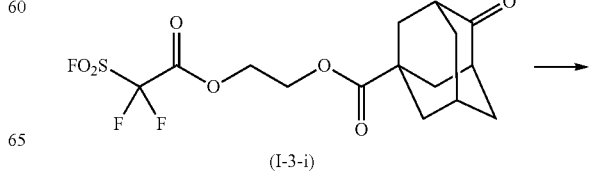

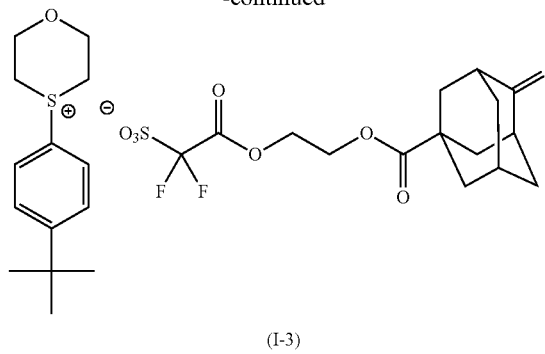

(I-3)

Into a reactor, 5.68 parts of the compound represented by the formula (I-1-c), 57.1 parts of chloroform, 19.9 parts of ion-exchanged water and 3.02 parts of triethylamine were added and stirred at 23° C. for 30 minutes, followed by being cooled to 5° C.

To the obtained mixture, a mixed solution of 5.41 parts of the compound represented by the formula (I-3-i) and 5.41 parts of chloroform was dropped for 30 minutes, and stirred at 23° C. for one hour, followed by separating an organic layer.

To the obtained organic layer, 33 parts of 5% aqueous oxalic acid solution was added, stirred at 23° C. for 30 minutes, followed by separating an organic layer. To the obtained organic layer, 33 parts of ion-exchanged water was added and stirred at 23° C. for 30 minutes, followed by separating an organic layer. The washing step with water was conducted three times. The washed organic layer was concentrated. To the obtained residue, 30 parts of tert-butylmethylether was added and removed supernatant therefrom.

The obtained residue was concentrated to obtain 4.49 parts of the salt represented by formula (I-3).

MS (ESI(+) Spectrum): M$^+$ 237.1
MS (ESI(−) Spectrum): M$^-$ 395.1

Example 4

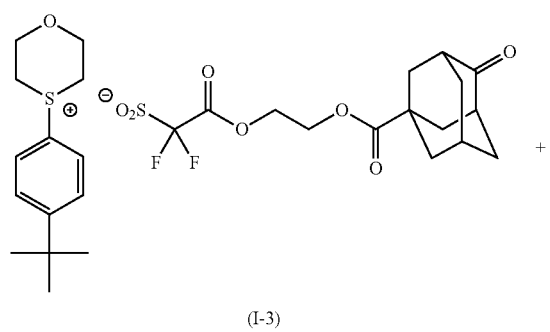

(I-3)

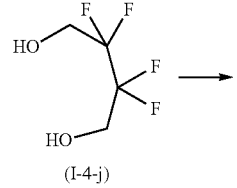

(I-4-j)

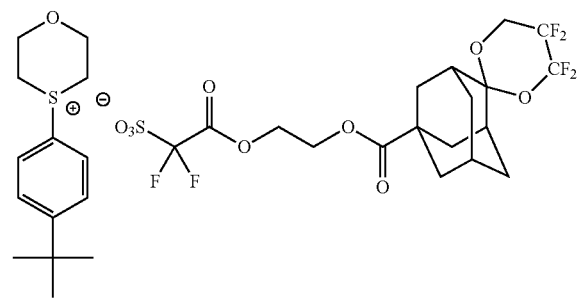

(I-4)

Into a reactor, 1.9 parts of the compound represented by the formula (I-3), 0.73 parts of the compound represented by the formula (I-4-j) and 10 parts of 1,2-dichloroethane were added and stirred at 23° C. for 30 minutes.

To the obtained mixture, 0.01 parts of p-toluenesulfonic acid was added, and refluxed and stirred at 100° C. for 3 hours, followed by being cooled to 23° C. Then 30 parts of chloroform and 10 parts of 5% aqueous sodium hydrogen carbonate solution was added, stirred at 23° C. for 30 minutes, followed by setting still to separate an organic layer.

To the obtained organic layer, 10 parts of ion-exchanged water was added, and stirred at 23° C. for 30 minutes, followed by separating an organic layer. The washing step with water was conducted seven times.

Then 1 part of active carbon was added to the obtained organic layer and stirred at 23° C. for 30 minutes, followed by being filtrated.

To the obtained residue, 10 parts of tert-butylmethylether was added and stirred, followed by being filtrated to obtain 0.38 parts of the salt represented by formula (I-4).

MS (ESI(+) Spectrum): M$^+$ 237.1
MS (ESI(−) Spectrum): M$^-$ 539.1

Example 5

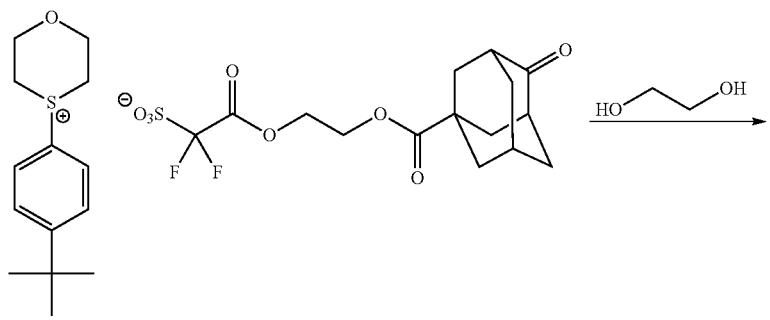

(I-3)

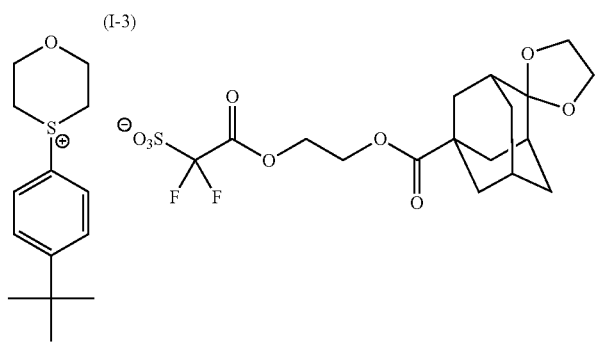

(I-17)

Into a reactor, 1.77 parts of the salt represented by the formula (I-3) and 10 parts of ethylene glycol were charged, stirred at 23° C. for 30 minutes, and then the temperature of the obtained mixture was increased to 103° C. To the obtained mixture, 0.02 parts of sulfuric acid was added, and stirred at 103° C. for one 15 hour, and then cooled into 23° C. To the obtained mixture, 20 parts of chloroform and 10 parts of ion-exchanged water were added, and stirred at 23° C. for 30 minutes, followed by separating an organic layer. The washing step with water was conducted three times. The washed organic layer was concentrated. To the obtained concentrate, 10 parts of acetonitrile was added, stirred at 23° C. for 30 minutes, and concentrated. To the obtained concentrate, 10 parts of ethyl acetate was added, stirred at 23° C. for 30 minutes, and removed supernatant therefrom. The obtained residue was concentrated to obtain 1.62 parts of the salt represented by formula (I-17).

MS (ESI(+) Spectrum): $M^+$ 237.1

MS (ESI(−) Spectrum): $M^-$ 439.1

Synthesis Example 1

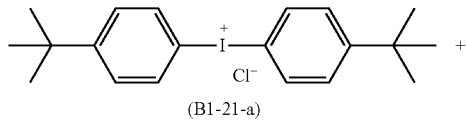

(B1-21-a)

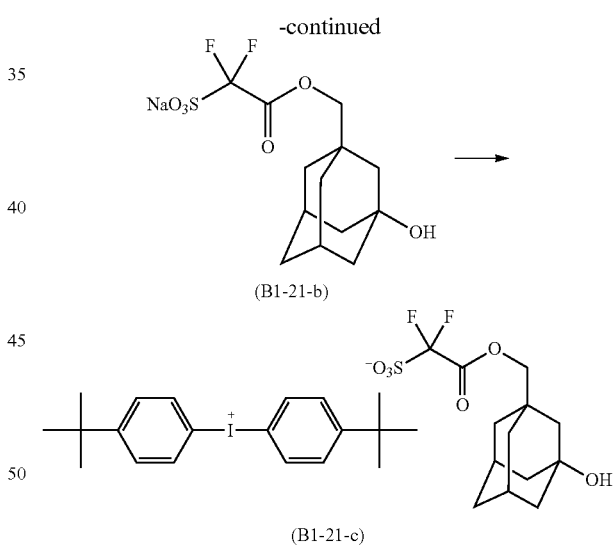

(B1-21-b)

(B1-21-c)

In a reactor, 30.00 parts of the salt represented by the formula (B1-21-b) which had been produced according to the method described in JP 2008-209917 A, 35.50 parts of the salt represented by the formula (B1-21-a), 100 parts of chloroform and 50 parts of ion-exchanged water were fed and stirred at 23° C. for 15 hours. From the obtained reaction mixture which had two phases, a chloroform phase was collected with separation.

The chloroform phase was washed with 30 parts of ion-exchanged water for washing: This washing was conducted five times.

The washed chloroform phase was concentrated. To the obtained residue, 100 parts of tert-butylmethylether was added and then stirred at 23° C. for 30 minutes, followed by being filtrated to obtain 48.57 parts of the salt represented by the formula (B1-21-c).

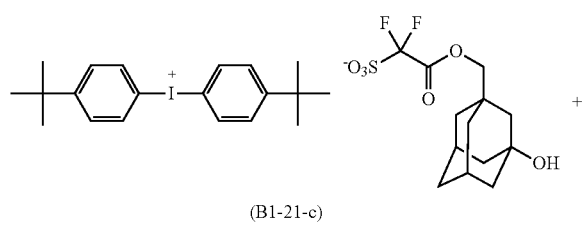

(B1-21-c)

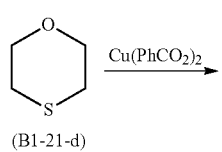

(B1-21-d)

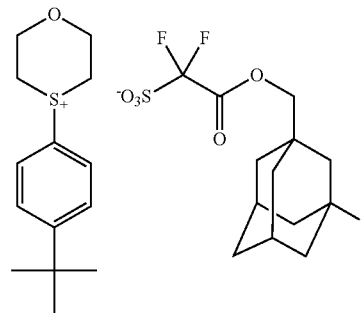

(B1-21)

Into a reactor, 20.00 parts of the salt represented by the formula (B1-21-c), 2.84 parts of the compound represented by the formula (B1-21-d) and 250 parts of monochlorobenzene were fed and then they were stirred at 23° C. for 30 minutes.

To the resultant mixture, 0.21 part of copper (II) dibenzoate was added. The resultant mixture was stirred at 100° C. for 1 hour. The mixture was concentrated, and then 200 parts of chloroform and 50 parts of ion-exchanged water were added to the obtained residue, followed by being stirred at 23° C. for 30 minutes. Then the organic phase was collected by separation. Then 50 parts of ion-exchanged water was added to the organic layer and stirred at 23° C. for 30 minutes, followed by collecting an organic phase by separation: This washing was conducted five times.

The washed organic layer was concentrated. To the residue, 53.51 parts of acetonitrile was added, and the resultant mixture was concentrated. To the residue, 113.05 parts of tert-butylmethylether was added and then they were stirred, followed by being filtrated to obtain 10.47 parts of the salt represented by the formula (B1-21).

MS (ESI(+) Spectrum): M⁺ 237.1
MS (ESI(−) Spectrum): M⁻ 339.1

Synthesis Example 2

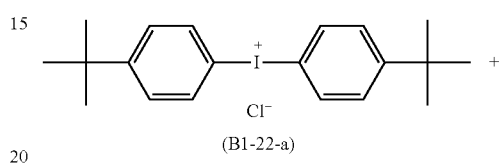

(B1-22-a)

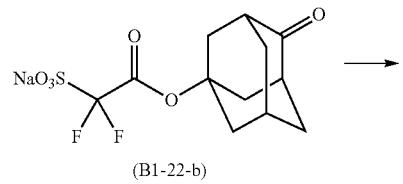

(B1-22-b)

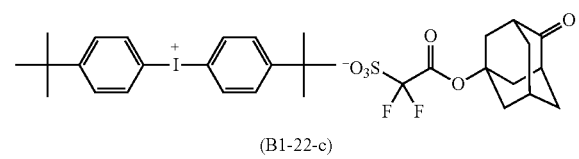

(B1-22-c)

Into a reactor, 11.26 parts of the salt represented by the formula (B1-22-a), 10.00 parts of the compound represented by the formula (B1-22-b), 50 parts of chloroform and 25 parts of ion-exchanged water was fed and then they were stirred at 23° C. for 15 hours.

From the obtained reaction mixture which had two phases, a chloroform phase was collected with separation.

The chloroform phase was washed with 15 parts of ion-exchanged water for washing: This washing was conducted five times.

The washed chloroform phase was concentrated. To the obtained residue, 50 parts of tert-butylmethylether was added and then stirred at 23° C. for 30 minutes, followed by being filtrated to obtain 11.75 parts of the salt represented by the formula (B1-22-c).

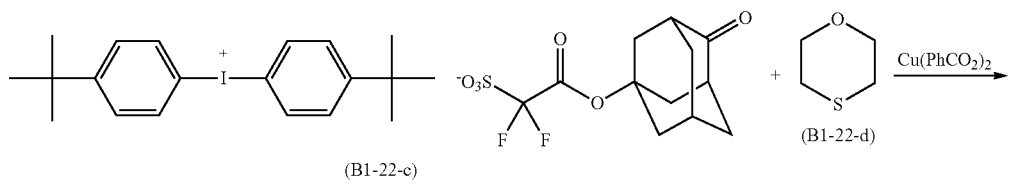

(B1-22-c)     (B1-22-d)

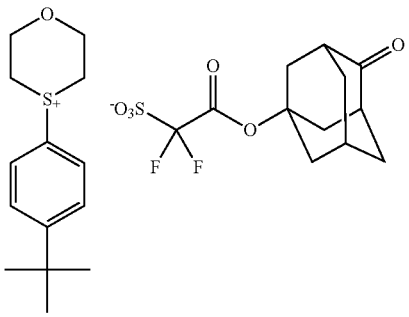

(B1-22)

Into a reactor, 11.71 parts of the salt represented by the formula (B1-22-c), 1.70 parts of the compound represented by the formula (B1-22-d) and 46.84 parts of monochlorobenzene were fed and then they were stirred at 23° C. for 30 minutes.

To the resultant mixture, 0.12 part of copper (II) dibenzoate was added. The resultant mixture was stirred at 100° C. for 30 minutes.

The mixture was concentrated, and then 50 parts of chloroform and 12.50 parts of ion-exchanged water were added to the obtained residue, followed by being stirred at 23° C. for 30 minutes. Then the organic phase was collected by separation. Then 12.50 parts of ion-exchanged water was added to the organic layer and they were stirred at 23° C. for 30 minutes, followed by collecting an organic phase by separation: This washing was conducted eight times.

The washed organic layer was concentrated. To the residue, 50 parts of tert-butylmethylether was added, followed by being filtrated to obtain 6.84 parts of the salt represented by the formula (B1-22).

MS (ESI(+) Spectrum): M$^+$ 237.1

MS (ESI(−) Spectrum): M$^-$ 323.0

Compounds used as monomers in the following Synthesis Examples are shown as follow.

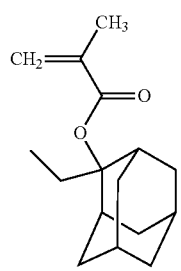

(a1-1-2)

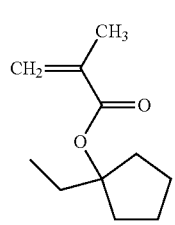

(a1-2-9)

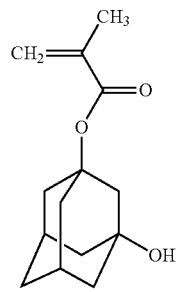

(a2-1-1)

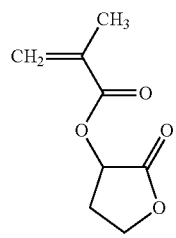

(a3-1-1)

Here, each of the compounds is referred as to "monomer (X)" where "X" is the symbol of the formula representing the monomer.

Synthesis Example 3

There were mixed monomers (a1-1-2), (a1-2-9), (a2-1-1) and (a3-1-1) in a molar ratio of 5/42/32/21 (monomer (a1-1-2)/monomer (a1-2-9)/monomer (a2-1-1)/monomer (a3-1-1)) as well as propyleneglycolmonomethylether acetate in twice amounts of all monomers to prepare a mixture. To the mixture, azobisisobutyronitrile and azobis (2,4-dimethylvaleronitrile) were added as initiators in the ratio of 1% by mole and 3% by mole based on molar amounts of all the monomers, and the obtained mixture was heated at 75° C. for about 5 hours. The reaction mixture was poured into a large amount of a mixture of methanol and water to cause precipitation. The precipitate was collected by filtration. Then the filtrates were dissolved in propyleneglycolmonomethylether acetate and poured the resultant solution into a large amount of a mixture of methanol and water to cause precipitation, followed by being filtrated: This operation was conducted twice for purification.

As a result, a resin having a weight-average molecular weight of about $9.1 \times 10^3$ was obtained in yield of 97%. This resin is called as Resin A1. Resin A1 had the following structural units.

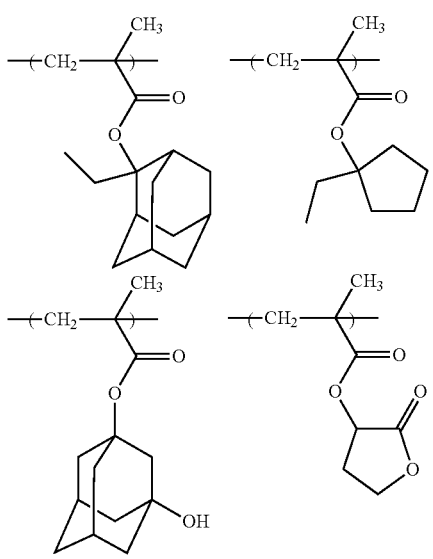

Examples 6 to 20 and Comparative Examples 1 to 3

Production of Photoresist Compositions

The following components as listed in Table 1 were mixed and dissolved in the solvent as mentioned below, and then filtrated through a fluorine resin filter having pore diameter of 0.2 μm, to prepare photoresist compositions.

I-4: Salt represented by formula (I-4)
I-17: Salt represented by formula (I-17)

<Acid Generator>

B1-21: Salt represented by formula (B1-21)
B1-22: Salt represented by formula (B1-22)
B1-x: Salt represented by the following formula, produced according to JP2001-16794A1.

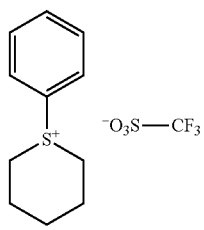

<Quencher>

D1: The compound of the following formula, which was manufactured by Tokyo Chemical Industries, Co., Ltd.

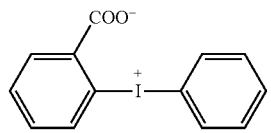

TABLE 1

| Comp. No. | Resin (kind/amount (part)) | Salt (I) (kind/amount (part)) | Acid generator (kind/amount (part)) | Quencher (kind/amount (part)) | PB (° C.)/ PEB (° C.) |
|---|---|---|---|---|---|
| Comp. 1 | A1/10 | I-1/1.0 | None | D1/0.2 | 90/85 |
| Comp. 2 | A1/10 | I-2/1.0 | None | D1/0.2 | 90/85 |
| Comp. 3 | A1/10 | I-3/1.0 | None | D1/0.2 | 90/85 |
| Comp. 4 | A1/10 | I-4/1.0 | None | D1/0.2 | 90/85 |
| Comp. 5 | A1/10 | I-2/0.4 | B1-21/0.2 B1-22/0.4 | D1/0.2 | 90/85 |
| Comp. 6 | A1/10 | I-3/0.4 | B1-21/0.6 | D1/0.2 | 90/85 |
| Comp. 7 | A1/10 | I-4/0.4 | B1-21/0.6 | D1/0.2 | 90/85 |
| Comp. 8 | A1/10 | I-1/1.0 | None | D1/0.2 | 100/95 |
| Comp. 9 | A1/10 | I-2/1.0 | None | D1/0.2 | 100/95 |
| Comp. 10 | A1/10 | I-3/1.0 | None | D1/0.2 | 100/95 |
| Comp. 11 | A1/10 | I-4/1.0 | None | D1/0.2 | 100/95 |
| Comp. 12 | A1/10 | I-2/0.4 | B1-21/0.2 B1-22/0.4 | D1/0.2 | 100/95 |
| Comp. 13 | A1/10 | I-3/0.4 | B1-21/0.6 | D1/0.2 | 100/95 |
| Comp. 14 | A1/10 | I-4/0.4 | B1-21/0.6 | D1/0.2 | 100/95 |
| Comp. 15 | A1/10 | I-17/1 | None | D1/0.2 | 100/95 |
| Compar. Comp. 1 | A1/10 | None | B1-21/0.6 B1-22/0.4 | D1/0.2 | 90/85 |
| Compar. Comp. 2 | A1/10 | None | B1-21/1.0 | D1/0.2 | 90/85 |
| Compar. Comp. 2 | A1/10 | None | B1-x/1.0 | D1/0.2 | 90/85 |

In Table 1, symbols represent the following components.

<Resin>
A1: Resin A1

<Salt (I)>
I-1: Salt represented by formula (I-1)
I-2: Salt represented by formula (I-2)
I-3: Salt represented by formula (I-3)

<Solvent>
E1: Mixture of the following solvents

| propyleneglycolmonomethylether acetate | 265 parts |
| propyleneglycolmonomethylether | 20 parts |
| 2-heptanone | 20 parts |
| γ-butyrolactone | 3.5 parts |

<Evaluation>

Silicon wafers (12 inches) with 100 nm thick of SiO$_2$ layer were treated with hexamethyldisilazane, and then baked at 120° C. for 60 seconds. One of the photoresist compositions prepared as above was spin-coated over the treated wafer so that the thickness of the resulting film became 240 nm after drying. The silicon wafer thus coated with the photoresist composition was prebaked on a direct hotplate at a temperature shown in the column "PB" in Table 1 for 60 seconds. Using an ArF excimer stepper for immersion exposure ("FPA 5000-AS3" manufactured by Canon, NA=0.75, 2/3 Annular), each wafer thus formed with the respective composition film was subjected to immersion exposure using a photomask for forming a line-and-space pattern having a line pitch of 200 nm and a line width of 100 nm with the exposure quantity being varied stepwise. Ultrapure water was used as an immersion medium.

After the exposure, each wafer was subjected to post-exposure baking on a hotplate at a temperature shown in the column "PEB" in Table 1 for 60 seconds and then to development in the manner of paddle development for 60 seconds with 2.38% by weight of aqueous tetrametylammonium hydroxide solution to make a photoresist pattern.

Effective sensitivity (ES): It was defined as the exposure quantity that the line width of the pattern became 100 nm after exposure and development.

Line Edge Roughness (LER) Evaluation

The photoresist pattern was observed and checked irregularity in wall surface, using a scanning electron microscope.

Table 2 illustrates the results thereof. The figures in parentheses represent roughness width (nm). Here, the term "roughness width" represents the value (nm) of the maximum difference in width of the pattern between the convex parts and the concavo parts.

TABLE 2

| Ex. No. | Composition | LER (nm) |
| --- | --- | --- |
| Ex. 6 | Comp. 1 | 7.7 |
| Ex. 7 | Comp. 2 | 7.4 |
| Ex. 8 | Comp. 3 | 7.5 |
| Ex. 9 | Comp. 4 | 7.4 |
| Ex. 10 | Comp. 5 | 7.5 |
| Ex. 11 | Comp. 6 | 7.5 |
| Ex. 12 | Comp. 7 | 7.4 |
| Ex. 13 | Comp. 8 | 7.5 |
| Ex. 14 | Comp. 9 | 7.2 |
| Ex. 15 | Comp. 10 | 7.3 |
| Ex. 16 | Comp. 11 | 7.2 |
| Ex. 17 | Comp. 12 | 7.4 |
| Ex. 18 | Comp. 13 | 7.4 |
| Ex. 19 | Comp. 14 | 7.3 |
| Ex. 20 | Comp. 15 | 7.3 |
| Comparative Ex. 1 | Compar. Comp. 1 | 7.9 |
| Comparative Ex. 2 | Compar. Comp. 2 | 7.9 |
| Comparative Ex. 3 | Compar. Comp. 3 | 8.6 |

The salt of the disclosure is suitable for an acid generator and the photoresist composition containing the salt provides a good photoresist pattern with reduced line edge roughness, even when the pattern is produced on the relatively thick film. Therefore, the photoresist composition is suitable for implantation in the field of the semiconductor production.

What is claimed is:

1. A salt represented by the formula (I):

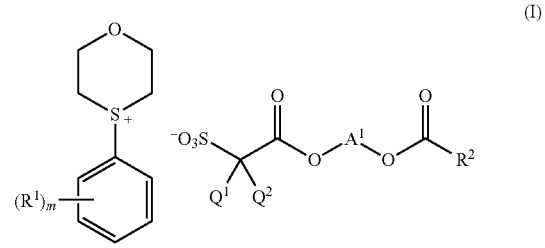

wherein $Q^1$ and $Q^2$ each independently represent a fluorine atom or a $C_1$ to $C_6$ perfluoroalkyl group;

$R^1$ represents a $C_1$ to $C_{12}$ alkyl group in which a methylene group may be replaced by an oxygen atom or a carbonyl group;

$A^1$ represents a $C_2$ to $C_8$ unsubstituted alkanediyl group; and $R^2$ represents a $C_5$ to $C_{18}$ alicyclic hydrocarbon group in which a hydrogen atom may be replaced by a hydroxy group, and in which a methylene group may be replaced by an oxygen atom or a carbonyl group, and which alicyclic hydrocarbon group may have a cyclic ketal structure optionally having a fluorine atom; and "m" represents an integer of 0, 1, 2 or 3.

2. The salt according to claim 1 wherein the alicyclic hydrocarbon group for $R^2$ is an adamantyl group.

3. The salt according to claim 1 wherein $R^1$ represents a $C_1$ to $C_6$ alkyl group.

4. An acid generator which comprises the salt according to claim 1.

5. A photoresist composition which comprises the salt according to claim 1 and a resin having an acid-labile group.

6. The photoresist composition according to claim 5, which further comprises a salt which generates an acid weaker in acidity than an acid generated from the salt according to claim 1.

7. A process for producing a photoresist pattern comprising the following steps (1) to (5):

(1) a step of applying the photoresist composition according claim 5 on a substrate, (2) a step of forming a composition film by conducting drying, (3) a step of exposing the composition film to radiation, (4) a step of baking the exposed composition film, and (5) a step of developing the baked composition film.

* * * * *